US011426093B2

(12) United States Patent
Hatch

(10) Patent No.: US 11,426,093 B2
(45) Date of Patent: Aug. 30, 2022

(54) ENERGY CONVERSION MONITORING DEVICES, SYSTEMS, AND METHODS

(71) Applicant: REVEAL BIOSENSORS, INC., San Jose, CA (US)

(72) Inventor: Guy Meredith Hatch, Logan, UT (US)

(73) Assignee: REVEAL BIOSENSORS, INC., San Jose, CA (US)

(*) Notice: Subject to any disclaimer, the term of this patent is extended or adjusted under 35 U.S.C. 154(b) by 407 days.

(21) Appl. No.: 16/572,106

(22) Filed: Sep. 16, 2019

(65) Prior Publication Data

US 2020/0085321 A1   Mar. 19, 2020

Related U.S. Application Data

(60) Provisional application No. 62/732,876, filed on Sep. 18, 2018.

(51) Int. Cl.
*A61B 5/02*      (2006.01)
*A61B 5/026*     (2006.01)
(Continued)

(52) U.S. Cl.
CPC .......... *A61B 5/0261* (2013.01); *A61B 5/0075* (2013.01); *A61B 5/0205* (2013.01);
(Continued)

(58) Field of Classification Search
CPC ... A61B 5/0261; A61B 5/0075; A61B 5/0205; A61B 5/0826; A61B 5/1116;
(Continued)

(56) References Cited

U.S. PATENT DOCUMENTS 5,830,137 A    11/1998  Scharf
6,801,799 B2   10/2004  Mendelson
(Continued)

FOREIGN PATENT DOCUMENTS

JP       6099607 B2     3/2017
WO     2015168235 A1    11/2015
(Continued)

*Primary Examiner* — Rex R Holmes
(74) *Attorney, Agent, or Firm* — Buchalter; Cecily Anne O'Regan

(57) ABSTRACT

Persons with sleep disordered breathing (SDB) may, or may not, recognize that they have symptoms of SDB, and/or that they may be at-risk of, or suffering certain health problems associated with SDB, including death. The disclosed Energy Conversion Monitor (ECM) sensor, when embodied, for example, in a wearable upper-armband format, has been demonstrated to be more sensitive and responsive than pulse oximetry monitoring of blood oxygen saturation as an indication of hypoxic stress induced by SDB, and is compatible with: (1) inclusion in sleep laboratory polysomnograph (PSG) testing instrumentation, (2) home-based diagnostic testing for SDB, (3) control of home-use airway therapy devices, (4) continuous remote surveillance and refinement of airway therapy, and (5) spot-check and continuous surveillance of sleep quality in the general population. The disclosed ECM also provides new measurements of physiologic stress during and following exercise. When applied during initial care of premature newborn infants, it offers improved therapeutic guidance during their transition from their limited in utero oxygen supply conditions, to the increased oxygen availability from breathing air. When applied during resuscitation of persons suffering from hypoxia and during reperfusion of ischemic tissue, such as during treatment of ischemic stroke, or ischemic heart attack, the ECM sensor can provide objective guidance regarding the safe and effective resupply of oxygen to the (Continued)

hypoxia-adapted tissue to help reduce or prevent microvascular occlusion and cellular injury. As a continuously worn physiologic surveillance monitor, the ECM offers the potential of early detection of sepsis. With the elderly and infirm, it offers a convenient and comfortable means of continuously assessing variations in status while awake and asleep.

31 Claims, 31 Drawing Sheets

(51) Int. Cl.
| | |
|---|---|
| A61B 5/00 | (2006.01) |
| A61B 5/11 | (2006.01) |
| A61B 5/08 | (2006.01) |
| A61M 21/00 | (2006.01) |
| A61B 5/0205 | (2006.01) |
| A61B 5/022 | (2006.01) |
| A61B 5/024 | (2006.01) |
| A61B 5/1455 | (2006.01) |

(52) U.S. Cl.
CPC .......... *A61B 5/0826* (2013.01); *A61B 5/1116* (2013.01); *A61B 5/412* (2013.01); *A61B 5/443* (2013.01); *A61B 5/4809* (2013.01); *A61B 5/4818* (2013.01); *A61B 5/4836* (2013.01); *A61B 5/6814* (2013.01); *A61M 21/00* (2013.01); *A61B 5/022* (2013.01); *A61B 5/02416* (2013.01); *A61B 5/14551* (2013.01); *A61B 2503/04* (2013.01); *A61B 2503/10* (2013.01); *A61B 2503/20* (2013.01); *A61B 2503/22* (2013.01); *A61M 2021/0022* (2013.01); *A61M 2021/0083* (2013.01)

(58) Field of Classification Search
CPC ....... A61B 5/412; A61B 5/443; A61B 5/4809; A61B 5/4818; A61B 5/4836; A61B 5/6814; A61B 5/022; A61B 5/02416; A61B 5/14551; A61B 2503/04; A61B 2503/10; A61B 2503/20; A61B 2503/22; A61B 2562/146; A61B 2562/16; A61B 5/14552; A61B 5/6824; A61M 21/00; A61M 2021/0022; A61M 2021/0083; A61M 16/0051; A61M 16/0069; A61M 2016/0027; A61M 2205/3313; A61M 2205/3553; A61M 2205/3569; A61M 2205/3584; A61M 2205/3592; A61M 2205/505; A61M 2205/52; A61M 2205/8206; A61M 2205/8243; A61M 2209/088; A61M 2210/04; A61M 2230/40; A61M 2230/50; A61M 2230/62; A61M 2230/63; A61M 16/024

See application file for complete search history.

(56) References Cited

U.S. PATENT DOCUMENTS

| | | | |
|---|---|---|---|
| 7,691,067 B2 * | 4/2010 | Westbrook | A61B 5/14551 |
| | | | 600/485 |
| 7,738,935 B1 | 6/2010 | Turcott | |
| 8,073,516 B2 | 12/2011 | Scharf et al. | |
| 8,133,176 B2 | 3/2012 | Porges et al. | |
| 8,346,327 B2 | 1/2013 | Campbell et al. | |
| 9,125,563 B2 | 9/2015 | Abrams et al. | |
| 9,357,954 B2 | 6/2016 | Li et al. | |
| 10,327,710 B2 | 6/2019 | Ulrich et al. | |
| 10,335,072 B2 | 7/2019 | Al-Ali et al. | |
| 10,369,310 B2 | 8/2019 | Ramanan et al. | |
| 10,376,670 B2 | 8/2019 | Shouldice et al. | |
| 10,383,569 B2 | 8/2019 | Douglas et al. | |
| 10,561,863 B1 * | 2/2020 | Dashevsky | A61B 5/14542 |
| 2002/0124295 A1 * | 9/2002 | Fenwick | A61B 5/02055 |
| | | | 2/69 |
| 2006/0009685 A1 | 1/2006 | Finarov et al. | |
| 2008/0081966 A1 | 4/2008 | Debreczeny | |
| 2008/0208009 A1 | 8/2008 | Shklarski | |
| 2010/0324390 A1 | 12/2010 | McLaughlin et al. | |
| 2011/0054336 A1 | 3/2011 | Jornod | |
| 2013/0303921 A1 | 11/2013 | Chu et al. | |
| 2013/0317331 A1 | 11/2013 | Bechtel et al. | |
| 2014/0194793 A1 | 7/2014 | Nakata et al. | |
| 2014/0275888 A1 | 9/2014 | Wegerich et al. | |
| 2015/0011854 A1 | 1/2015 | Frix et al. | |
| 2015/0057511 A1 | 2/2015 | Basu | |
| 2016/0007892 A1 * | 1/2016 | Esenaliev | A61B 5/742 |
| | | | 600/309 |
| 2017/0049336 A1 | 2/2017 | Hatch | |
| 2017/0112422 A1 | 4/2017 | Hatch | |
| 2017/0354372 A1 * | 12/2017 | Varadan | A61B 5/25 |

FOREIGN PATENT DOCUMENTS

| | | |
|---|---|---|
| WO | 2020061157 A1 | 3/2020 |
| WO | 2018136501 A1 | 7/2021 |

* cited by examiner

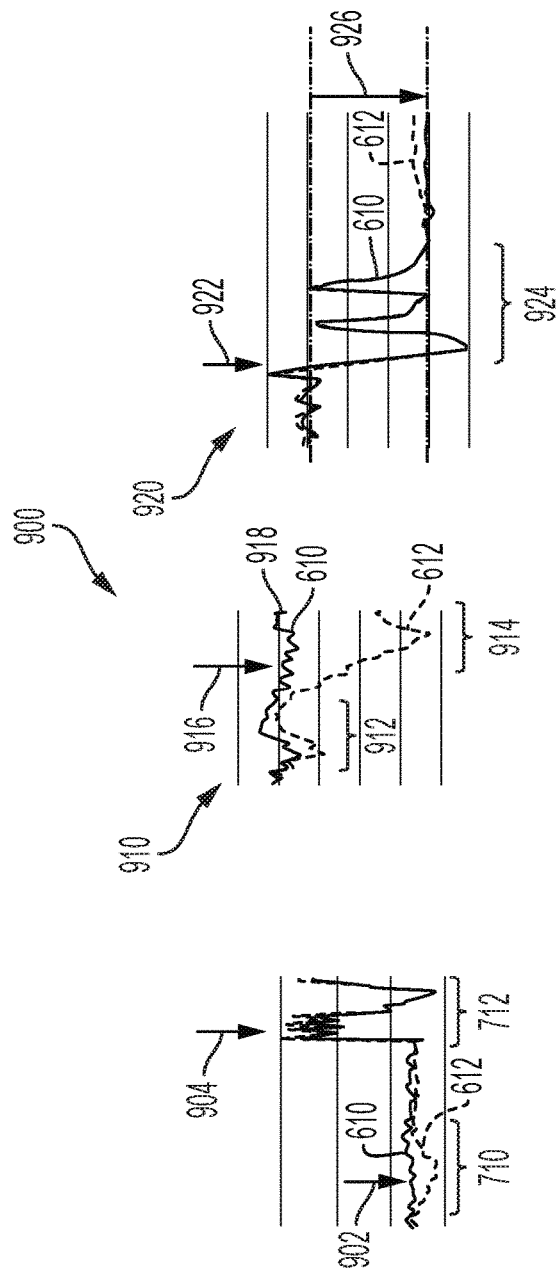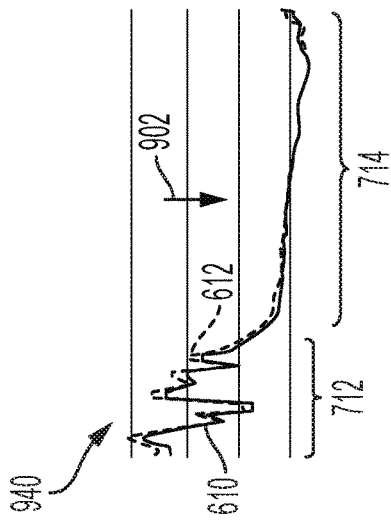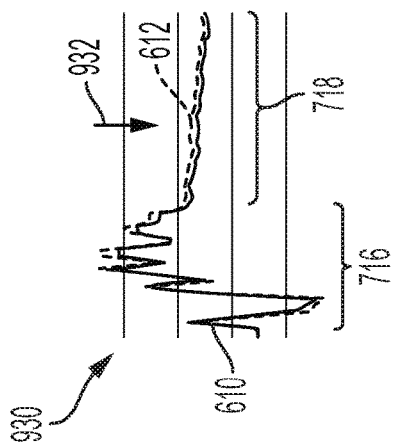

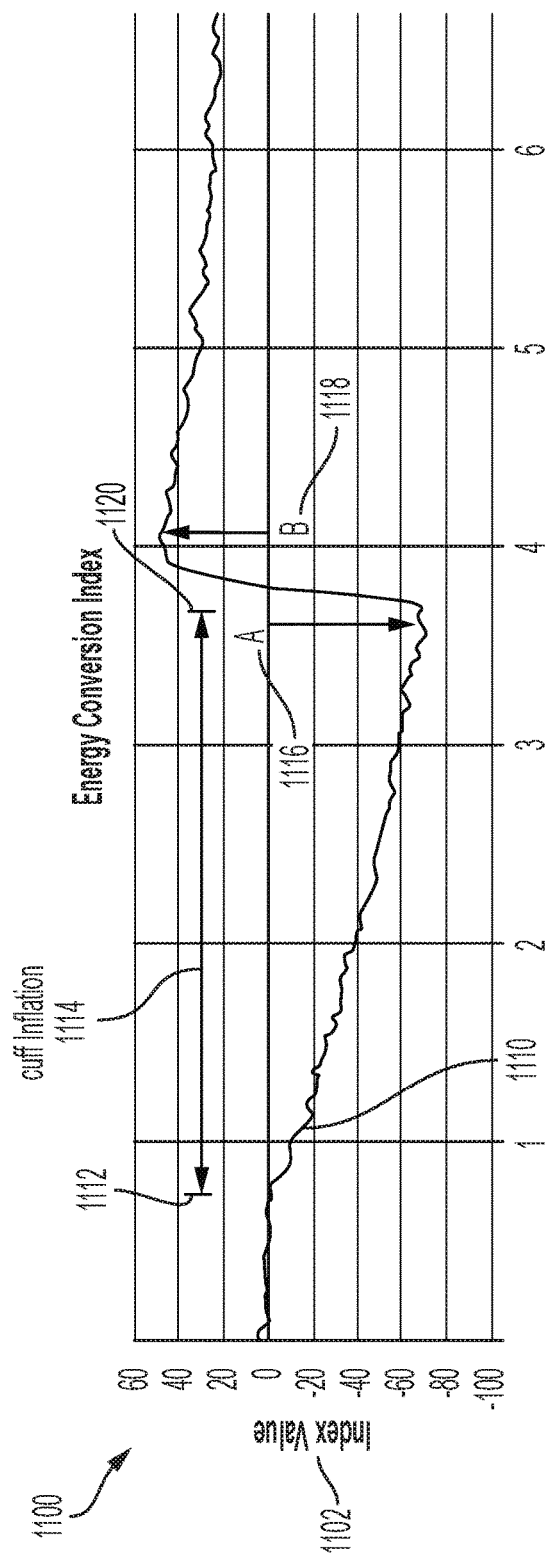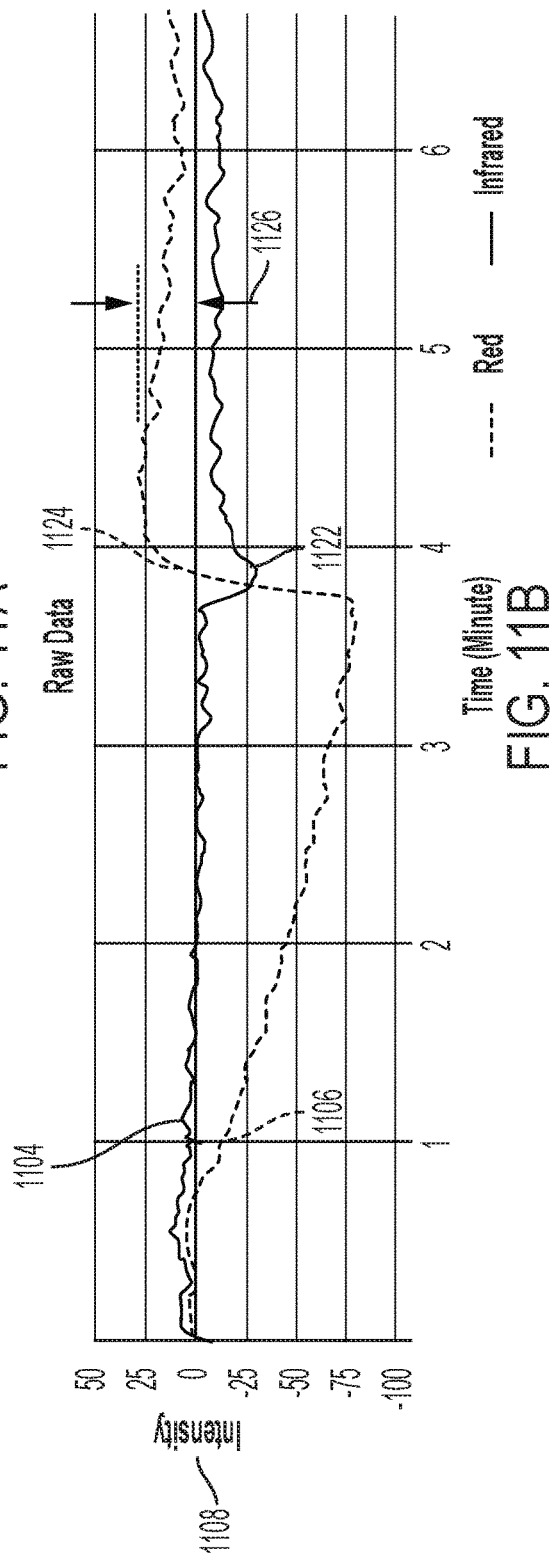
FIG. 11A
FIG. 11B

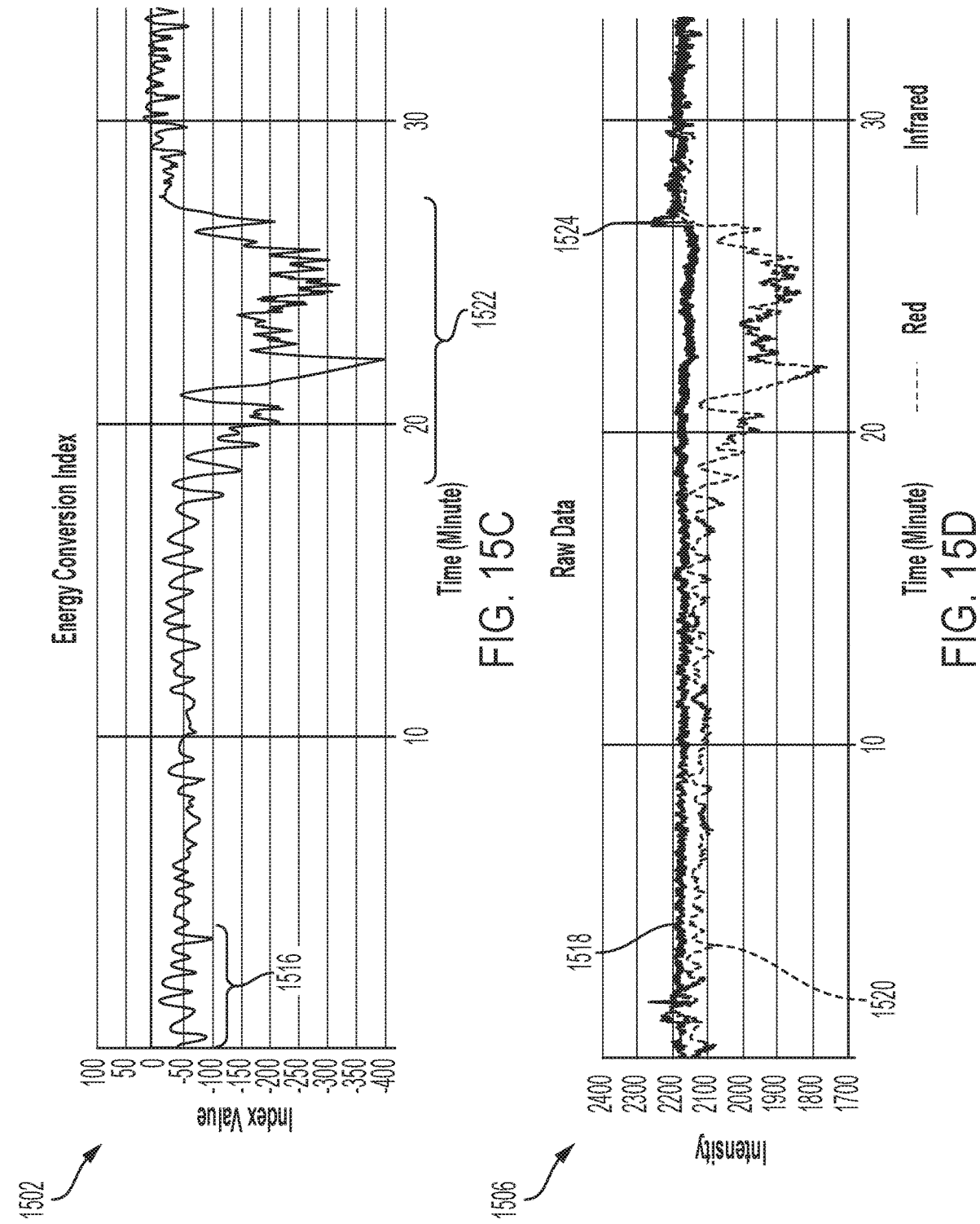

ENERGY CONVERSION MONITORING DEVICES, SYSTEMS, AND METHODS

CROSS-REFERENCE

This application claims the benefit of U.S. Provisional Application No. 62/732,876, filed Sep. 18, 2018, entitled Sleep Disordered Breathing Monitors, Systems and Methods, which application is incorporated herein in its entirety by reference.

BACKGROUND

Field

Disclosed are sensor devices, systems, and methods for monitoring oxygen-related physiology of the human body. Specifically, sensor systems of the disclosure provide for real-time and near real-time, non-invasive monitoring of need for oxygen vs. supply of oxygen at the cellular level. The systems, devices and methods monitor the full range of oxygen-based physiology, from 'not enough cellular oxygen' (cellular hypoxia), through 'just right' (aerobic metabolism), to 'too much cellular oxygen' (cellular hyperoxia).

Background

Current clinical methods of monitoring oxygen intake during sleep, for example, are limited to indirectly measuring the oxygen saturation of blood hemoglobin by pulse oximetry ($SpO_2$), which indicates the supply of oxygen in the blood, with the assumption that if the blood level of oxygen is within the 'normal range,' vital organ tissue will be safely and effectively supplied with oxygen to meet the cellular need for oxygen. However, through experiments and a proof of concept (POC) clinical study, it is determined that the physiologic stress and pathology associated with sleep-disordered breathing (SDB) occurs at the cellular level; not in the blood. The long-held assumption about adequate cellular oxygen supply with 'normal' oxygen saturation blood has not been verified due to lack of a sensor able to discern if the cellular need for oxygen is being adequately met or exceeded.

Blood oxygen level measures how much oxygen a person's red blood cells are carrying. Under normal conditions the body closely regulates the blood oxygen level to maintain a consistent range of oxygen-saturated blood. People with abnormal lung function may need to monitor blood oxygen levels to determine if treatments are working or need adjustment. One way of testing blood oxygen level is with an arterial blood gas test. This test requires that blood be drawn from an artery (typically the wrist). The blood is then sent to a lab for testing. Another option is the use of a pulse oximeter device. The pulse oximeter provides an estimate of a percentage of blood oxygen saturation with a 2% error rate.

While blood oxygen saturation is clinically important information, the adequacy of cellular oxygen supply, vs. cellular need for oxygen, is key to sustaining vital functions and avoiding cellular injury. Several instruments, called 'tissue oximeters,' claim to measure tissue oxygen supply status by timed sampling of light absorption through skin, or deeper, tissue; attributing these signal changes to be coming only from blood. Where the 'peak' and 'trough' signal sampling used in pulse oximeters effectively excludes variations in signal due to capillary and venous blood, and to cellular chemistry, the timed sampling in 'tissue oximeters' cannot exclude these major confounding contributions. 'Tissue oximeters' process their detected signals with $Log_{10}$ ratio computation as is used in pulse oximeters and, per the assumption that the signal variations are due to blood, calibrate with hemoglobin to produce a percent (0% to 100%) 'tissue oxygen saturation' ($StO_2$). Under minimal stress conditions, the $StO_2$ data responds generally like pulse oximetry. However, when blood flow to the monitored tissue is stopped, then restarted, the interpretation of $StO_2$ signal responses having originated only from blood becomes deeply flawed. The recorded magnitude of detected signal variation upon reperfusion (up to 20% full scale at 685 nm) is far too large to be due to oxygen saturation change in capillary blood, which occupies less than 1% of the sensor light path in the skin. The timing and direction of spectral absorption responses upon reperfusion are also inconsistent with blood volume or with oxygen transfer from the blood. Collectively, these experimental results cast doubt on the assumptions and methods currently applied in 'tissue oximeters.'

Sleep disordered breathing (SDB) is an increasingly recognized major health problem in people of all ages, from premature newborn infants to the elderly. The rising societal cost of SDB, and of associated obesity, includes increased transportation accidents, lost worker productivity, and increased incidence of major co-morbidity health problems, including hypertension, heart attack, atrial fibrillation, and stroke. The most typical SDB events are airway obstruction, due to relaxation of tongue, soft palate, and throat muscles during sleep (Obstructive Sleep Apnea (OSA)), and decreased central nervous system breathing drive, (Central Sleep Apnea (CSA)). Once diagnosed with sleep apnea, patients are typically prescribed an airway therapy device. Airway therapy devices include positive airway pressure devices such as a continuous positive airway pressure (CPAP) machine, which delivers one steady airway pressure and is used with the assumption that patients have the same continuous issues over time. Alternatively, an automatically-regulating positive airway pressure (APAP) machine, that adjusts pressure in a feedback controlled manner, is most commonly used with OSA patients who have changes in the patency of their airway during sleep. Patients with CSA have difficulty with timing and with sufficient effort of breathing during sleep, and are often treated with bilevel positive airway pressure (BiPAP) machines that provide increased pressure assistance with individual breaths. Variable positive airway pressure machines (VPAP) are used when decreased airflow resistance during exhalation is needed. Oral appliance therapy may be appropriate for treatment of mild SDB, but its effectiveness needs to be validated with individual users.

Several major areas of human disease are clinically recognized as having strong statistical association, if not direct cause-effect relationship, with the occurrence of SDB, including ischemic stroke, atrial fibrillation, and heart attack. It has also long been clinically assumed that there is a cause-effect physiologic relationship between snoring and risk of high blood pressure, or hypertension. However, polysomnography (PSG) sleep studies, which include continuous monitoring of arterial blood oxygen saturation by pulse oximetry ($SpO_2$), either do not detect, or do not show consistent occurrence of lowered blood oxygen, or hypoxemia, during snoring. Snoring during sleep, without a drop in $SpO_2$, is currently not 'scored' as a pathologic event in PSG sleep studies because there is no association with lowered blood oxygen. As a result of snoring not being scored as an SDB event, airway pressure devices (such as CPAP and APAP devices) are not covered by most medical health insurance policies or Medicare for snoring that does not result in lowered blood oxygen. Hypoxic stress at the cellular level is, apparently, occurring during snoring, but this cannot be detected by the PSG pulse oximeter.

Many other pathologic processes are statistically known to be aggravated by coincident SDB and could possibly be made less severe if the person's SDB was effectively treated. It is currently estimated that about 80% of the about 54 million adults in the United States (US) who suffer from SDB and/or SDB-related co-morbidities, are currently either not diagnosed or are not being effectively treated. Published research has also included sudden infant death syndrome (SIDS) as very likely due to an infant variant of SDB pathology, with peak incidence associated with nervous system development at about 2 months and extending to about one year of age.

The technical complexity of the PSG sensor system is especially limiting in the case of newborn infants afflicted with SDB. Effective screening of all newborn infants to assure stable breathing drive and functional airway during sleep may be needed to identify the infants who are at increased risk of SIDS. Currently, about 3,500 US infants die annually of SIDS, despite extensive efforts to educate parents about infant sleeping position, bedding, etc. Once identified, the at-risk infant needs to be provided a safe sleeping environment and be continuously and effectively monitored during all sleep periods, including daytime naps.

The 1994-1998 Collaborative Home Infant Monitor Evaluation (CHIME) study, included 1,079 infants, many of whom were considered to be at higher than baseline risk of SIDS because they were siblings of infants who had died of SIDS. This study provided conclusive evidence that SDB, including OSA and CSA, is a major factor in SIDS. Unfortunately, the mini-PSG monitor system used during the CHIME study was so difficult and time-consuming to apply that some parents were unwilling to fully comply with the study protocol; possibly contributing to the five study infant deaths that occurred while not being monitored.

Following the CHIME study, The American Academy of Pediatrics issued a policy statement that discourages use of currently available technology for home infant monitoring for the purpose of preventing SIDS. The Academy's position was that there is no infant monitoring system capable of recognizing and alarming to SDB events uniquely associated with SIDS in a timely-enough fashion to be useful for preventing death. Newborn intensive care unit (NICU) cardiorespiratory monitoring technology is the only available option, and is typically sent home with graduating premature newborns when the infant still needs to be monitored for 'apnea/bradycardia spells;' which is one of the premature infant-associated forms of SDB. Existing NICU monitoring technology was minimally adapted from adult monitors and, as such, is functionally unable to recognize research-identified breathing control, airway, and cellular oxygen supply problems that appear to be unique to infants at risk of SIDS. Additionally, because NICU monitoring technology is designed with the assumption that safe and effective operation requires the operator to be a qualified nurse or physician, its mechanical and operational complexity presents a significant barrier to effective use by parents at home. An unmet need remains for an easy to apply, fully effective SDB monitoring and alarming means that can be used for screening all newborn infants for SDB risk, and that can also be conveniently used by parents at home through their identified infant's period of SIDS risk extending from about 1 month to about 1 year of age.

Additionally, many children and young adults snore during sleep; some also with episodes of total obstruction of their airway during sleep due to enlarged tonsils and adenoids. Effective diagnosis currently requires these children to undergo a PSG study, which can be very frightening for a child. Surgical removal of enlarged tonsils and adenoids (commonly referred to as T&A surgery) to stop snoring during sleep has risks and may not be covered by medical insurance unless there is a formal PSG-based diagnosis of SDB, and/or medical record documentation of a specified number of group-A streptococcal throat infections.

Unfortunately, even those diagnosed as having SDB, and currently using an airway pressure device during sleep, may not be receiving fully-effective therapy. Many factors are involved in this low rate of diagnosis and borderline-effective treatment, including (1) the accessibility, high cost, and discomfort of PSG sleep studies in a sleep lab that are currently required for prescription and management of an airway pressure device at home, (2) the initial discomfort of therapy during sleep, and (3) the significant probability of less than optimal long-term management of therapy, primarily due to incomplete, or lack of, objective information beyond the PSG sleep study and initial titration of the airway pressure device settings.

One of the common threads in the above-mentioned areas of medical care is an unmet need for directly monitoring cellular oxygen supply that cannot be provided by pulse oximetry. This is also a significant challenge in several major health problems, including ischemic heart attack, ischemic stroke, organ transplant, and retinopathy of prematurity. Long-standing theory holds that the cellular injuries occur primarily during the ischemic or hypoxic phase of the condition. Cellular adaptation to insufficient oxygen supply has, apparently, not been considered to be a contributor. However, current research evidence clearly indicates that the beginning of reperfusion is the time when microvascular obstruction begins, followed by death of the surrounding tissue. This correlation indicates that cellular adaptation likely took place during the ischemic period, such that, upon reperfusion with 'normally' oxygenated blood, there was microvascular endothelial injury due to relatively excess oxygen supply, leading to white blood cell adhesion and obstruction of the capillaries and venules. Phase I of retinopathy of prematurity (ROP) appears to occur during the rapid increase in blood oxygen from the relatively low fetal range to the 'normal newborn' level at birth and during intensive care, apparently indicating cellular adaptation to the previous much lower fetal oxygen supply rate at the time of birth. Current research also indicates that microvascular obstruction and cellular injury occurs during reperfusion of transplant organs, apparently indicating cellular adaptation to the much lower oxygen supply during organ harvest and transport. Therefore, reperfusion of ischemic vital organ tissue may benefit from a more gradual resupply of oxygen; starting reperfusion with recipient venous blood, followed by blending in an increasing fraction of arterial blood until normally oxygenated arterial blood flow is tolerated without inducing injury. Premature newborn infants may benefit from starting initial care with breathing gas that provides 'placental' range oxygen availability, followed by gradual increase of oxygen content until breathing air is tolerated without injury. An apparent unmet need in all of these areas is for a means of indicating the upper threshold of cellular oxygen tolerance to help minimize or prevent these adverse therapeutic outcomes.

Pulse oximeters have known limitations during and following surgical anesthesia where surgical blood loss and blood dilution with IV fluids may result in insufficient oxygen delivery to vital organs. Oxygen delivery during surgical anesthesia is often maintained on the high end of normal, or even significantly excessive, in an attempt to provide a safety buffer against episodes of hypoxemia. Pulse oximetry cannot detect excess oxygen delivery and cannot provide a warning of potential, or actively occurring, harm from excess oxygen. Pulse oximetry also has significant limitations for Remote Patient Monitoring for post-hospital care surveillance and for management of chronic conditions. The awkward application site and motion intolerance of pulse oximeter sensors make them impractical for use as high-risk worker safety alarms that are needed by military and commercial pilots, astronauts, divers, firefighters, underground mine workers, and by other industrial workers in potentially toxic atmospheric environments.

SUMMARY

The disclosed devices, systems and methods provide for the detection and characterization of the physiologic components of SDB in comfortable and conveniently wearable formats configurable for all age groups. Application of the sensor can help reduce the societal costs of SDB by: (1) improving access to diagnosis of SDB with people of all ages by enabling optimal diagnostic testing in the sleep lab and at home, (2) optimizing the physiologic criteria defining payer coverage of airway pressure device therapy (and T&A surgery with children), (3) optimizing the effectiveness and comfort of airway pressure device therapy with physiology-based feed-back control, (4) validating the effectiveness of oral appliance therapy, and (5) spot-checking and continuous surveillance of sleep quality in the general population. Other needful application areas where the disclosed devices offer significant benefits include high-risk worker safety alarms for military/commercial pilots, astronauts, divers, firefighters, underground mine workers, and workers in other toxic industrial environments.

As will be appreciated by those skilled in the art, light can be described as having a wavelength and an intensity. The wavelength of light is, in the visible portion of the spectrum, commonly perceived by the eyes as the color of the light. In the visible portion of the spectrum, the intensity of light is seen by the eyes as the brightness of the light and, in a light-based sensor instrument, as the amount of photocurrent produced by a detector. The disclosed light-based sensor can use 685 nm+/−10 nm as a first center wavelength for detection of insufficient cellular oxygen supply. The sensor can use 850 nm+/−10 nm as a second center wavelength as a blank against which the 685 nm+/−10 nm signal is compared during less than and normal cellular oxygen supply. The sensor can also use 850 nm+/−10 nm as a second center wavelength for detection, by prolonged, decreased detected light intensity, of excess cellular oxygen supply. The sensor can detect an intensity value of light at 850 nm+/−10 nm after the light has passed through skin and then subtract that value from the detected intensity value at 685 nm+/−10 nm after that light has passed through the skin at each data acquisition cycle to produce an ECi data output value. Hereinafter, the use of 685 nm (red), or the use of 850 nm (infrared), indicate that these center wavelengths include center wavelengths within the respective range of +/−10 nm of these numeric values.

The disclosed sensor is an Energy Conversion Monitor (ECM). The ECi value scale it produces centers at zero when a person being tested is acclimated to the atmospheric oxygen supply and is awake, breathing normally, and at rest. Once multiple (e.g., two or more) ECi values are obtained while at rest, a negative-going trend line (less than zero) indicates less than the optimum cellular supply of oxygen is being received by the skin. Multiple ECi entries that produce a flat or near flat trend line centering around zero indicates a stable and normal status relative to cellular supply of oxygen in the skin. A positive-going trend (above zero) indicates that the skin may be receiving more cellular oxygen supply than is needed. Sensor detection of tandem variation in detected light signal that typically occurs with breathing and changes in body position can also be used to detect a photonic analog of breathing effort and body orientation during sleep.

The disclosed sensor systems are configurable to also include, for example, one or more of an electronic accelerometer sensor for detecting (a) mechanical vibration, (b) sensor/body orientation vs. earth gravity, and (c) body motion. Additional components of a sensor system include, but are not limited to, a skin surface temperature sensor and a vibrator motor for generating haptic (tactile) sensory stimulation, such as an attempt to abort a sensor system-recognized apnea event. The disclosed sensor is configurable to receive instructions and send data via, for example, BluetoothLE® RF communication to a device, such as a smartphone, running a custom software application ("app") as part of a disclosed sensor system.

Light-based sensors are disclosed that use oversampling and mathematical integration to compensate during initialization of the 685 nm light power level for the absorption of 685 nm light by skin pigment; thereby, enabling measurement through the full range of skin pigment level. With lightly to moderately pigmented skin the power level of the 685 nm light can be incrementally increased in, for example, 12-bit microcontroller D/A control voltage steps, until the averaged sample equals, or just exceeds 85% full scale, whereupon the successful control voltage level value is stored in sensor memory. Recording with the ECM under a wide variety of conditions and use cases shows a need for a minimum of 10% light intensity detection overhead, plus a 5% buffer to minimize saturating the A/D converter; thus, the 85% target. The disclosed averaged sample procedure could, for example, include obtaining a nominal number, such as 16, of burst samples of light intensity during illumination of the light, summing the 16 detected intensity values, then dividing the sum by the nominal number, 16, to help reduce the noise level in the signal. However, the 685 nm LED has an upper limit of sustainable power input that has been found by experiment to result in insufficient light output for optimum use with deeply pigmented skin. When the upper limit of sustainable LED power input is reached, but the averaged sample is still less than 85% full scale, and a further procedure involving an extended illumination period, oversampling, and mathematical integration will be used to achieve 85% full scale detected intensity. The oversampling and mathematical integration procedure is configurable so the sum of the total number of burst samples obtained will, when divided by the nominal burst sample number (e.g. 16), equal or just exceed 85% full scale. For example, initialization of the sensor on a person's darkly pigmented skin may require extending the illumination period of the 685 nm LED so that, for example, 25 burst sample values may be obtained, the sum of which when divided by 16, just exceeds 85% full scale. In this exemplary case, the design-specified full sustainable 685 nm LED power control value (e.g. 4095) and the total burst number of samples, 25, are stored in sensor memory to be used for operating the sensor during the current recording session.

Using more than the nominal number of burst samples, by the above disclosed method, produces the desired level of signal resolution and signal overhead range, but will slightly decrease the output signal/noise ratio, which may be mitigated with a low noise, high gain, and adequate bandwidth analog transimpedance amplifier for the detector signal.

The disclosed sensors are configurable to be applied to the mid-upper arm and used for monitoring during sleep. However, as will be appreciated by those skilled in the art, other application sites may include, for example, the wrist, torso, or legs. Based on experimental evidence to date, the mid-upper arm is an optimum location for positioning the ECM. However, other locations on the body can be used without departing from the scope of the disclosure. There are known differences between body locations in the detected sensitivity, data value range, and response timing of spectral optical density changes that occur. For instance, the same cellular hypoxia challenge induces a slightly delayed, but larger amplitude, sensor light intensity variation on the wrist, thigh, and lower leg, vs. the upper arm; requiring less amplification prior to digitization. Conversely, when applied on the mid-upper back, such as, for example, with aging adults suffering from dementia who are often intolerant of unfamiliar devices attached to their bodies, the ECM provides a lower amplitude signal variation compared with the upper arm location; requiring slightly more signal amplification to achieve the desired resolution.

The disclosed light-based sensors identify each subject's individual oxygen supply, vs. oxygen need center zone, or Energy Conversion Index (ECi) Zero. When a person is healthy, at rest or asleep, and breathing normally, the intake of oxygen by breathing can be considered to be a normal minimum amount for that person, and can also be described as a natural balance of minimum oxygen intake, vs. minimum oxygen need. This condition is further described herein as an ECi Zero condition; with not enough oxygen intake to meet the needs of the body, or cellular hypoxia condition, producing a negative ECi numeric trend less than zero, and more than enough oxygen intake, or cellular hyperoxia, producing a positive ECi numeric trend greater than zero.

The disclosed light-based sensors also use algorithmic analysis of the recorded data trend to produce a numeric offset value that, when subtracted from the 850 nm data, fine-tunes the output ECi data trend relative to the true ECi Zero value of the individual person during each session of use. This fine-tuning offset is needed for two reasons: (1) the sensor will most likely be placed on the skin when the person is not actually at the person's ECi Zero, and (2) even with 12-bit resolution on the illumination power levels, it is unlikely that the detected intensities can be brought closer than about 20 digitized intensity level steps to being exactly equal. In the application of sleep testing, the ECi Zero has been most consistently identifiable when the person awakens after having been asleep for at least 3 hours. This enables the fully relaxed and awake person to breathe without airway obstruction or central apnea; thus, likely bringing total body physiology to its optimum resting level. Other applications will likely need to perform ensemble averaging of the ECi trend during periods of apparent minimal activity to scan for a period when the body is most likely to be at ECi Zero status; then define the offset value needed to bring the data recorded during that minimal activity period to center on zero. Once so determined, the offset value is used to offset the entire recording session to center on the most likely current ECi Zero of the person. Experimental experience indicates that ECi Zero is not to be taken as the optimal health status of the person, but rather to establish a convenient and reproduceable ECi value reference point in the person's cellular chemistry continuum. Since light absorption in the skin is due to many thousands of different kinds of molecules within the light path, the sensor cannot be calibrated, in the usual sense, to a single reference molecule, such as hemoglobin is used to calibrate pulse oximeter sensors. Experimental evidence has, however, established that the cellular oxygen supply-related continuum can be usefully sensed and portrayed by referencing the disclosed sensors to a balanced minimum oxygen need, vs. oxygen supply condition, which we call ECi Zero.

An aspect of the disclosure is directed to Energy Conversion Monitor (ECM) sensors. Suitable ECM sensors comprise: a housing; a power source; a first light emitter positioned within an interior of the housing configured to emit a first light at a first wavelength; a second light emitter positioned within the interior of the housing configured to emit a second light at a second wavelength different than the first wavelength; a light detector positioned within the interior of the housing and optically isolated from the first light emitter and the second light emitter wherein the light detector is configured to detect a resulting first tissue-interacted light signal from the first light emitter and a second tissue-interacted light signal from the second light emitter; an illumination power control circuit in communication with the first light emitter and the second light emitter wherein the illumination power control circuit is configured to provide a computer program-defined illumination power to energize the first light emitter and the second light emitter at a respective computer program-defined illumination intensity; a signal amplifier in communication with the light detector; and a microcontroller configured to compute a first output data value from the first tissue-interacted light and a second output data from the second tissue-interacted light. In some configurations the ECM sensor uses a plurality of wavelengths of light selected by in vivo spectrometry. The plurality of wavelengths of light can be selected to maximize a respective variation in detected cellular light absorbance relative to at least one of a known cellular biochemical phenomenon and a known physiologic phenomenon affecting a monitored tissue. The first light emitter can have a first light emitter center wavelength value of from 675 nm to 695 nm inclusive. Additionally, the microcontroller is configurable to compensate during an initialization process for a variation in a skin pigmentation level by step-wise increasing a power delivered to the first light emitter up to a sustainable maximum rated power level for the first light emitter. If a detected intensity at 85% full scale is not detectable when the sustainable maximum rated power level for the first light emitter is reached, the microcontroller is configurable to implement an oversampling and mathematical integration method. Additionally, the microcontroller is configurable to increase a number of burst samples beyond a nominal number, sum all of the burst sample values, and divide the sum of all of the burst samples by the nominal number until a computed intensity value equal or greater than 85% full scale is achieved. The second light emitter can have a second light emitter center wavelength value of from 840 nm to 860 nm inclusive. The light detector can be configured to detect the first tissue-interacted light signal and the second tissue-interacted light signal at one or more timed intervals. Operation of the ECM sensors can be controlled by the user directly (i.e. by interfacing with the sensor) or via a software application on a mobile computing device such as a smart phone or tablet configured to wirelessly control the ECM sensor. In other configurations, the ECM sensors can be operated via a remote computing device which communicates wirelessly with the ECM sensor (e.g. from a clinic or healthcare practitioner facility).

Another aspect of the disclosure is directed to systems in communication with an ECM sensor. Suitable systems comprise: an Energy Conversion Monitor sensor comprising a housing, a power source, a first light emitter positioned within an interior of the housing configured to emit a first light at a first wavelength, a second light emitter positioned within the interior of the housing configured to emit a second light at a second wavelength different than the first intensity, a light detector positioned within the interior of the housing and optically isolated from the first light emitter and the second light emitter wherein the light detector is configured to detect a resulting first tissue-interacted light signal from the first light emitter and a second tissue-interacted light signal from the second light emitter, an illumination power control circuit in communication with the first light emitter and the second light emitter wherein the illumination power control circuit is configured to provide a computer program-defined illumination power to energize the first light emitter and the second light emitter at a respective computer program-defined illumination intensity, a signal amplifier in communication with the light detector, and a microcontroller configured to compute a first output data value from the first tissue-interacted light and a second output data from the second tissue-interacted light; and at least one secondary device. The secondary device can be selected from a second sensor, a sleep disordered breathing (SDB) therapy device, a remote computing device, and a polysomnograph (PSG) system. Additionally the system can be controlled by a software application which is in communication with the ECM sensor and one or more secondary device. Operation of the system can be controlled by the user directly (i.e. by interfacing with the sensor) or via a software application on a mobile computing device such as a smart phone or tablet configured to wirelessly control the system. In other configurations, the system can be operated via a remote computing device which communicates wirelessly with the devices of the system (e.g. from a clinic or healthcare practitioner facility).

Still another aspect of the disclosure is directed to methods of using an ECM sensor. Suitable methods comprise the steps of: applying an Energy Conversion Monitor sensor to a skin surface of a patient wherein the Energy Conversion Monitor sensor comprises a housing, a power source, a first light emitter positioned within an interior of the housing configured to emit a first light at a first wavelength, a second light emitter positioned within the interior of the housing configured to emit a second light at a second wavelength different than the first wavelength, a light detector positioned within the interior of the housing and optically isolated from the first light emitter and the second light emitter wherein the light detector is configured to detect a resulting first tissue-interacted light signal from the first light emitter and a second tissue-interacted light signal from the second light emitter, an illumination power control circuit in communication with the first light emitter and the second light emitter wherein the illumination power control circuit is configured to provide a computer program-defined illumination power to energize the first light emitter and the second light emitter at a respective computer program-defined illumination intensity, a signal amplifier in communication with the light detector, and a microcontroller configured to compute a first output data value from the first tissue-interacted light and a second output data from the second tissue-interacted light; and powering the Energy Conversion Monitor sensor. In some configurations, the method can also comprise the steps of: delivering a power level to the Energy Conversion Monitor sensor to equalize a first detected intensity of light at a first wavelength between 675 nm and 695 nm inclusive with a second detected intensity of light at a second wavelength between 840 nm and 860 nm inclusive; determining a first detected intensity of light from a first tissue interacted light signal; determining a second detected intensity of light from a second tissue interacted light signal; comparing the first detected intensity of light to a first full scale to determine a first percentage detected intensity of light; comparing the second detected intensity of light to a second full scale to determine a second percentage detected intensity of light; and repeating the delivering, determining, and comparing steps to obtain a detected intensity of light at 85% of full scale for each of the first detected intensity of light and the second detected intensity of light. Additionally, the methods can comprise storing the power level and a total number of burst samples added together and divided by a nominal number of burst samples to achieve a detected, integrated intensity of tissue interacted light from the first emitter of 85% full scale in a memory, and storing the power level to achieve a detected intensity of tissue interacted light from the second emitter of 85% full scale in a memory. In some configurations, the methods can comprise using the stored power level of a first emitter and the number of burst samples of detected tissue interacted light from a first emitter, and the stored power level of a second emitter, as control parameters in data acquisition through a current recording session. In some configurations, the methods can comprise initializing the Energy Conversion Monitor sensor; subtracting a detected intensity from the second light emitter (between 840 nm and 860 nm inclusive), following tissue interaction with a second light, from the detected intensity from the first light emitter (between 675 nm and 695 nm inclusive), following tissue interaction with a first light, to produce an Energy Conversion Index (ECi) output as an at least 12-bit resolution; and generating an integer numeric value analog indication of a status of cellular oxygen supply-related chemistry. Still other configurations can include a method comprising computing one of a cellular oxygen supply-related center and an Energy Conversion Index Zero (ECi Zero) of a user; and applying an offset value to a center the data output of an Energy Conversion Monitor sensor output data. Yet other methods can comprise performing a calculation averaging a period of low activity to define and record an offset numeric value relative to zero; determining a current ECi Zero for a patient; and applying a recorded offset numeric value to center the recorded data on a current ECi Zero of the patient. In some configurations of the method it may be advantageous for the method to also comprise one or more steps of indicating, in response to an ECi data less than zero produced by decreased detected intensity at 685 nm along with simultaneous stable detected intensity at 850 nm, a cellular oxygen supply less than physiologically optimum; indicating, in response to an ECi data greater than zero produced by stable or increased detected first intensity between 675 nm and 695 nm inclusive along with simultaneous stable or decreased second detected intensity between 840 nm and 860 nm inclusive, a cellular oxygen supply more than physiologically optimum; and identifying an indication of changing blood volume beneath the Energy Conversion Monitor sensor resulting from at least one of an Energy Conversion Monitor sensor motion against the skin and a change of body position vs. gravity during sleep causing a tandem variation in a first detected light intensity between 675 nm and 695 nm inclusive and a second detected light intensity between 840 nm and 860 nm inclusive. Some methods also comprise the steps of generating a generated signal between 840 nm and 860 nm inclusive; and detecting the generated signal at a sufficiently frequent timed interval to define an amplitude and a waveform of a breathing-induced, light intensity variation as an indication of one of an increased effort to breathe through a restricted or obstructed airway, and a decreased or absent effort to breathe from a reduced or absent central nervous system breathing drive.

Yet another aspect of the disclosure is directed to methods of using an ECM sensor in specific clinical scenarios. For example, the methods of using the ECM sensor can also comprise: applying the Energy Conversion Monitor sensor on a person identified as possibly suffering from sleep disordered breathing (SDB); monitoring breathing and oxygen supply-related physiology during sleep of the person; and providing recorded data from the monitoring to aid in clinical diagnosis of SDB to help define, validate, and regulate effective therapy. In another clinical method, the method can comprise applying the Energy Conversion Monitor sensor to a person having sleep disordered breathing (SDB) while sleeping at home while using an SDB therapy device; and determining an extent of management of the SDB. Still another method can comprise: applying the Energy Conversion Monitor sensor to a person while sleeping at home while using a sleep disordered breathing (SDB) therapy device to provide ECi and breathing information to the SDB therapy device; controlling the SBD therapy device in response to at least one of the ECi and breathing information from the Energy Conversion Monitor sensor; and providing surveillance during sleep for changes in the person's general health status. Additional methods comprise: applying the Energy Conversion Monitor sensor on a person identified as at risk of developing sepsis; and detecting the possible presence of sepsis as from an ECi value progressively trending less than zero. Another method also comprises applying the Energy Conversion Monitor sensor to an infant; screening the infant for a risk of SIDS by recording a stability and effectiveness of breathing during sleep. Yet another method comprises applying the Energy Conversion Monitor sensor to an infant; monitoring a stability and effectiveness of breathing during sleep; and one or more of delivering a stimulation to arouse the infant from sleep during episodes of detected abnormal breathing during sleep, and delivering an alarm identifying the detected abnormal breathing to a caregiver. Yet another method comprises applying the Energy Conversion Monitor sensor to a newborn infant; and providing feedback to a caregiver for use in regulating an oxygen level in a breathing gas relative to a cellular oxygen need as the infant transitions from fetal life to a higher level of oxygen available from breathing air, or higher levels of oxygen, to help reduce or prevent oxygen supply-related injuries. Another method comprises applying the Energy Conversion Monitor sensor during a resuscitation of a person suffering from at least one of hypoxia and suffocation; and guiding a regulation of oxygen in a breathing gas relative to a cellular oxygen need of the person. Another method comprises applying the Energy Conversion Monitor sensor to a worker in a high-risk atmospheric environment; and monitoring the worker for at least one of hypoxia and adverse effects of toxic gases in their breathing air. Yet another method comprises applying the Energy Conversion Monitor sensor to a forehead of a pilot; and monitoring the pilot for one or more of hypoxia and a g-load-induced loss of blood flow to the head. Still another method comprises applying the Energy Conversion Monitor sensor to an athlete during and following physical exercise; assessing physiologic responses of the athlete; and providing a recommendation for optimum performance. Another method comprises applying the Energy Conversion Monitor sensor having a dual probe to a chest and abdomen of an infant patient in intensive care; monitoring a pre-ductal cellular oxygen supply and a post-ductal cellular oxygen supply; and detecting at least one of an anatomic anomaly of a heart, an anatomic anomaly of a great vessels, and a failure of a ductus arteriosus to close normally. Yet another method comprises applying the Energy Conversion Monitor sensor having a dual probe during at least one of reperfusion of a myocardium during therapy for ischemic heart attack, reperfusion of an affected area of a brain during therapy for a stroke, a reperfusion of a transplant organ, and a guide oxygen resupply to the ischemic tissue relative to cellular oxygen need to help reduce or prevent reperfusion injury.

Another aspect of the disclosure is directed to Energy Conversion Monitor (ECM) sensors. Suitable ECM sensors comprise: a housing means; a power source means; a first light emitter means positioned within an interior of the housing means configured to emit a first light at a first wavelength; a second light emitter means positioned within the interior of the housing means configured to emit a second light at a second wavelength different than the first wavelength; a light detector means positioned within the interior of the housing means and optically isolated from the first light emitter means and the second light emitter means wherein the light detector means is configured to detect a resulting first tissue-interacted light signal from the first light emitter means and a second tissue-interacted light signal from the second light emitter means; an illumination power control circuit means in communication with the first light emitter means and the second light emitter means wherein the illumination power control circuit means is configured to provide a computer program-defined illumination power to energize the first light emitter means and the second light emitter means at a respective computer program-defined illumination intensity; a signal amplifier means in communication with the light detector means; and a microcontroller means configured to compute a first output data value from the first tissue-interacted light and a second output data from the second tissue-interacted light. In some configurations the ECM sensor uses a plurality of wavelengths of light selected by in vivo spectrometry. The plurality of wavelengths of light can be selected to maximize a respective variation in detected cellular light absorbance relative to at least one of a known cellular biochemical phenomenon and a known physiologic phenomenon affecting a monitored tissue. The first light emitter means can have a first light emitter means center wavelength value of from 675 nm to 695 nm inclusive. Additionally, the microcontroller means is configurable to compensate during an initialization process for a variation in a skin pigmentation level by step-wise increasing a power delivered to the first light emitter means up to a sustainable maximum rated power level for the first light emitter means. If a detected intensity at 85% full scale is not detectable when the sustainable maximum rated power level for the first light emitter means is reached, the microcontroller means is configurable to implement an oversampling and mathematical integration method. Additionally, the microcontroller means is configurable to increase a number of burst samples beyond a nominal number, sum all of the burst sample values, and divide the sum of all of the burst samples by the nominal number until a computed intensity value equal or greater than 85% full scale is achieved. The second light emitter means can have a second light emitter means center wavelength value of from 840 nm to 860 nm inclusive. The light detector means can be configured to detect the first tissue-interacted light signal and the second tissue-interacted light signal at one or more timed intervals. Operation of the ECM sensors can be controlled by the user directly (i.e. by interfacing with the sensor) or via a software application on a mobile computing device such as a smart phone or tablet configured to wirelessly control the ECM sensor. In other configurations, the ECM sensors can be operated via a remote computing device which communicates wirelessly with the ECM sensor (e.g. from a clinic or healthcare practitioner facility).

Another aspect of the disclosure is directed to systems in communication with an ECM sensor. Suitable systems comprise: an Energy Conversion Monitor sensor comprising a housing means, a power source means, a first light emitter means positioned within an interior of the housing means configured to emit a first light at a first wavelength, a second light emitter means positioned within the interior of the housing means configured to emit a second light at a second wavelength different than the first intensity, a light detector means positioned within the interior of the housing means and optically isolated from the first light emitter means and the second light emitter means wherein the light detector means is configured to detect a resulting first tissue-interacted light signal from the first light emitter means and a second tissue-interacted light signal from the second light emitter means, an illumination power control circuit means in communication with the first light emitter means and the second light emitter means wherein the illumination power control circuit means is configured to provide a computer program-defined illumination power to energize the first light emitter means and the second light emitter means at a respective computer program-defined illumination intensity, a signal amplifier means in communication with the light detector means, and a microcontroller means configured to compute a first output data value from the first tissue-interacted light and a second output data from the second tissue-interacted light; and at least one secondary device. The secondary device can be selected from a second sensor, a sleep disordered breathing (SDB) therapy device, a remote computing device, and a polysomnograph (PSG) system. Additionally the system can be controlled by a software application which is in communication with the ECM sensor and one or more secondary device. Operation of the system can be controlled by the user directly (i.e. by interfacing with the sensor) or via a software application on a mobile computing device such as a smart phone or tablet configured to wirelessly control the system. In other configurations, the system can be operated via a remote computing device which communicates wirelessly with the devices of the system (e.g. from a clinic or healthcare practitioner facility).

Still another aspect of the disclosure is directed to methods of using an ECM sensor. Suitable methods comprise the steps of: applying an Energy Conversion Monitor sensor to a skin surface of a patient wherein the Energy Conversion Monitor sensor comprises a housing means, a power source means, a first light emitter means positioned within an interior of the housing means configured to emit a first light at a first wavelength, a second light emitter means positioned within the interior of the housing means configured to emit a second light at a second wavelength different than the first wavelength, a light detector means positioned within the interior of the housing means and optically isolated from the first light emitter means and the second light emitter means wherein the light detector means is configured to detect a resulting first tissue-interacted light signal from the first light emitter means and a second tissue-interacted light signal from the second light emitter means, an illumination power control circuit means in communication with the first light emitter means and the second light emitter means wherein the illumination power control circuit means is configured to provide a computer program-defined illumination power to energize the first light emitter means and the second light emitter means at a respective computer program-defined illumination intensity, a signal amplifier means in communication with the light detector means, and a microcontroller means configured to compute a first output data value from the first tissue-interacted light and a second output data from the second tissue-interacted light; and powering the Energy Conversion Monitor sensor. In some configurations, the method can also comprise the steps of: delivering a power level to the Energy Conversion Monitor sensor to equalize a first detected intensity of light at a first wavelength between 675 nm and 695 nm inclusive with a second detected intensity of light at a second wavelength between 840 nm and 860 nm inclusive; determining a first detected intensity of light from a first tissue interacted light signal; determining a second detected intensity of light from a second tissue interacted light signal; comparing the first detected intensity of light to a first full scale to determine a first percentage detected intensity of light; comparing the second detected intensity of light to a second full scale to determine a second percentage detected intensity of light; and repeating the delivering, determining, and comparing steps to obtain a detected intensity of light at 85% of full scale for each of the first detected intensity of light and the second detected intensity of light. Additionally, the methods can comprise storing the power level and a total number of burst samples added together and divided by a nominal number of burst samples to achieve a detected, integrated intensity of tissue interacted light from the first emitter of 85% full scale in a memory, and storing the power level to achieve a detected intensity of tissue interacted light from the second emitter of 85% full scale in a memory. In some configurations, the methods can comprise using the stored power level of a first emitter and the number of burst samples of detected tissue interacted light from a first emitter, and the stored power level of a second emitter, as control parameters in data acquisition through a current recording session. In some configurations, the methods can comprise initializing the Energy Conversion Monitor sensor; subtracting a detected intensity from the second light emitter means (between 840 nm and 860 nm inclusive), following tissue interaction with a second light, from the detected intensity from the first light emitter means (between 675 nm and 695 nm inclusive), following tissue interaction with a first light, to produce an Energy Conversion Index (ECi) output as an at least 12-bit resolution; and generating an integer numeric value analog indication of a status of cellular oxygen supply-related chemistry. Still other configurations can include a method comprising computing one of a cellular oxygen supply-related center and an Energy Conversion Index Zero (ECi Zero) of a user; and applying an offset value to a center the data output of an Energy Conversion Monitor sensor output data. Yet other methods can comprise performing a calculation averaging a period of low activity to define and record an offset numeric value relative to zero; determining a current ECi Zero for a patient; and applying a recorded offset numeric value to center the recorded data on a current ECi Zero of the patient. In some configurations of the method it may be advantageous for the method to also comprise one or more steps of indicating, in response to an ECi data less than zero produced by decreased detected intensity at 685 nm along with simultaneous stable detected intensity at 850 nm, a cellular oxygen supply less than physiologically optimum; indicating, in response to an ECi data greater than zero produced by stable or increased detected first intensity between 675 nm and 695 nm inclusive along with simultaneous stable or decreased second detected intensity between 840 nm and 860 nm inclusive, a cellular oxygen supply more than physiologically optimum; and identifying an indication of changing blood volume beneath the Energy Conversion Monitor sensor resulting from at least one of an Energy Conversion Monitor sensor motion against the skin and a change of body position vs. gravity during sleep causing a tandem variation in a first detected light intensity between 675 nm and 695 nm inclusive and a second detected light intensity between 840 nm and 860 nm inclusive. Some methods also comprise the steps of generating a generated signal between 840 nm and 860 nm inclusive; and detecting the generated signal at a sufficiently frequent timed interval to define an amplitude and a waveform of a breathing-induced, light intensity variation as an indication of one of an increased effort to breathe through a restricted or obstructed airway, and a decreased or absent effort to breathe from a reduced or absent central nervous system breathing drive.

Yet another aspect of the disclosure is directed to methods of using an ECM sensor in specific clinical scenarios. For example, the methods of using the ECM sensor can also comprise: applying the Energy Conversion Monitor sensor on a person identified as possibly suffering from sleep disordered breathing (SDB); monitoring breathing and oxygen supply-related physiology during sleep of the person; and providing recorded data from the monitoring to aid in clinical diagnosis of SDB to help define, validate, and regulate effective therapy. In another clinical method, the method can comprise applying the Energy Conversion Monitor sensor to a person having sleep disordered breathing (SDB) while sleeping at home while using an SDB therapy device; and determining an extent of management of the SDB. Still another method can comprise: applying the Energy Conversion Monitor sensor to a person while sleeping at home while using a sleep disordered breathing (SDB) therapy device to provide ECi and breathing information to the SDB therapy device; controlling the SBD therapy device in response to at least one of the ECi and breathing information from the Energy Conversion Monitor sensor; and providing surveillance during sleep for changes in the person's general health status. Additional methods comprise: applying the Energy Conversion Monitor sensor on a person identified as at risk of developing sepsis; and detecting the possible presence of sepsis as from an ECi value progressively trending less than zero. Another method also comprises applying the Energy Conversion Monitor sensor to an infant; screening the infant for a risk of SIDS by recording a stability and effectiveness of breathing during sleep. Yet another method comprises applying the Energy Conversion Monitor sensor to an infant; monitoring a stability and effectiveness of breathing during sleep; and one or more of delivering a stimulation to arouse the infant from sleep during episodes of detected abnormal breathing during sleep, and delivering an alarm identifying the detected abnormal breathing to a caregiver. Yet another method comprises applying the Energy Conversion Monitor sensor to a newborn infant; and providing feedback to a caregiver for use in regulating an oxygen level in a breathing gas relative to a cellular oxygen need as the infant transitions from fetal life to a higher level of oxygen available from breathing air, or higher levels of oxygen, to help reduce or prevent oxygen supply-related injuries. Another method comprises applying the Energy Conversion Monitor sensor during a resuscitation of a person suffering from at least one of hypoxia and suffocation; and guiding a regulation of oxygen in a breathing gas relative to a cellular oxygen need of the person. Another method comprises applying the Energy Conversion Monitor sensor to a worker in a high-risk atmospheric environment; and monitoring the worker for at least one of hypoxia and adverse effects of toxic gases in their breathing air. Yet another method comprises applying the Energy Conversion Monitor sensor to a forehead of a pilot; and monitoring the pilot for one or more of hypoxia and a g-load-induced loss of blood flow to the head. Still another method comprises applying the Energy Conversion Monitor sensor to an athlete during and following physical exercise; assessing physiologic responses of the athlete; and providing a recommendation for optimum performance. Another method comprises applying the Energy Conversion Monitor sensor having a dual probe to a chest and abdomen of an infant patient in intensive care; monitoring a pre-ductal cellular oxygen supply and a post-ductal cellular oxygen supply; and detecting at least one of an anatomic anomaly of a heart, an anatomic anomaly of a great vessels, and a failure of a ductus arteriosus to close normally. Yet another method comprises applying the Energy Conversion Monitor sensor having a dual probe during at least one of reperfusion of a myocardium during therapy for ischemic heart attack, reperfusion of an affected area of a brain during therapy for a stroke, a reperfusion of a transplant organ, and a guide oxygen resupply to the ischemic tissue relative to cellular oxygen need to help reduce or prevent reperfusion injury.

INCORPORATION BY REFERENCE

All publications, patents, and patent applications mentioned in this specification are herein incorporated by reference to the same extent as if each individual publication, patent, or patent application was specifically and individually indicated to be incorporated by reference. References include, for example:
US 2006/0009685 A1 to Finarov et al. published Jan. 12, 2006 for Device and Method for Non-Invasive Optical Measurements;
US 2008/0081966 A1 to Debreczeny published Apr. 3, 2008 for Symmetric LED Array for Pulse Oximetry;
US 2008/0208009 A1 to Shklarski published Aug. 28, 2008 for Wearable Device, System and Method for Measuring Vital Parameters;
US 2010/0324390 A1 to McLaughlin, published Dec. 23, 2010, for Measurement of Oxygen Saturation of Blood Haemoglobin;
US 2011/0054336 A1 to Jornod published Mar. 3, 2011 for Method and Device for Measuring the Pulse by Means of Light Waves with Two Wavelengths;
US 2013/0303921 A1 to Chu, published Nov. 14, 2013, for System and Method for Measurement of Physiological Data with Light Modulation;
US 2013/0317331 A1 to Bechtel, published Nov. 28, 2013, for Monte Carlo and Iterative Methods for Determination of Tissue Oxygen Saturation;
US 2014/0275888 A1 to Wegerich published Sep. 18, 2014 for Wearable Wireless Multisensor Health Monitor with Heat Photoplethysmograph;
US 2015/0011854 A1 to Frix, published Jan. 8, 2015, for Continuous Transdermal for "Signal Monitoring System and Method; Including EMI-Shielding Coupler," CAS Medical Systems, Inc.;

US 2015/0057511 A1 to Basu, published Feb. 26, 2015, for Sensor and Method for Continuous Health Monitoring;

US 2017/0049336 A1 to Hatch for Physiological Sensors, Systems, Kits and Methods Therefor published Feb. 23, 2017;

US 2017/0112422A1 to Hatch for Optical Physiologic Sensors and Methods published Apr. 27, 2017; and U.S. Pat. No. 5,830,137 A to Scharf issued Nov. 3, 1998 for Green Light Pulse Oximeter;

U.S. Pat. No. 6,801,799 B2 to Mendelson, issued Oct. 5, 2004, for Pulse Oximeter and Method of Operation;

U.S. Pat. No. 7,691,067 B2 to Westbrook, issued Apr. 6, 2010, for Method for Measuring Central Venous Pressure or Respiratory Effort;

U.S. Pat. No. 7,738,935 B1 to Turcott, issued Jun. 15, 2010, for Methods and Devices for Reduction of Motion-Induced Noise in Pulse Oximetry;

U.S. Pat. No. 8,073,516 B2 to Scharf issued Dec. 6, 2011, for Separating Motion from Cardiac Signals Using Second Order Derivative of the Photo-Plethysmogram and Fast Fourier Transforms;

U.S. Pat. No. 8,133,176 B2 to Porges, issued Mar. 13, 2012, for Method and Circuit for Indicating Quality and Accuracy of Physiological Measurements;

U.S. Pat. No. 8,346,327 B2 to Campbell, issued Jan. 1, 2013, for Method for Identification of Sensor Site by Local Skin Spectrum Data;

U.S. Pat. No. 9,125,563 B2 for "Signal Monitoring System Including EMI-Shielding Coupler," CAS Medical Systems, Inc., Sep. 8, 2015;

U.S. Pat. No. 9,357,954 B2 for "Simultaneous Measurement of Pulse and Regional Blood Oxygen Saturation," Covidien LP, issued Jun. 7, 2016;

U.S. Pat. No. 10,327,710 B2 for "Age Calibration for Tissue Oximetry," Nonin Medical, Inc., issued Jun. 25, 2019;

U.S. Pat. No. 10,335,072 B2 for "Physiologic Monitor," Masimo Corporation, issued Jul. 2, 2019;

U.S. Pat. No. 10,369,310 B2 for "Method and Apparatus for Treatment of Respiratory Disorders" ResMed Limited issued Aug. 6, 2019;

U.S. Pat. No. 10,376,670 B2 for "Methods and Systems for Sleep Management" ResMed Sensor Technologies issued Aug. 13, 2019;

U.S. Pat. No. 10,383,569 B2 for "Mechanical Ventilation in the Presence of Sleep Disordered Breathing" ResMed Limited, issued Aug. 20, 2019;

WO 2015/168235 A1 to Hatch published Nov. 5, 2015, for Physiological Sensors, Systems, Kits and Methods Therefor;

Cornet A D, et. al., The potential harm of oxygen therapy in medical emergencies," Critical Care 2013, 17:313, PMID: 23635028;

Hashimoto I, et. al., "The features of thrombus in a microvessel injury model and the antithrombotic efficacy of heparin, urokinase, and prostaglandin E1," Plastic and Reconstructive Surgery, June 2003, 2307-2314;

Hunt C, et. al., "Cardiorespiratory events detected by home memory monitoring and one-year neurodevelopmental outcome," J Pediatr 2004; 145:465-71, PMID: 15480368;

Hyttel-Sorensen S, et. al. "Peripheral tissue oximetry: comparing three commercial near-infrared spectroscopy oximeters on the forearm," J Clin Monit Computer (2014) 28:149-155, PMID: 23990288;

Joosen S A, et. al., "Dynamic loop gain increases upon adopting the supine body position during sleep in patients with obstructive sleep apnea," Respirology 2017 November; 22(8): 1662-1669, PMID: 28730724;

Kalogeris T, et. al., "Ischemia/Reperfusion," Comprehensive Physiology 7:113-170, 2017, PMID: 28135002;

Liegl R, et. al., "Retinopathy of prematurity: the need for prevention," Eye and Brain 2016:8 91-102, PMID: 28539604;

Lopez S, "Pulse Oximeter Fundamentals and Design," Document Number: AN4327, Rev. 2, 11/20/12, Freescale Semiconductor Application Note;

Mayevsky A, et. al., "Mitochondrial function and tissue vitality: bench-to-bedside real-time optical monitoring system," J Biomedical Optics, 16(6), 067004, June 2017, PMID: 21721825;

Miller, et. al., "Antenatal antioxidant treatment with melatonin to decrease newborn neurodevelopmental deficits and brain injury caused by fetal growth restriction," J Pineal Res 2014 April: 56(3): 283-94, PMID: 24456220;

Okuno, et. al., "Rotation and structure of Fo and F1-ATP synthase," J. Biochem. 2011; 149(6):655-664, PMID: 21524994;

Ramanathan R, et. al., "Cardiorespiratory events recorded on home monitors: comparison of healthy infants with those at increased risk for SIDS," JAMA, May 2, 2001, Vol. 285, No. 17, 2199-2207, PMID: 15480368;

Rolfe P, "In vivo near-infrared spectroscopy," Annu. Rev. Biomed. Eng. 2000 02:715-54, PMID: 11701529; and Rozova E V, et. al., "Structural and dynamic changes in mitochondria of rat myocardium under acute hypoxic hypoxia: role of mitochondrial ATP-dependent potassium channel," Biochemistry (Moscow) 2015, Vol. 89, No. 8, pp. 994-1000, PMID: 26547067.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 9A-E illustrate sleep recording segments showing when and in which direction ECi data can be used to trigger APAP changes in airway pressure;

FIGS. 11A-B illustrate exemplar graphs of ischemia/reperfusion spectral absorption test results taken from a spectrometer recording;

FIGS. 15C-D illustrate exemplar graphs of a segment of FIGS. 15A-B during restricted and periodic breathing taken from the sensor monitoring device;

DETAILED DESCRIPTION

Figure 1A:
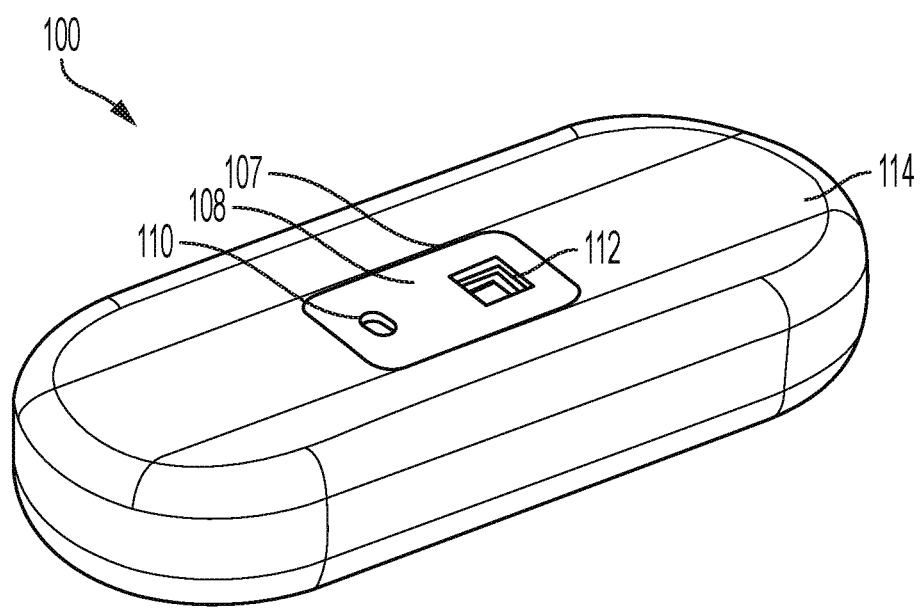
FIGS. 1A-D illustrate an exemplar sensor device.

The ECM sensor 100 is portrayed in FIG. 1A. An exterior surface 108 of a sensor aperture component 107 comes in contact with the patient's skin. A light emitter aperture opening 110 and a light detector aperture opening 112 are provided which can be filled with clear plastic potting to present a flat surface to the patient's skin, when applied. A plastic resin encapsulation 114 housing hermetically encloses and mechanically protects the internal components of the ECM sensor 100 device.

Figure 1B:
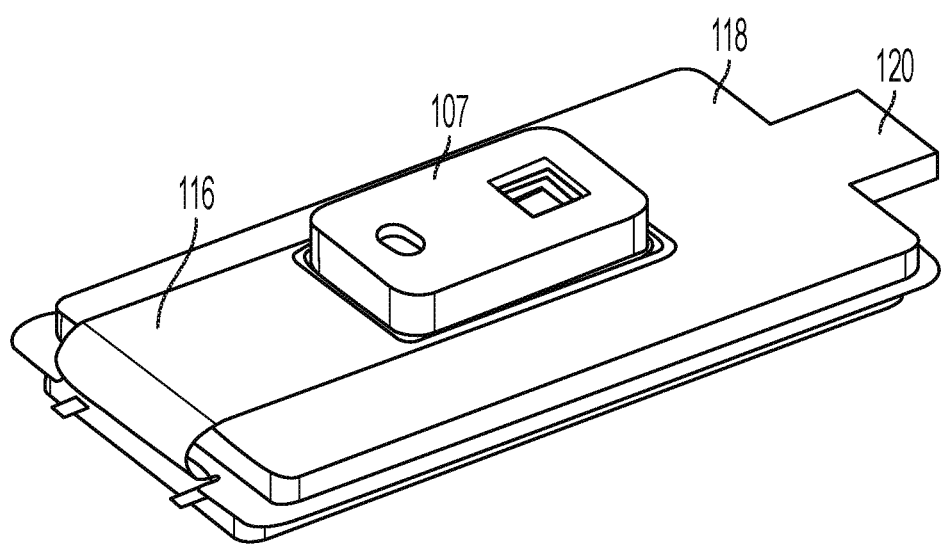

FIG. 1B shows internal components of the ECM sensor 100 shown in FIG. 1A. As shown, the sensor aperture component 107 has a length, height and width and is adhered to an end of a flexible circuit 116. A component volume space for surface mount technology (SMT) components is illustrated which is mounted on a main printed circuit board (PCB) portion of the main circuit 118. The flexible circuit 116 is configurable to fold over the SMT components. Additional electronic components, such as a BluetoothLE® transceiver 120, and a, optionally, a vibrator motor for haptic stimulation, can also be mounted to the main circuit 118.

Figure 1C:
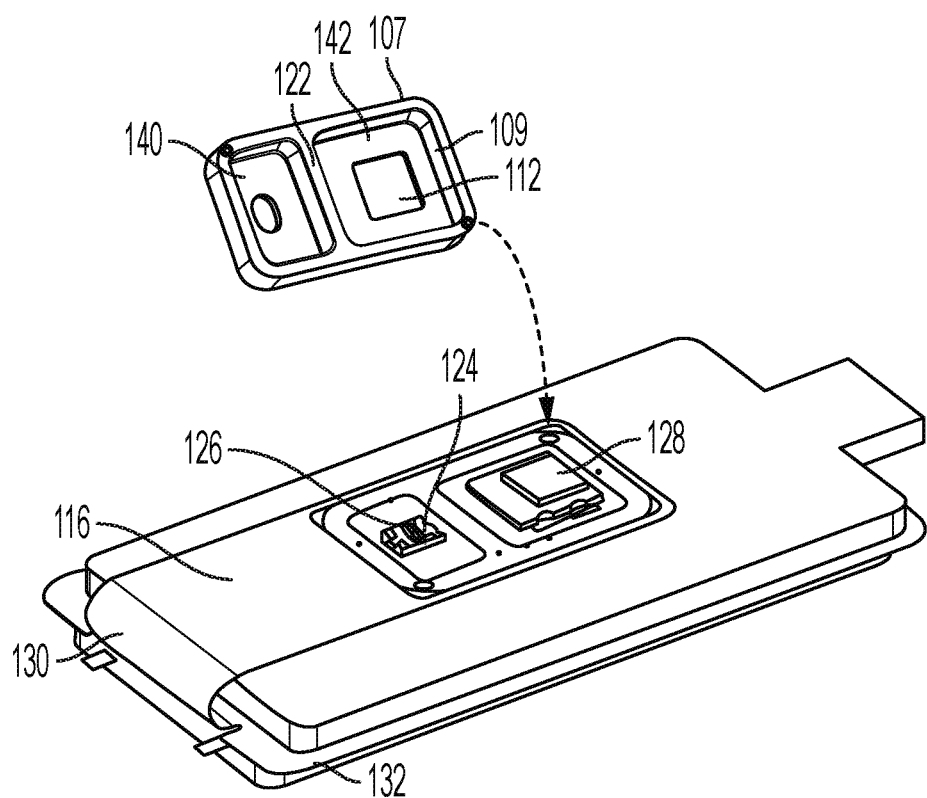

FIG. 1C shows the sensor aperture component 107 removed from over the light emitting diodes (LEDs) 124 and 126 and detector 128, such as a photodiode detector. An interior surface 109 of the sensor aperture component 107 is shown. The sensor aperture component 107 has at least one internal wall 122 that, when secured to the flexible circuit 116, provides an optical barrier between a first chamber 140 and a second chamber 142. The first chamber 140 (light emitter cavity) and the second chamber 142 (detector cavity) define three-dimensional (3D) recesses on the interior surface 109 of the sensor aperture component 107. Use of metal for the sensor aperture component 107 can be used in one configuration. However, as will be appreciated by those skilled in the art, a plastic material that is sufficiently opaque to both red and infrared light could also be used to form the sensor aperture component 107, including the internal wall light barrier. Additionally, the sensor aperture component 107 can be attachable, e.g. with a suitable adhesive, such as epoxy.

A red LED 124, an infrared LED 126, and a detector 128, such as a silicon photodiode, are mountable on the flexible circuit 116. LED power control and signal amplifier components are mounted on the underside of the sensor portion of the flexible circuit 116. The flexed portion 130 of the flexible circuit 116 carries circuit traces from the sensor to the main circuit 132.

As will be appreciated by those skilled in the art, the actual layout can take a variety of forms without departing from the scope of the disclosure. In some configurations, the lead pattern of the microcontroller can have a pattern that radiates in a plurality of directions. Thus, if the LEDs and sensors are placed in the middle, the microcontroller leads would need to be routed around the LEDs and sensors. By placing the optical components on a flexible circuit, as illustrated, a simplified layout is achieved. However, in some configurations, the Bluetooth transceiver may have an associated microcontroller that is capable of doing performing the optical component control, which would allow a sensor positioned in the center.

Figure 1D:
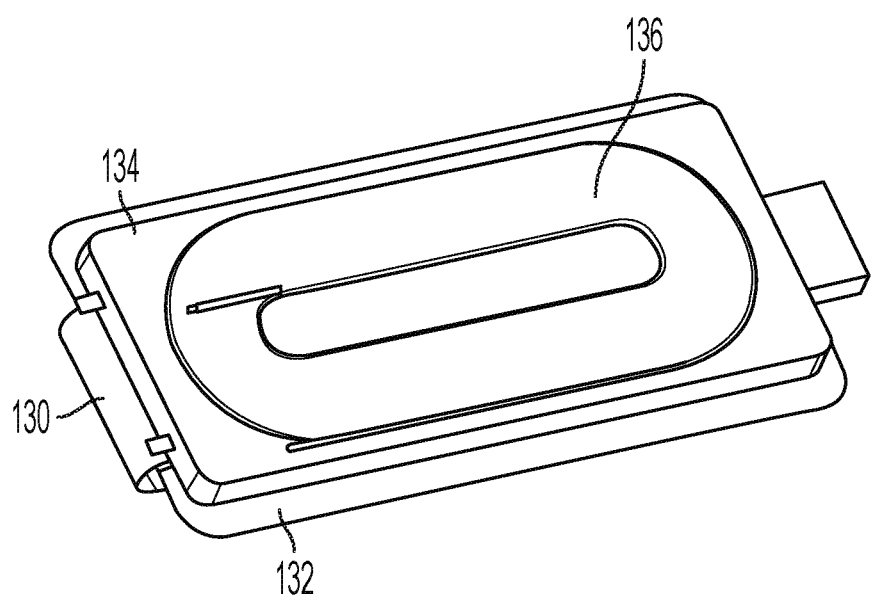

FIG. 1D illustrates the underside of the main circuit 132, where a battery 134 and battery recharging coil 136 are located with the flexed portion 130 and the optical component portion of the flexible circuit 116 curving around an end of the main circuit 132.

Figure 2:
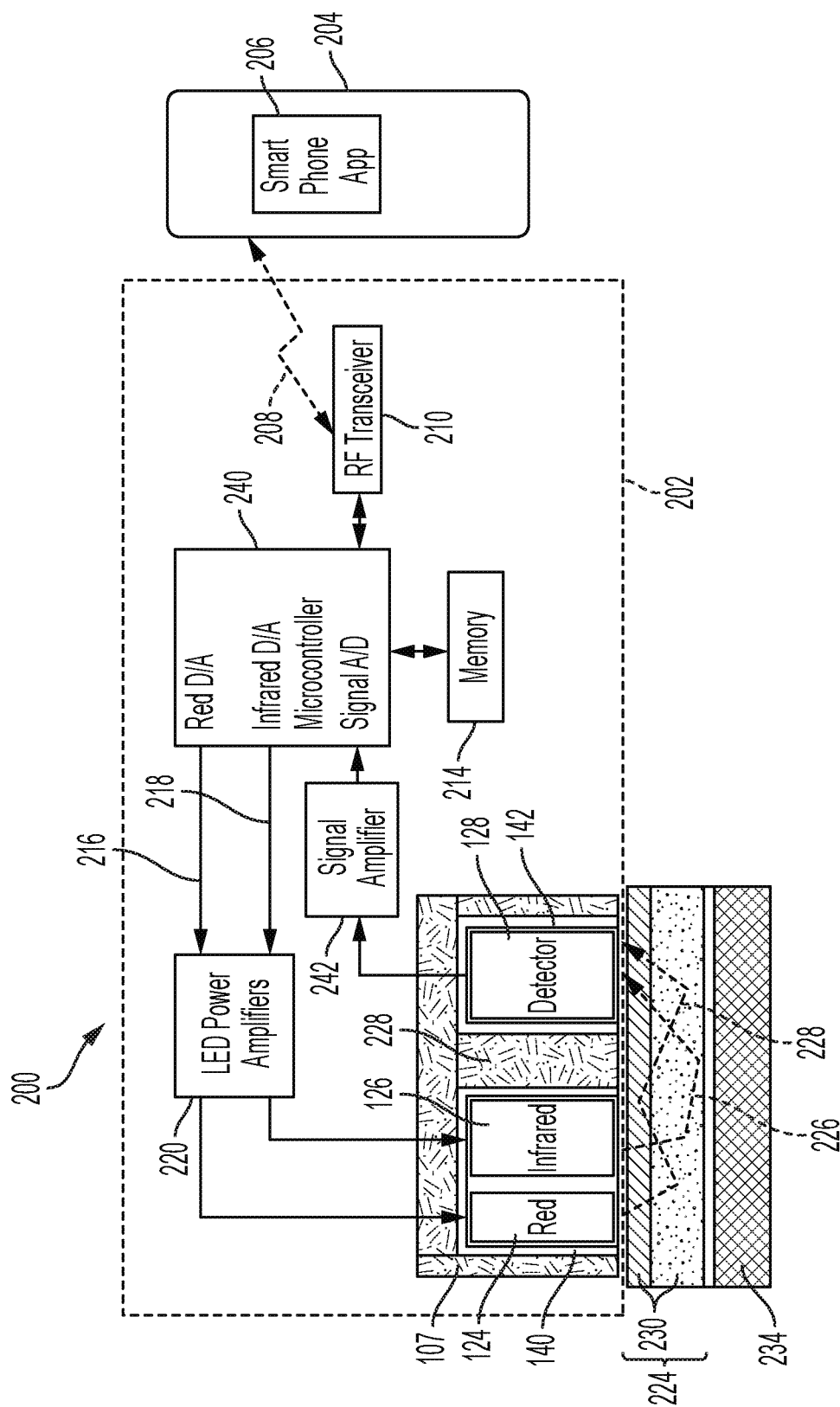
FIG. 2 is an exemplar schematic architecture for the sensor monitoring device system.

FIG. 2 is a schematic block diagram of the ECM sensor 200 on a test subject's skin, including the ECM sensor system 202 and a computer-implemented software application ("app") 206 operating on a smartphone 204. Sensor control commands and data transfer 208 between the ECM sensor system 202 and the smartphone 204 are managed via RF transceiver 210 in the ECM sensor system 202 and the BluetoothLE® RF transceiver and application program 206 operating in either an iPhone® or Android® OS smartphone, or equivalent. The light emission electro-optics components of the sensor system are enclosed within the visible and infrared light-opaque metal or plastic sensor aperture component 107 and housed within a first chamber 140 in FIG. 1C housing a red LED 124 and an infrared LED 126. The red LED 124 and infrared LED 126 can further be encased together in clear plastic; thus, providing a path for light emission from the LEDs through a light emitter aperture opening 110 in FIG. 1A.

The sensor aperture component 107 has a second chamber 142, which houses a detector 128, such as a silicon photodiode, and can also be filled with optically clear plastic. The housing of the sensor aperture component 107 has an internal wall 122 positioned between the first chamber 140 and the second chamber 142, which divides the two chambers and blocks internal transmission of the light from the red LEDs 124 and infrared LEDs 126 to the detector 128. Thus, any light detected by the detector 128 occurs after the light has been transmitted through the skin.

The ECM sensor system 202, when in use, is placed on the skin 224 of the patient. Emitted light 226 and 228 passes through the epidermis and dermis 230 of the skin, but does not functionally penetrate the superficial facia or underlying muscle 234.

Top level operational commands are conveyed from the ECM sensor system 202 via data transfer 208, such as an RF transmission achieved with a BluetoothLE® transmission, from the application program 206, such as a smartphone app, to initiate sensor function. A sensor microcontroller 240, establishes an RF linkage procedure with the application program 206, then performs a sensor initialization procedure to establish the optimum power levels delivered to the LEDs. Upon completion of the initialization process, the sensor microcontroller 240 performs data acquisition cycles at the time intervals set by the application program 206, which is 1 Hz for the 685 nm and 850 nm LEDs for ECi monitoring, plus additional illuminations of only the 850 nm LED, up to a total of 10 Hz, for monitoring breathing. During each ECi data acquisition cycle, an ambient light (i.e. not illuminated by either LED), a red LED-illuminated, and an infrared LED-illuminated detected light measurement are made and stored in the sensor memory 214. Current data is then communicated as raw data via the data transfer 208, such as an RF transceiver linkage, to the application program 206 for recording, display, and analysis.

An LED power amplifier 220 receives a D/A analog control voltage from the sensor microcontroller 240. The LED power amplifier 220 then sends the corresponding current level to the red LED 124 and/or the infrared LED 126. The detector 128 is in communication with a signal amplifier 242 which is in communication with the sensor microcontroller 240. The sensor microcontroller 240 is also in communication with a sensor memory 214 and an RF transceiver 210.

In another configuration, the ECM sensor 200 communicates directly or indirectly with an airway therapy device, such as an APAP machine or a CPAP machine. Data from the ECM sensor 200, provided directly or indirectly to the airway therapy device can be processed by the airway therapy device to result in a change of the administered airway therapy (e.g., air pressure). The direct submission of data can be wired or wireless. The indirect submission of data can be via a secondary device, such as a smartphone, or via a remote central station that processes the data received from the ECM sensor prior to delivering the processed data or machine operation commands to the airway therapy device.

Figure 3:
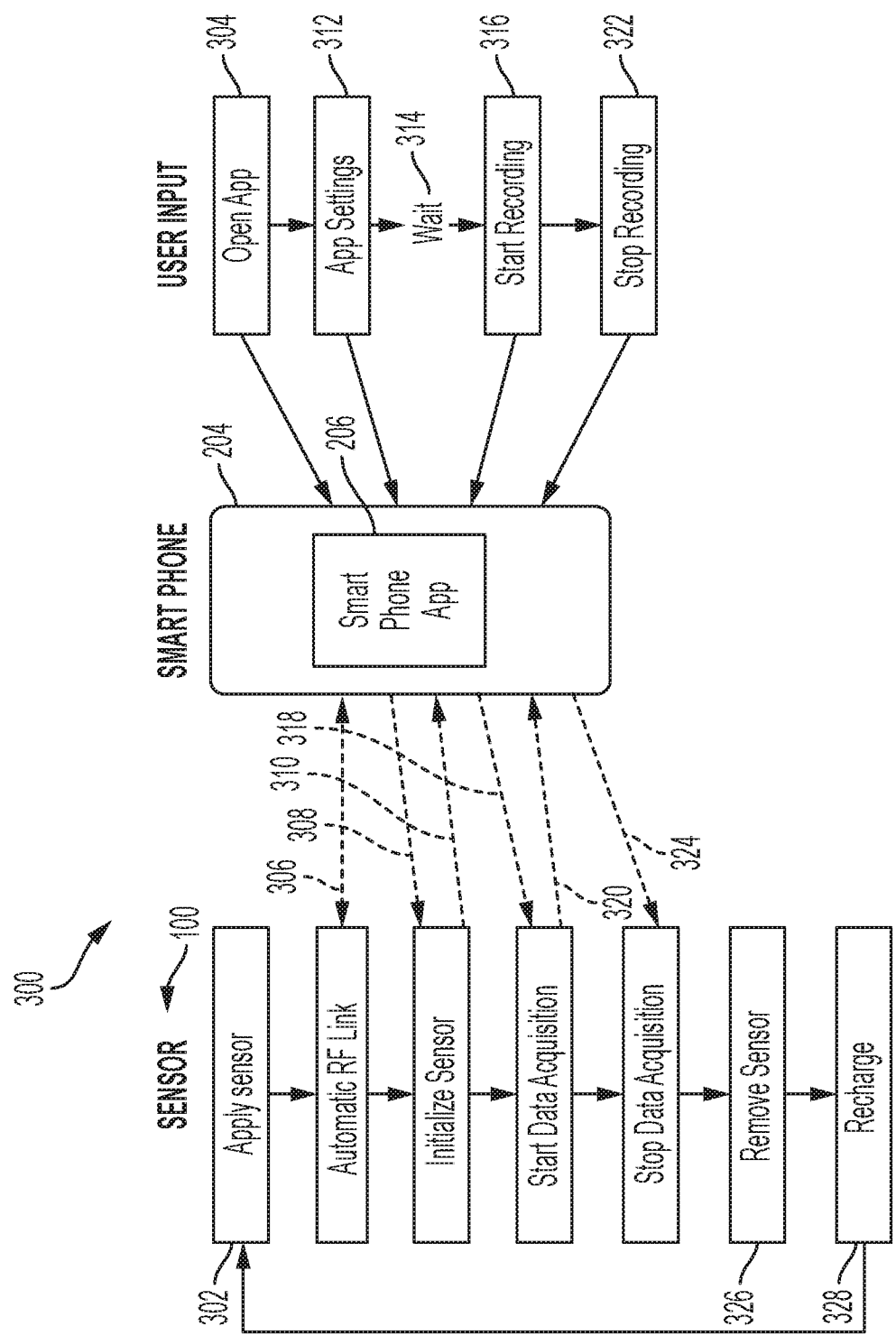
FIG. 3 is an exemplar operational flow diagram for the sensor monitoring device system firmware.

FIG. 3 is a block diagram illustrating the ECM sensor 100 patient experience for the purpose of monitoring during sleep. The fully-recharged ECM sensor 100 is first applied 302 to the patient. Suitable locations for applying the device includes the mid-upper arm with an elastic wrap in such a way that the sensor is held comfortably, but firmly in place without restricting blood flow in the arm. The mid-upper arm location is a suitable location for sleep monitoring. However, as will be appreciated by those skilled in the art, other locations on the body can be employed without departing from the scope of the disclosure, including, but not limited to, the forehead, wrist, body core, thigh, or calf.

The application program 206 is then loaded and opened 304 by the patient using an automatic RF link 306 between the smartphone and the ECM sensor 100. The ECM sensor 100 is initialized after, for example, receiving the sensor initialization command 308 from the smartphone app, and the sensor responding that the sensor is initialized 310. The initializing command is an automated link-seeking process, whereby the sensor's RF link confirming response is automatically detected and indicated on the app graphical user interface (GUI) presented in the smartphone. The patient can select application settings 312 for the recording session on the application program 206, then the patient has the option to start recording data 316 immediately, or wait 314 until a chosen moment, such as when synchronizing the sleep record with the recording of another sensor system is desired. Upon instructing the start recording data 316, the ECM sensor 100 is sent instructions to start data acquisition 318 at the selected cycle frequency, such as once per second for the 685 LED, and up to 10 times per second for the 850 nm LED in application with infants who may have a respiratory rate during sleep of over 100 breaths per minute. As the data is acquired and transferred 320 by RF link to the smartphone, it is recorded in smartphone memory and, optionally displayed graphically on the smartphone GUI screen for the application program 206 as raw data and as Energy Conversion index (ECi) trends. Upon patient command to stop the recording 322, the application program 206 generates the stop command 324, which is transmitted via the RF link, to the ECM sensor 100 to cease data acquisition. The recorded data is saved in a desired computer format, such as tab-delimited ASCII text (*.txt) within the smartphone memory, which data file can then be transferred by a variety of digital communications processes available with the smartphone. The patient then removes the sensor 326 and recharges 328 the ECM sensor 100 by, for example, placing it on a compatible recharging pad to wirelessly recharge the internal battery. When the ECM sensor's battery is fully recharged, the ECM sensor may be used again. In some configurations, the system is configurable to start and stop the recording automatically based on previously administered instructions. Thus, for example, the system can be programmed to collect data between a specific time period, or upon occurrence of a specified event (e.g., onset of snoring, movement of patient during sleep, etc.).

As will be appreciated by those skilled in the art, the ECM sensor 100 can, in some configurations, be operated automatically or semi-automatically via an airway therapy device or a central server in communication with the airway therapy device and ECM sensor 100. In these configurations, the use of a smartphone may not be required. Thus, systems according to the disclosure can include two or more of the following: ECM sensor, smartphone, airway therapy device, and/or central server.

Figure 4:
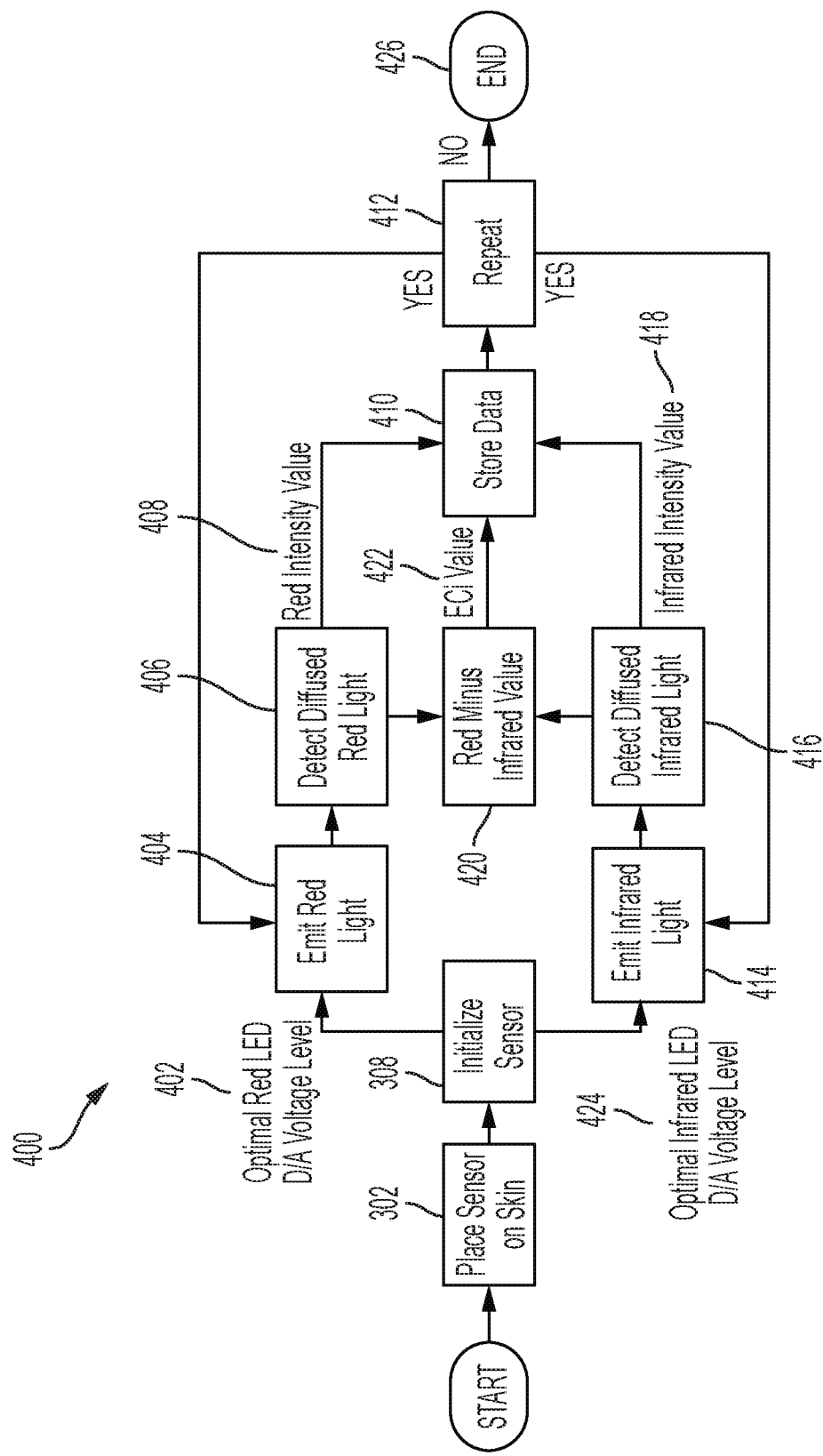
FIG. 4 illustrates an exemplar data acquisition flow diagram.

FIG. 4 is a flow diagram 400 depicting the operation of the ECM sensor 100. A procedure of use for monitoring sleep starts with placing the sensor on the skin (first applied 302). As noted previously, the ECM sensor can be placed on the mid-upper arm with an elastic wrap or arm band. The application program 206 can be used to send the ECM sensor the sensor initialization command 308, producing an optimal D/A control voltage level for the red LED 402 and an optimal D/A control voltage level for the infrared LED 424. A data acquisition cycle includes emitting red LED light 404 and detecting the diffused red LED light 406 to determine a red intensity value 408. The data acquisition cycle includes emitting an infrared-LED 414 and detecting the diffused infrared light 416 to determine an infrared intensity value 418. The process can also include periodically sampling the background ambient light value, which is subtracted from the diffused red LED light 406 that is detected and from the diffused infrared light 416 that is detected. With the background value removed, the resulting infrared intensity value 418 is subtracted 420 from the resulting red intensity value 408 to generate an ECi value 422. The ECi value can range from less than −400 (deeply hypoxic skin), through zero (normal, aerobic skin), to over +500 (very hyperoxic skin). The red intensity value 408, the infrared intensity value 418, and the ECi value 422 are then stored in sensor memory 410. The data can then be transmitted via the RF transmission to the application program. This data acquisition cycle repeats 412 until the patient instructs the data acquisition to stop (i.e., stop the recording 322), causing the data acquisition cycle repeat 412 to return 'no,' and the sensor operation ends 426.

Figure 5:
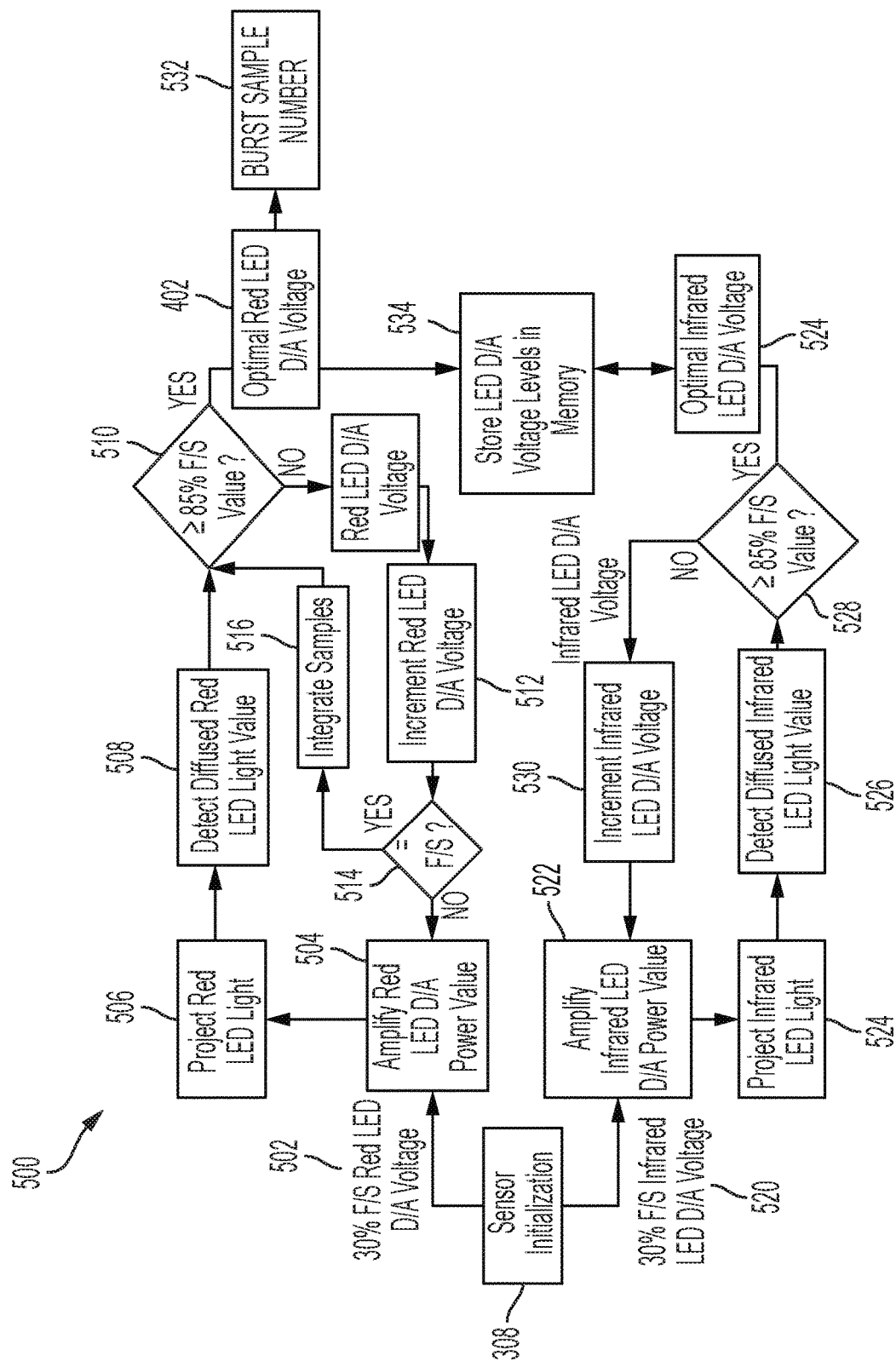
FIG. 5 illustrates an exemplar LED power level initialization flow diagram.

FIG. 5 is a flow diagram 500 of the sensor initialization process based on the sensor initialization command 308 in FIG. 3. The sensor initialization command 308 starts with setting red LED power level at 30% full scale of the LED power D/A converter 502. Resolution is at a minimum of 12-bit (i.e. 0-4095). The D/A voltage is then amplified 504, and powers the red LED to project the red LED 506 light. The detected intensity of the projected red LED light after having diffused through the skin 508 is converted to a photocurrent by the detector 128 in FIG. 1C, e.g. photodiode, then amplified by a signal amplifier 242 in FIG. 2, before being delivered to the signal analog-to-digital (D/A) converter in the sensor microcontroller 240 in FIG. 2. The diffused red light is sampled and digitized, and the digital value is checked to see if it is equal to, or greater than 85% full scale 510 of the output data A/D converter. Resolution for output data is at least 12-bit (e.g. 0-4095). If the digitized value is less than 85% full scale, (e.g. <3480), the red LED D/A voltage is incremented one 12-bit step 512, amplified 504 and red LED light is again projected 506 into the skin. This cycle continues until the digitized data equals or exceeds 85% full scale, whereupon, the optimal red LED D/A voltage level 402 is stored in sensor memory 214 in FIG. 2. However, if the upper limit of the 12-bit D/A red LED voltage scale is reached without achieving 85% full scale data 514, such as happens with darkly pigmented skin, a sample integration process 516 is entered. The sampling process involves taking 16 burst samples while the red LED is illuminated, summing their digital values, and dividing the sum by 16 to produce an averaged sample. With integration 516, the number of burst samples is incremented at each cycle until the sum of the digital values, divided by 16, equals or exceeds 85% full scale 510.

Upon achieving 85% full scale 510, the optimal red LED D/A voltage level 402 and the burst sample number 532 are stored in sensor memory 534. Upon completion of the red LED initialization, the infrared LED D/A voltage is similarly cycled, started from 30% full scale infrared LED D/A voltage 522, illuminating the skin 224 (FIG. 2) by projecting infrared LED light 524 onto the skin, sampling and digitizing the signal 526, and checking for being equal or greater than 85% full scale 12-bit resolution 528. Since the infrared wavelength is not absorbed by skin pigment, and the infrared LED's power input to light output efficiency is much greater than the red LED, the infrared LED D/A voltage is easily achieved without integration. Upon achieving equal or greater than 85% full scale output data value 528, the optimal infrared LED D/A voltage 424 is stored in sensor memory. The sensor initialization process is complete when both the optimal red LED D/A voltage level 402 and the optimal infrared LED D/A voltage level value 424 are then stored in sensor memory 534.

The importance of discerning weak or absent breathing efforts during sleep warrants obtaining optimum resolution. To achieve this, the tandem decline in intensity values that typically occurs during the initial hour 802 of sleep, as shown in FIG. 8B, needs to be compensated to bring the baseline detected intensity back up to the 85% full scale range through the remainder of the night's sleep. The process for doing this is to repeat the sensor initialization step at 30 minutes, then again at one hour into the sleep recording. During the short time periods when a second and third sensor initialization command (corresponding to sensor initialization command 308 in FIG. 4) is carried out, the sensor memory 214 in FIG. 2 is sent full-scale red (e.g. 4095) and infrared (e.g. 4095) data values at the times when detected data would normally be sent. This produces full scale 'intended artifact' spikes in the output red and infrared intensity raw data and zero ECi values, indicating an intended deviation in the data values during repeat initialization; and then the ECM sensor system 202 in FIG. 2 continues to sample and log detected data using the new initialization LED power control and burst sample number values for subsequent cycles.

Use of BluetoothLE® for the RF link has the advantage of automatically attempting to re-transmit data that has not received an acknowledgement of intact reception. However, in the event of an extended period of time when RF communication is interrupted, the sensor memory 214 in FIG. 2 has the capacity to store up to 4 hours of data for transmission when the RF link is restored.

Figure 6A:
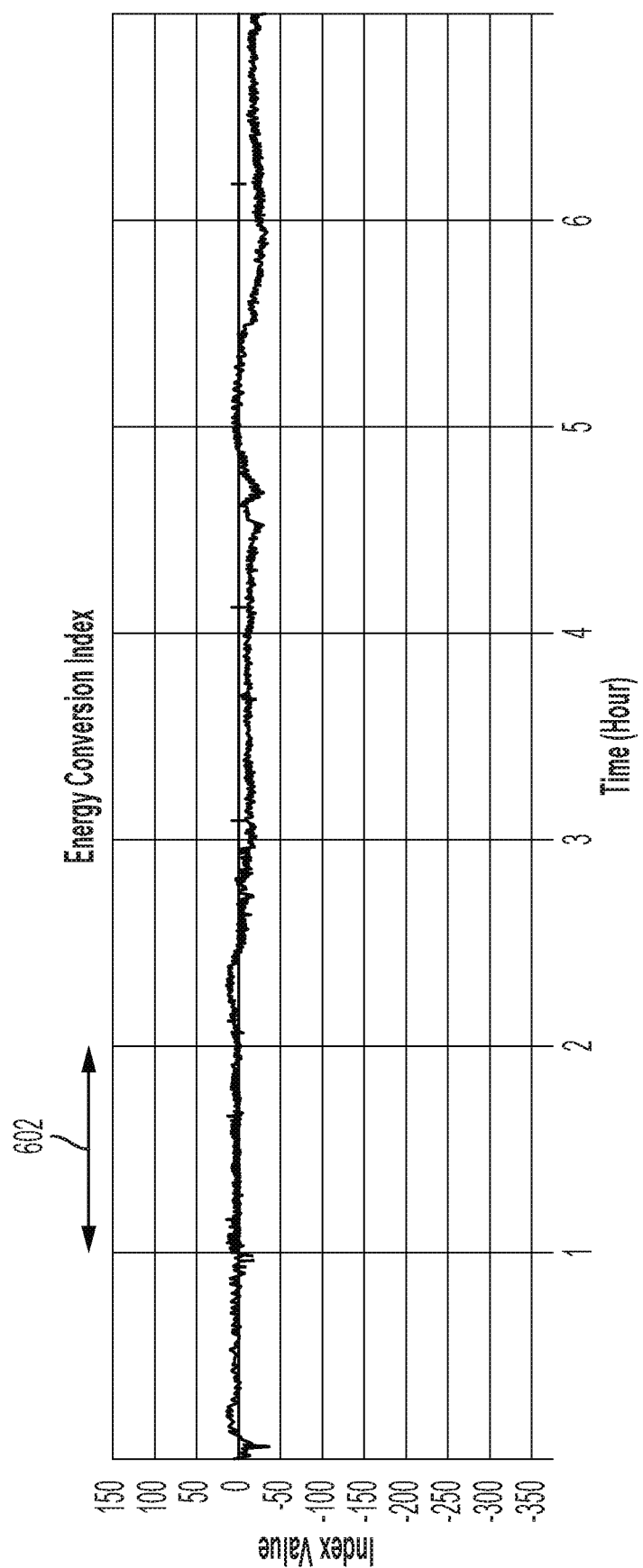
FIG. 6A is an Energy Conversion Index (ECi) graph recorded during normal sleep.

FIG. 6A is a graph of ECi recorded during normal sleep. The ECi value during sleep has been recorded to range between −450 and 100. The X-axis on the ECi graph is a shown at one-hour time intervals 602 corresponding to one hour of recording. FIG. 6A is a 7-hour 'sleep' segment of a longer record that started with the subject reclining in his easy-chair watching TV before going to sleep in his bed. There is very little variation in the calculated ECi value; never decreasing below −50, indicating that he had normal breathing and skin oxygen supply throughout the night.

Figure 6B:
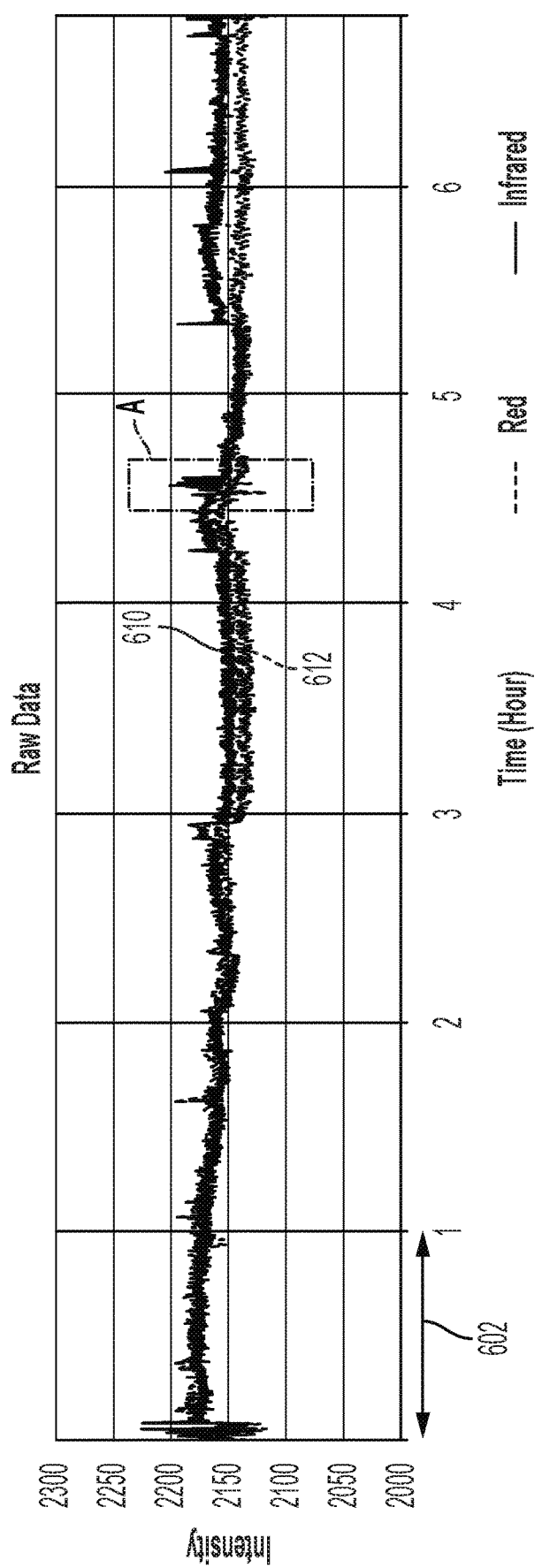
FIG. 6B illustrates a raw data graph of intensity over time recorded during normal sleep.

FIG. 6B is a raw data graph from which the ECi trend data in FIG. 6A was calculated, showing an infrared signal intensity trace 610 and a red signal intensity trace 612. One brief period of slightly disordered breathing A is selected for expanded view in FIG. 6C. The relatively consistent raw data trace indicates very little change in body position or rolling over during sleep. Although not perfectly free of indication of breathing changes, this is one of the 'most-normal' sleep recordings made to date.

Figure 6C:
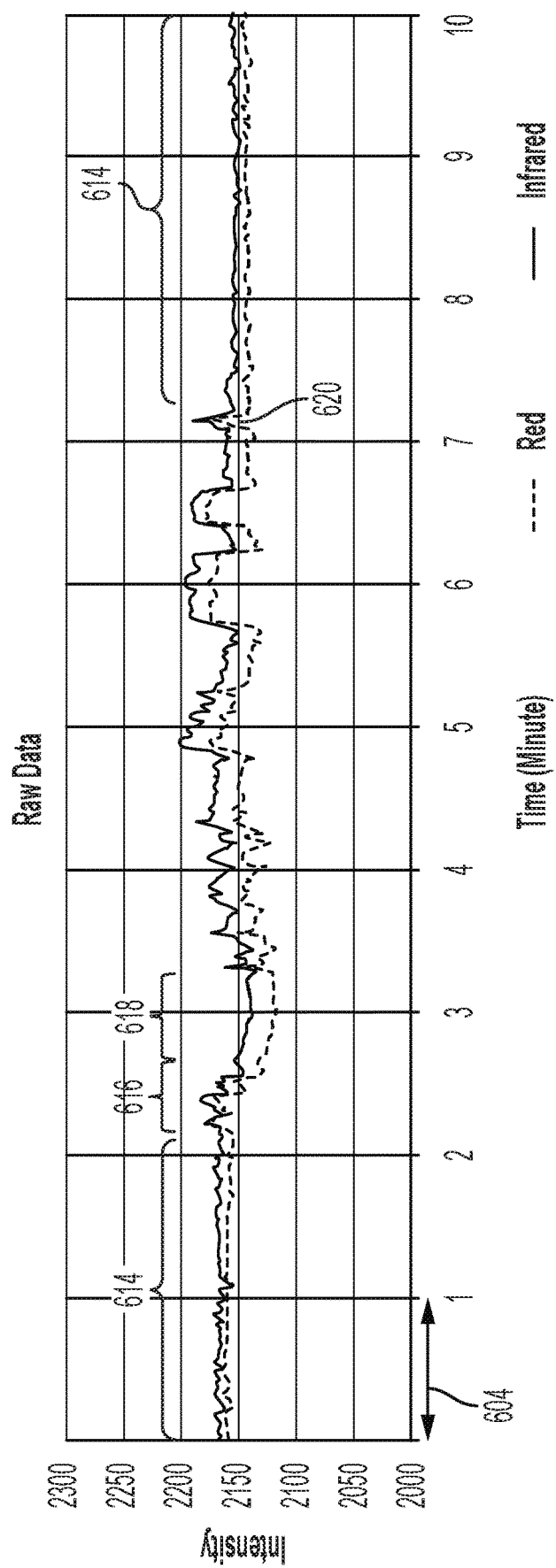
FIG. 6C illustrates a selected portion A of intensity over time extracted from FIG. 6B recorded during normal sleep.

FIG. 6C is a time-expansion of segment A of the FIG. 6B raw data graph recorded during normal sleep. The Y-axis reflects detected signal intensity and the X-axis reflects one-minute time intervals 604. Normal quiet breathing 614 is shown at the beginning and the end of the raw data segment. A few slightly obstructed breaths 616, e.g., soft-snoring, lead to an almost one-minute period of decreased breathing effort 618 that results in a slight drop in both red signal intensity trace 612 and infrared signal intensity trace 610, but more so of the red signal intensity trace 612, giving an indication of slightly decreased oxygen supply to the skin. Also, of note in several places through the middle portion of this graph are the tandem variations of both the red signal intensity trace 612 and the infrared signal intensity trace 610. The more pronounced variations are due to deeper excursions in intrathoracic pressure that are needed to move air through a partially obstructed airway. If, on a single breath, the airway is fully obstructed, there is typically a tandem vertical spike 620 from the brief increased effort.

Figure 7A:
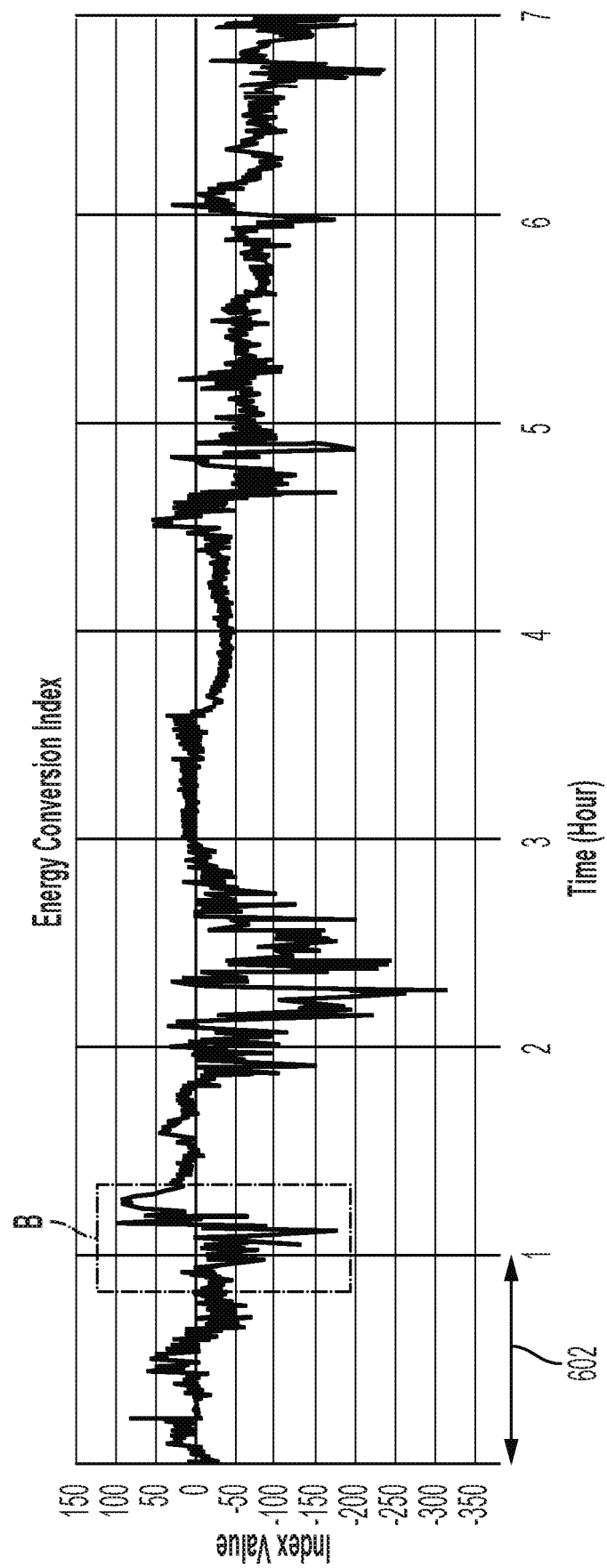
FIGS. 7A-B are an abnormal ECi and a Raw Data graph recorded during sleep, showing the response to an episode of OSA.

FIG. 7A is an abnormal ECi trend graph recorded during sleep complicated by obstructive sleep apnea (OSA), snoring, and central sleep apnea (CSA). The Y-Axis is the ECi Value and the X-axis is time (hours). The X-axis uses the same one-hour time intervals 602 as the X-axis in FIG. 6A. Note that the same Y-axis range is used as in FIG. 6A. Segment B occurring at around the 1-hour mark in FIG. 7B is outlined for time-expansion in FIG. 7C.

Figure 7B:
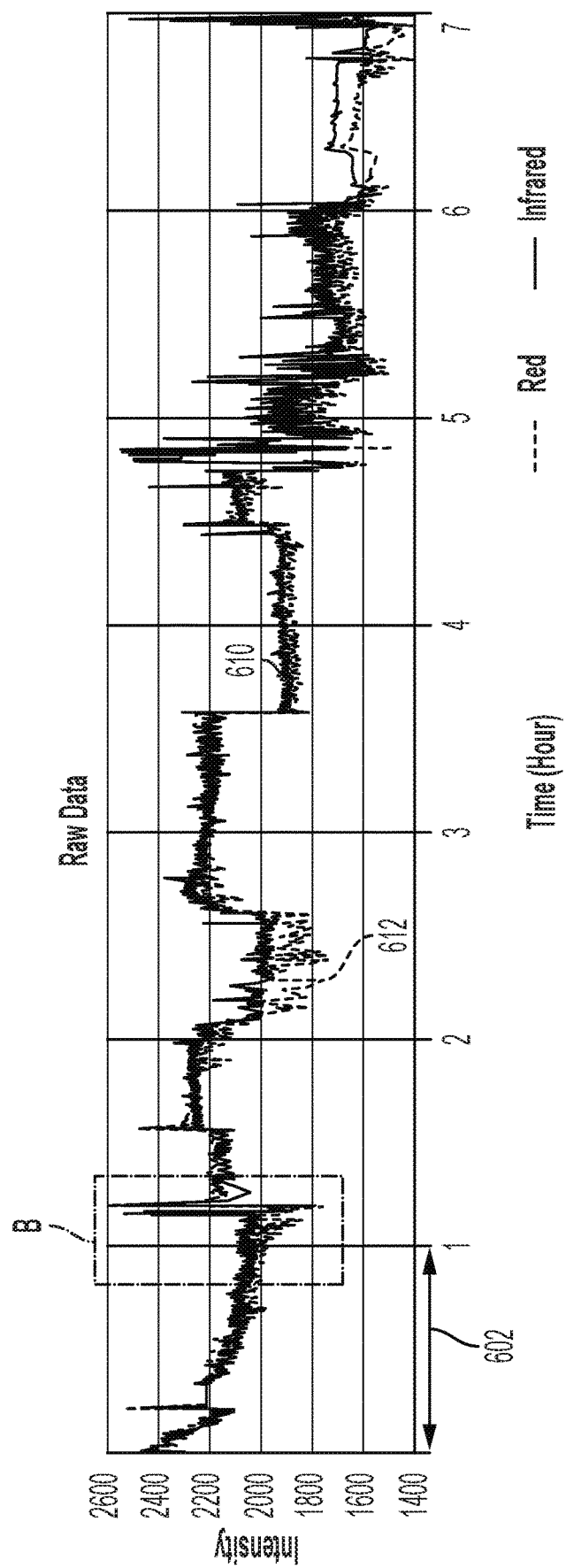

FIG. 7B is the raw data graph from FIG. 7A. Note that the deeply negative index values for the ECi excursions in FIG. 7A correspond with periods when the red signal intensity trace 612 shown in FIGS. 6B-C is a lower value trace than the infrared signal intensity trace 610, indicating more red-light absorption in the skin. The graph illustrates both red signal intensity trace 612 and infrared signal intensity trace 610. The outlined segment B is time-expanded in FIG. 7C.

Figure 7C:
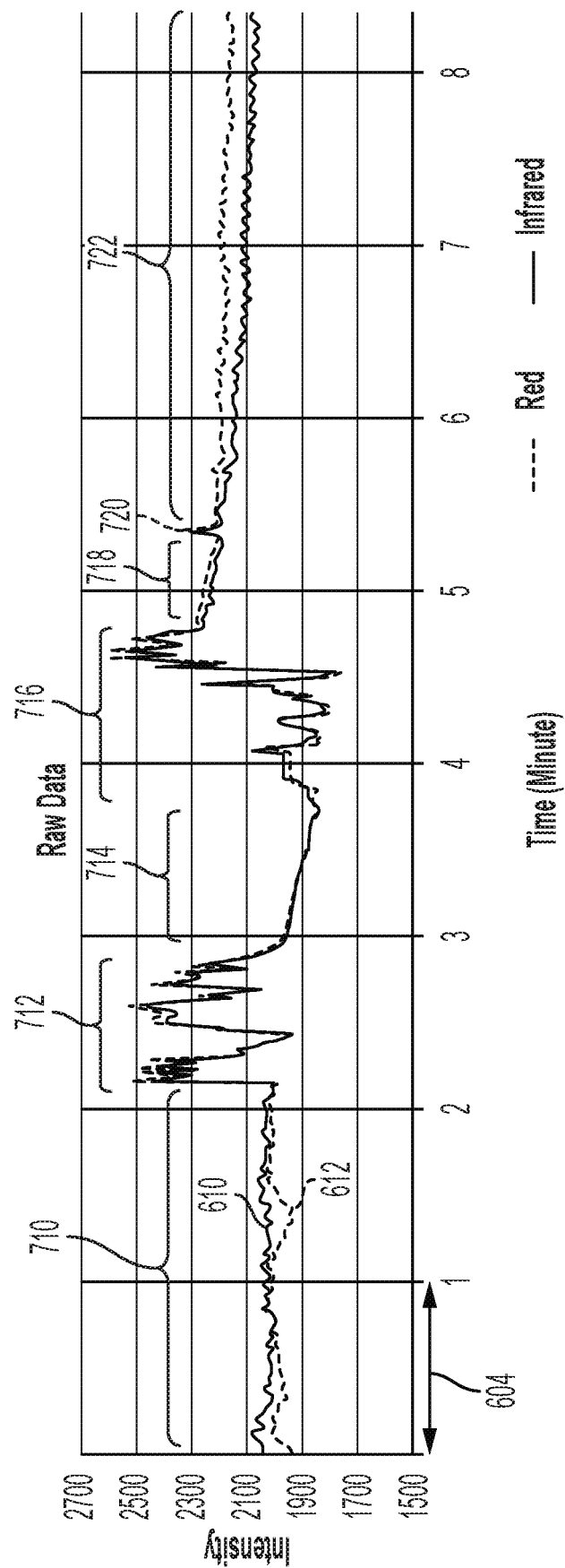
FIG. 7C is a time-expansion of the Raw Data segment B from FIG. 7B.

FIG. 7C is a time-expansion of the raw data segment B in FIG. 7B also showing both red signal intensity trace 612 and infrared signal intensity trace 610. The X-axis is a time value at one-minute time intervals 604 as shown in FIG. 6C. This segment begins with 2 minutes of soft snoring and periodic breathing, resulting in slight periodic drops in red intensity vs. infrared intensity signifying a cellular hypoxia response. Then, there is one-minute episode of severely restricted airway 712 with three strong attempts to obtain a breath. A one-minute period of apparent central sleep apnea 714 (i.e., no breathing effort) follows, but is interrupted by resumption of increasing efforts to obtain a breath through a restricted airway which occurs with obstruction apnea 716. This airway restriction/obstruction period is followed by another period of central apnea 718 with minimal breathing movement, which ends with a one-breath obstruction 720. Finally, the subject apparently rouses from sleep enough to open his airway and resumes normal breathing 722 as he tries to get back to sleep.

Figure 8A:
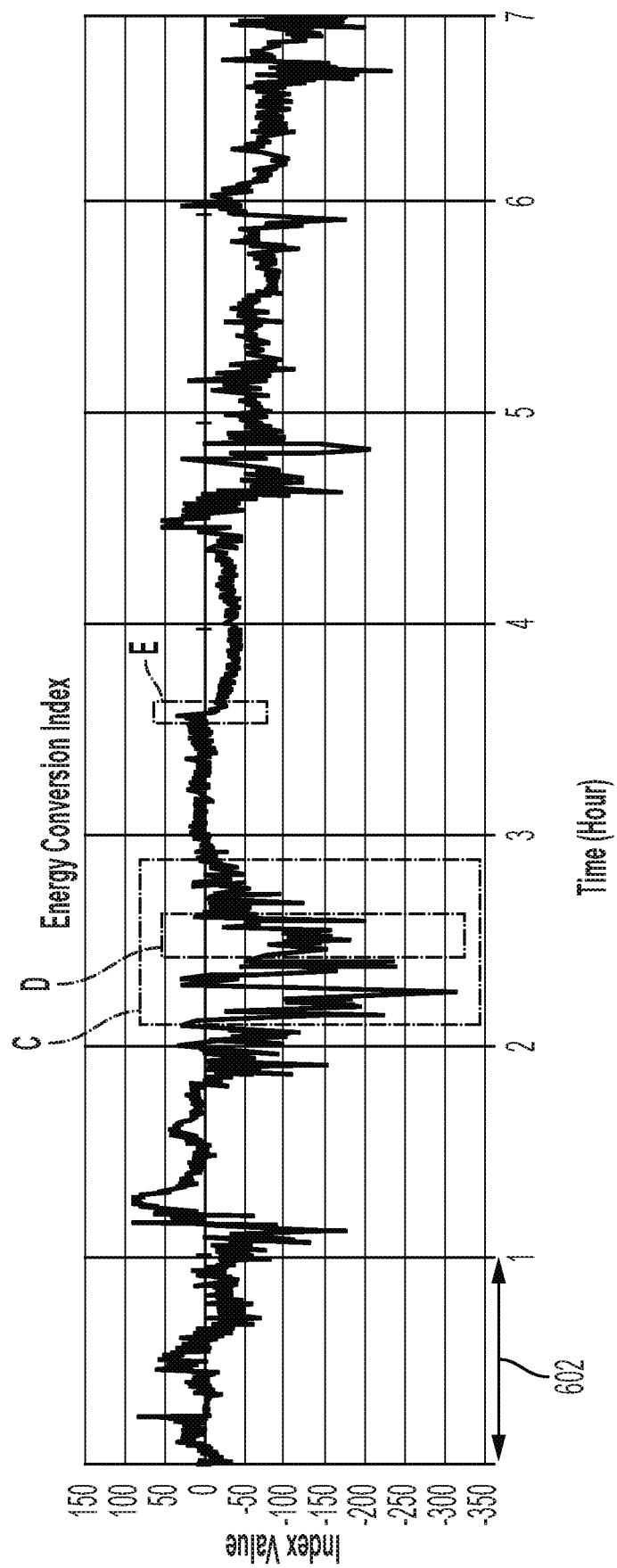
FIG. 8A illustrates an abnormal ECi recording from FIGS. 7A-C, but with two different nested segments, C and D, selected for time-expanded view.
Figure 8B:
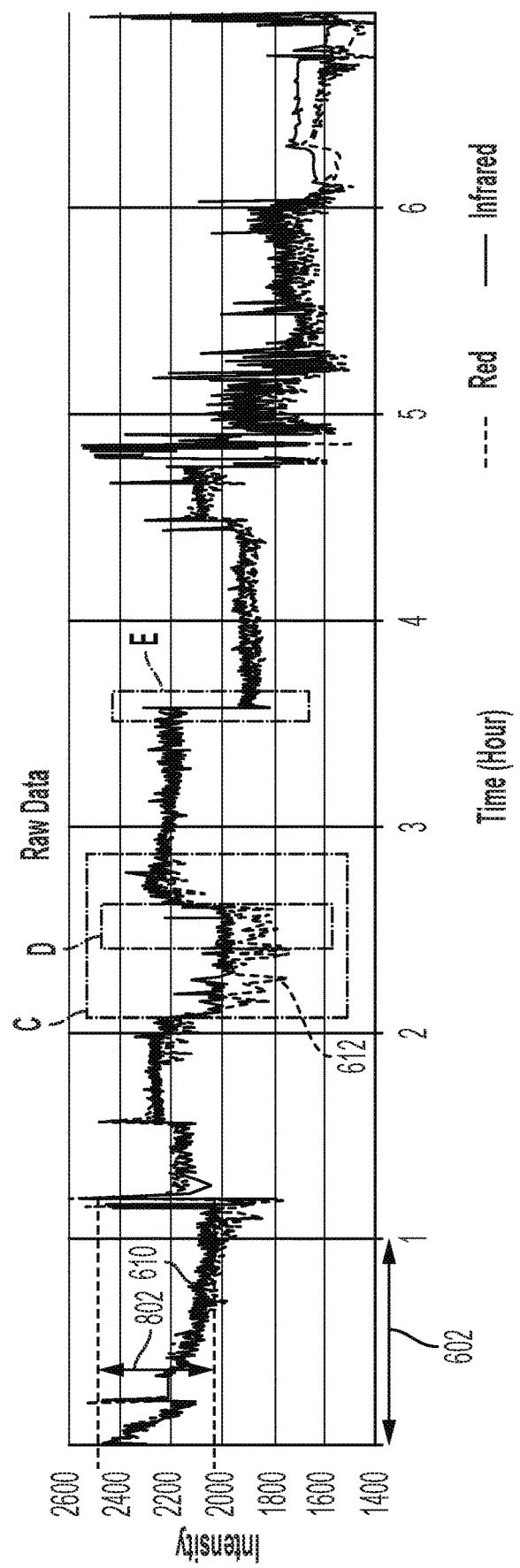
FIG. 8B is a Raw Data graph from the ECi recording in FIG. 8A.

FIG. 8A is the same ECi recording as FIG. 7A, with two segments selected for time-expanded review: C and D. Segment D is a subset of segment C, occurring between hour 2 and hour 3. Segment E is an example of the subject rolling over. The Y-Axis is an ECi index value and the X-axis is a time value at one-hour time intervals 602.

FIG. 8B is the raw data graph from the ECi recording in FIG. 8A, showing the two nested segments for review along with both red signal intensity trace 612 and infrared signal intensity trace 610. The X-axis is a time value at one-hour time intervals 602. The Y-axis is detected signal intensity. Also, note the tandem downward trend during the initial hour 802. This nearly 500 count baseline decrease is a common finding during sleep studies and correlates with movement of venous blood from the lower trunk and legs while the body is upright to be redistributed more evenly throughout the length of the recumbent body over the first hour in bed. Segment C is time-expanded in FIG. 8C and nested segment D is further time-expanded in FIG. 8E. Segment E, as also noted in the ECi graph FIG. 8A, is the raw data trend that typically occurs with rolling over; comprising an abrupt, tandem baseline shift of both red and infrared data values due to normal shifting of venous blood from one side of the body to the other side of the body due to gravity.

Figure 8C:
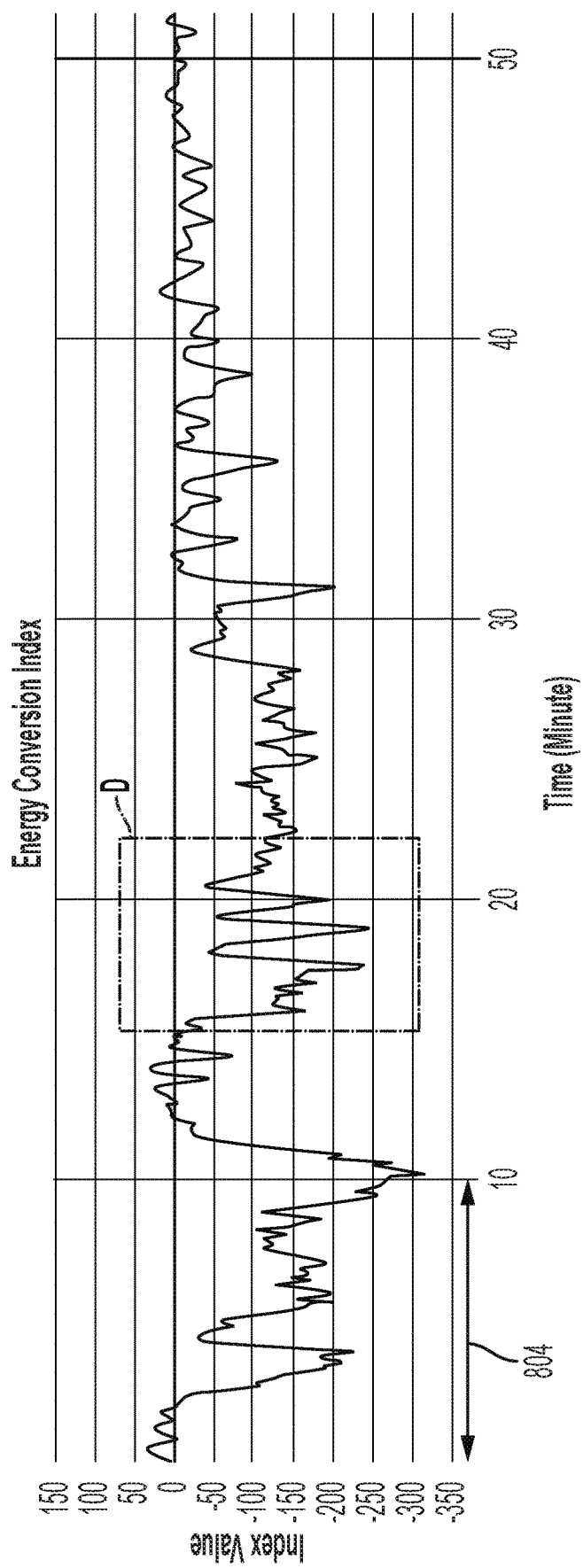
FIG. 8C is a time-expanded segment C from the ECi recording in FIG. 8A.

FIG. 8C is the time-expanded segment C from the ECi recording in FIG. 8A, also showing the nested time segment D from FIG. 8A and FIG. 8B outlined, and with a time value on the X-Axis at a ten-minute time interval 804. The wide deviations seen in the previous graphs are not 'noise' in the sense that the deviations vary smoothly over minutes of time. To put this in context with more familiar measurements, parallel recordings with a pulse oximeter sensor while the subject breathes nitrogen have correlated ECi values less than −300 with the SpO$_2$ dropping below 70%.

Figure 8D:
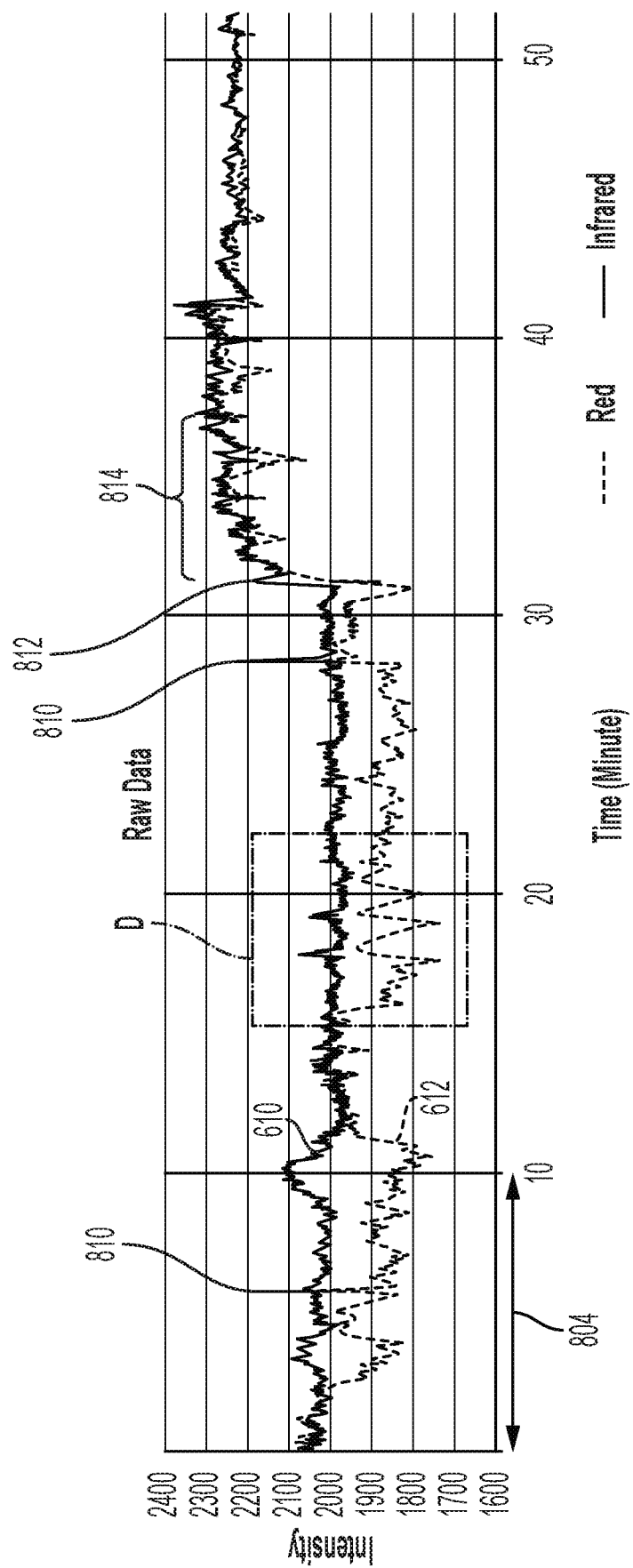
FIG. 8D is a Raw Data graph of segment C from FIG. 8C.

FIG. 8D is a raw data graph corresponding with the ECi trend in FIG. 8C, also showing nested time segment D that is also shown in FIG. 8A and FIG. 8B at a ten-minute time interval 804, with both red signal intensity trace 612 and infrared signal intensity trace 610 shown. Divergent response patterns of the red signal intensity trace 612 and infrared signal intensity trace 610 are evidenced indicating that these deviations are not the tandem pattern that is due to sensor motion or breathing, but rather to distortions in the cellular oxygen supply status of the skin. two prominent single-breath obstructions 810 are seen, but most of this recording is during periodic breathing with a variably restricted airway; i.e. snoring. An abrupt tandem change in baseline intensity 812 of the red signal intensity trace 612 and the infrared signal intensity trace 610 occurs with the person rolling over; in this case to sleeping on the side that places the sensor above the heart, thus presenting less venous blood absorption of both red and infrared light. There is also an about 8-minute period 814 after rolling over when the blood volume in the skin beneath the sensor continues to decrease, then stabilizes.

Figure 8E:
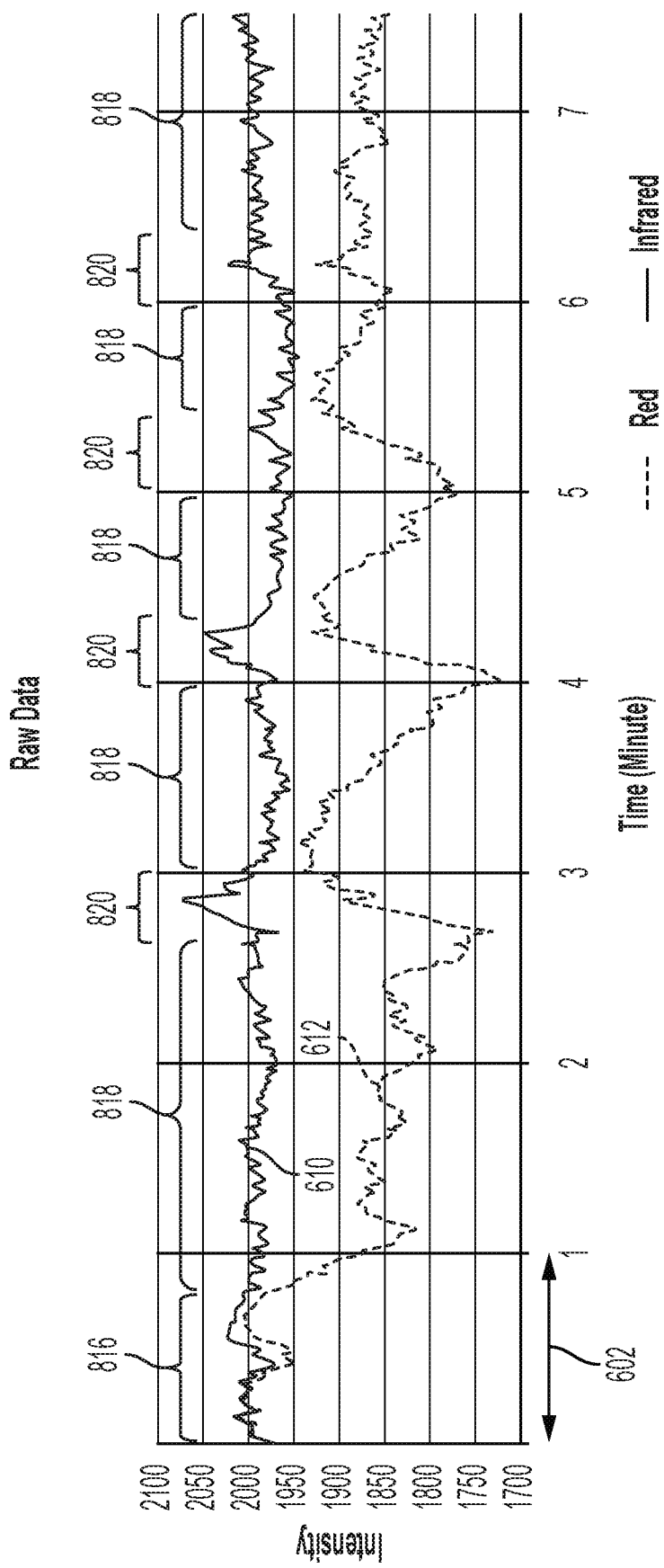
FIG. 8E is a Raw Data graph of segment D from FIG. 8D.

FIG. 8E is the raw data graph of nested time segment D from FIGS. 8A-D showing both red signal intensity trace 612 and infrared signal intensity trace 610. This signal pattern is recognizable from parallel PSG studies where the PSG microphone detected snoring with little or no simultaneous deviation from 'normal range' SpO$_2$ values during prolonged periods of nearly identical trend patterns. This 7+ minute segment is a record of periodic breathing and heavy snoring, but without airway obstruction. Similar ECi trends occur during parallel PSG recordings including normal nasal air flow and normal patterns and range of motion of the chest and abdomen sensor straps—with snoring. The PSG data shows sufficient breathing effort to move the normal amount of air per breath, despite the partial obstruction of the subject's airway. However, this ECi raw data pattern of periodic breathing and corresponding cycles of skin hypoxia ECi response during snoring is an apparent indication of a physiologic response to stress that may well be a measurable 'missing link' connecting snoring during sleep and development of hypertension.

This period starts with normal breathing 816, then goes into an initial 2-minute period of snoring 818. The progressively deeper skin hypoxia, and presumably also a possible drop in SpO$_2$, triggers arousal and several deeper breath efforts 820 sufficient to restore almost all the way back to normal. However, snoring resumes 818 and, over a 1-minute period, returns the skin to deep hypoxia. This pattern repeats at least three more times during this segment, but, as shown in FIG. 8D, this snoring episode lasts over 15 minutes and ends only when the person arouses, rolls over and gets back to normal breathing after a total of about 35 minutes.

The disclosed ECM sensors 100 can be used for home-based diagnostic testing for SDB during sleep of children, adolescents, and adults. The home-based testing application can be monitored real-time, or near real-time, from a remote location, and would be directed by a licensed and qualified physician who would analyze the data produced, diagnose the patient's condition based on the patient's history and the recorded data, and prescribe needed treatment.

FIGS. 9A-E present five sleep recording segments showing when and in which direction ECi data can be used to trigger APAP changes in airway pressure. The figures include the infrared intensity trace 610 and the red signal intensity trace 612. The sleep breathing pathology also portrayed in FIG. 7C starts with a transition from variably restricted breaths 710 of soft snoring with periodic slight skin hypoxia 902 to a full airway obstruction event 904. Had the breathing pattern been detected at the first arrow 902 during the snoring, and had airway pressure immediately been increased, the full airway obstruction event 904 may have been less severe, or may not have occurred at all. Had there not been abnormal breathing prior to the full airway obstruction event 712, ECi detection of the full airway obstruction event 904 could also have triggered an immediate increase in airway pressure to reduce the problem.

Another example 910 is shown in FIG. 9B that is taken from the beginning of the record in FIG. 8E, of a potential trigger point for APAP machine air pressure control starts with a period of widely varying breath depth 912 followed by severe enough airway restriction 916 to produce a large non-tandem red intensity signal 612 value drop in segment 914, likely associated with heavy snoring. If the change in breath depth 912, or effort, had not triggered an increase in airway pressure, the large non-tandem red intensity signal value drop at 914 should trigger an increase in airway pressure. Also, of note is the change in breathing pattern 918 that naturally interrupts the skin tissue hypoxia event 916. This likely represents a slight arousal and interruption in sleep, but, as shown in the more detailed record illustrated in FIG. 8E, does not resolve the episode of SDB.

A further example 920 is in FIG. 9C and involves a roll-over during sleep occurring at 922, which is characterized by one or more large, tandem variations 924 in the red and infrared raw data signals. This pattern needs to trigger an immediate decrease in airway pressure. There may, or may not, have been breathing difficulty leading to rolling over, but one of the more annoying aspects of airway pressure therapy is waking upon rolling over to find the APAP pressure high, and remaining high, despite being fully-conscious and breathing normally. The ECM detects roll-over by a tandem shift of the red and infrared signals 926, due to the movement of venous blood to the opposite side of the body. APAP air pressure and flow sensors cannot detect when a person rouses from sleep enough to change position. It is unlikely that a person will continue any SDB events that were happening just before a roll-over.

Another example 930 in FIG. 9D shows how the ECM enables detection of central sleep apnea (CSA) and making appropriate pressure changes in response. FIG. 9D is an excerpt from FIG. 7C, between about 4 and 6 minutes showing a restricted airway associated with obstructive apnea 716 followed by central apnea 718. The APAP therapy needs to recognize and aggressively treat the obstruction event with higher pressure. However, if higher pressure induces a pause in breathing, such as at arrow 932, it could either decrease pressure, or possibly provide a haptic stimulus to help abort the episode of central apnea.

FIG. 9E is another example of central sleep apnea 714 following an earlier obstruction event from FIG. 7C, and shows no evidence of effective breathing effort 714 for over one minute. While most adults with this pattern of SDB can continue to sleep, albeit with less than the desired sleep quality, infants with similar patterns may be at increased risk of SIDS; and may not survive! The disclosed ECM sensors are able to detect and provide recognizable data signatures of these potentially life-threatening events as they happen, and trigger an alarm, such as at arrow 902 in FIG. 9A, or trigger some other stimulus, such turn on a buzzer vibrator motor (haptic stimulus) included in the sensor housing in the case of SIDS-risk infants, that can reliably arouse the person enough to resume effective breathing. Some children and adults with SDB also have periods of central apnea while receiving airway therapy if the airway pressure from the airway therapy device increases in response to an OSA event, but becomes too high. This phenomenon is thought by sleep medicine experts to be a reflex suppression of the normal breathing drive by airway pressure-induced stimulation of stretch receptors in the person's lungs. Effective response has been found with immediate reduction of the airway pressure. However, consistently effective detection of this condition with current airway therapy equipment has been a long-standing problem. Fortunately, most persons who have this response eventually 'get used to' the higher-than-needed pressure and can tolerate lapses in machine control response. The ECM offers a new method of detecting periods of CSA interspersed with OSA; thus, potentially providing more accurate APAP machine response to these events.

Figure 10A:
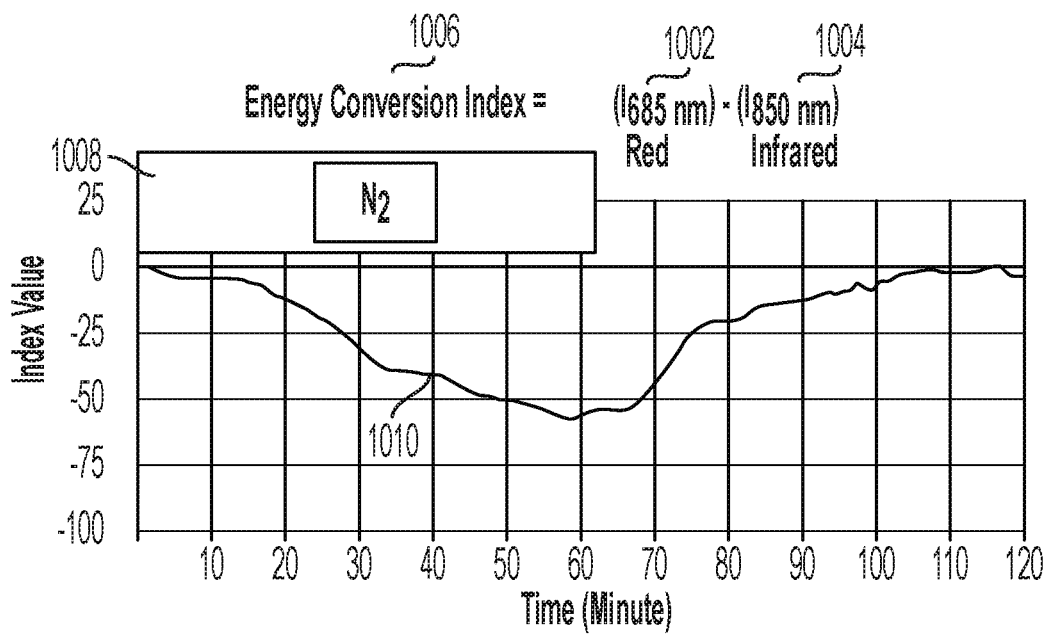
FIGS. 10A-D are graphs reflecting exemplar output data for a sensor monitoring device and signal trends.
Figure 10B:
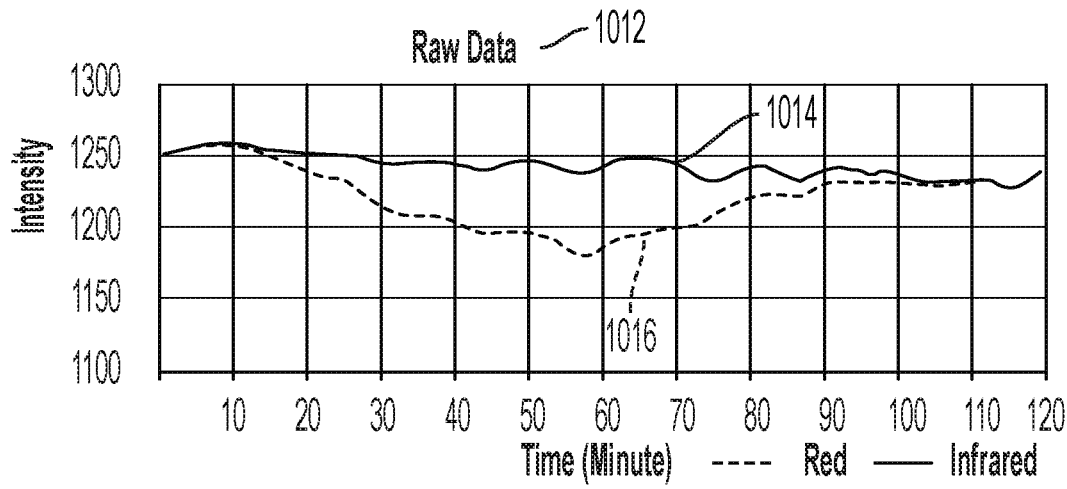
Figure 10C:
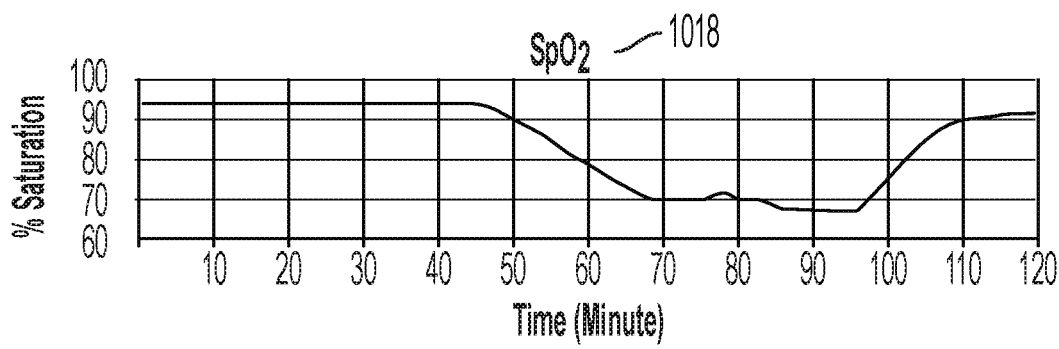
Figure 10D:
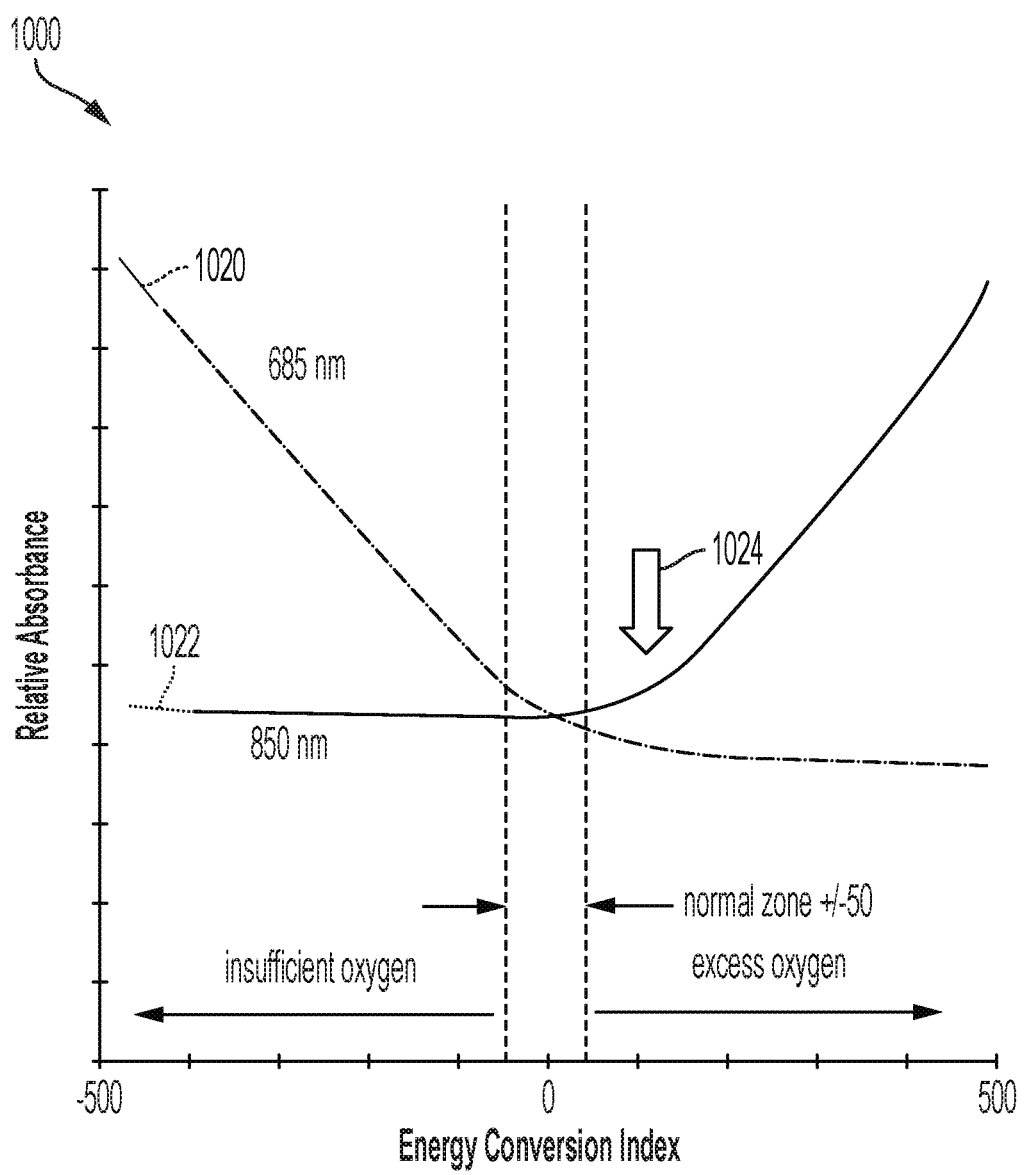

FIGS. 10A-D illustrate calculations and characteristics of sensor signal trends from a sensor monitoring device. FIG. 10A measures an Index Value (Y-axis) over time (X-axis); FIG. 10B measures an Intensity (Y-axis) over time (X-axis); FIG. 10C measures a percent saturation (Y-axis) over time (X-axis). FIG. 10D is a schematic representation of the Relative Absorbance of light at two center wavelengths (Y-axis) and an energy conversion index value (X-axis) that would be computed from the resulting detected signal intensity values, as a function of cellular oxygen supply. The X-axis goes from extremely low oxygen supply on the left, through normal oxygen supply to excessive oxygen supply on the right.

As shown in FIG. 10A, the present disclosure uses detected light intensity values (I) at two wavelengths: 685 nm (red) 1002 and 850 nm (infrared) 1004. The output data, calculated as an Energy Conversion Index (ECi) 1006, is obtained by subtracting the detected 850 nm intensity value 1004 from the detected 685 nm intensity value 1002. When these data are obtained while the subject breathes nitrogen ($N_2$) gas 1008, an ECi trend 1010 is produced. Data can be obtained, for example, at a rate of once per second. Turning to FIG. 10B, the Raw Data 1012 from which the ECi trend 1010 is computed has been demonstrated to have consistent response characteristics relative to the physiologic and biochemical stresses placed on the skin tissue being monitored. Grossly, the 850 nm trend 1014 varies cyclically with the subject's breathing effort, but is not affected when the oxygen supply to the skin tissue is less than normal to normal. The 685 nm trend 1016 is slightly less affected by breathing, but this wavelength is more absorbed when the oxygen supply to the skin tissue being monitored decreases. The simultaneously recorded pulse oximetry ($SpO_2$) data 1018 in FIG. 10C shows the change in blood oxygen resulting from breathing nitrogen. Note the delayed $SpO_2$ responses, both at the beginning and the end of the episode.

The Relative Absorbance responses for the two wavelengths is shown diagrammatically on FIG. 10D. As the oxygen supply to skin tissue decreases relative to the normal zone the 685 nm light 1020 is increasingly absorbed, but the absorbance of the 850 nm light 1022 does not change. Increasing the oxygen supply above normal results in some continuing decrease in absorbance of the 685 nm light 1020, while the absorbance of the 850 nm light 1022 increases sharply. The approach to the threshold into excess oxygen supply 1024 can, therefore, be recognized as when the increased absorption of 850 nm light 1022 begins to occur, while the absorption of light 1020 at 685 nm continues to decrease, then holds steady.

FIGS. 11A-B illustrates an Energy Conversion Index data from an Ischemia/Reperfusion spectral absorption test using broadband light illumination of forearm skin and a spectrometer for signal detection. Spectrometer-detected light intensity values at 685 nm and at 850 nm were selected from the recorded spectrometer data file, as shown in FIG. 12, and were used as the Raw Data to compute the Energy Conversion Index value trend 1110. In FIG. 11A, an Energy Conversion Index value trend 1110 is measured on the Y-axis and Time is measured on the X-axis. In FIG. 11B detected light Intensity at 850 nm 1104 and at 685 nm 1106 is measured on the Y-axis and Time is measured on the X-axis. This is a brief, harmless, and easily reproduced demonstration simulating the blood volume and tissue chemistry dynamics that likely also occur during occlusion, then during reperfusion, of blood supply to vital organ tissue, such as with ischemic heart attack, ischemic stroke, or reperfusion of transplant organs. This test uses a pneumatic cuff on the subject's upper arm to stop blood flow to and from the forearm for three minutes, followed by sudden release of the cuff pressure to allow blood flow to resume. The test uses a spectrometer (Ocean Optics, Flame-S) for signal detection, via optical fiber, of unabsorbed light after broadband light, via optical fiber (Ocean Optics QTH lamp), has passed through 8 mm of the subject's forearm skin. Spectral light intensity data from 600 nm to 1000 nm are detected and recorded once per second. A pre-test reference spectrum is subtracted from each sample spectrum, element by element, and the difference spectrum data values are recorded. If no change in absorption has occurred in the forearm skin during the recording, the resulting spectral intensity variation data will be near-zero throughout.

The data in FIG. 11A is calculated by subtracting the recorded 850 nm infrared intensity values 1104 from the time-corresponding 685 nm red intensity values 1106, as shown in FIG. 11B, producing the Energy Conversion Index value trend 1110. The infrared wavelength has been found to be the most sensitive to the volume of blood, mostly venous, within the light path. As the cuff is rapidly inflated 1112, blood flow into and from the forearm is completely stopped, resulting in the 850 nm data trend of the infrared intensity values 1104 changing very little. The 685 nm red value trend for the red intensity values 1106, on the other hand, shows continuously increasing absorption (decreasing detected signal intensity) during the entire cuff inflation period 1114. Time point "A" 1116 is just prior to releasing cuff pressure and "B" 1118 is shortly after cuff pressure is released 1120 when the signals have stabilized again.

Upon release of the cuff pressure 1120, the arterial flow into the forearm resumes before venous blood is allowed to begin leaving the forearm, resulting in a small amount of additional blood briefly accumulating in the forearm, and causing a slight dip in the 850 nm trend 1122. The 685 nm intensity value 1124, on the other hand, very rapidly rises to a much higher value 1126 than prior to cuff inflation, indicating less absorption at 685 nm by the skin, as also occurs when a person breathes 100% oxygen; i.e. cellular hyperoxia. Simultaneous recording of pulse oximetry during this test typically shows only slight, to no, change in $SpO_2$ from beginning to end of the test. The combination of much less absorption at 685 nm than before the test and slightly more absorption at 850 nm upon reperfusion, with no change in arterial blood oxygen saturation by pulse oximetry, is presented as evidence that blood oxygen saturation plays only a very minor role. The recorded large variations in spectral optical density during this test are, therefore, likely mostly due to changes in cellular chemistry. The main implication of this simple demonstration is that reperfusion injuries to vital organs in adults, and the eye, brain, and gut injuries that occur with premature newborn infants, are likely to be a consequence of previously unknown, or under-appreciated, cellular adaptation to lower oxygen supply. Cellular energy conversion mechanisms, such as mitochondrial transport within cells, appear from experiments such as this one to be much more time-efficient in adapting to a sudden decrease in oxygen supply than to a sudden increase in oxygen supply. Current research of ischemia/reperfusion injury (IRI) clearly defines the first few seconds of reperfusion, rather than during the previous ischemic or hypoxic period, as when the major problems begin to appear, such as the adhesion of white blood cells in capillaries and venules, leading to obstruction of blood flow that ultimately causes cellular death in the surrounding tissue.

Figure 12A:
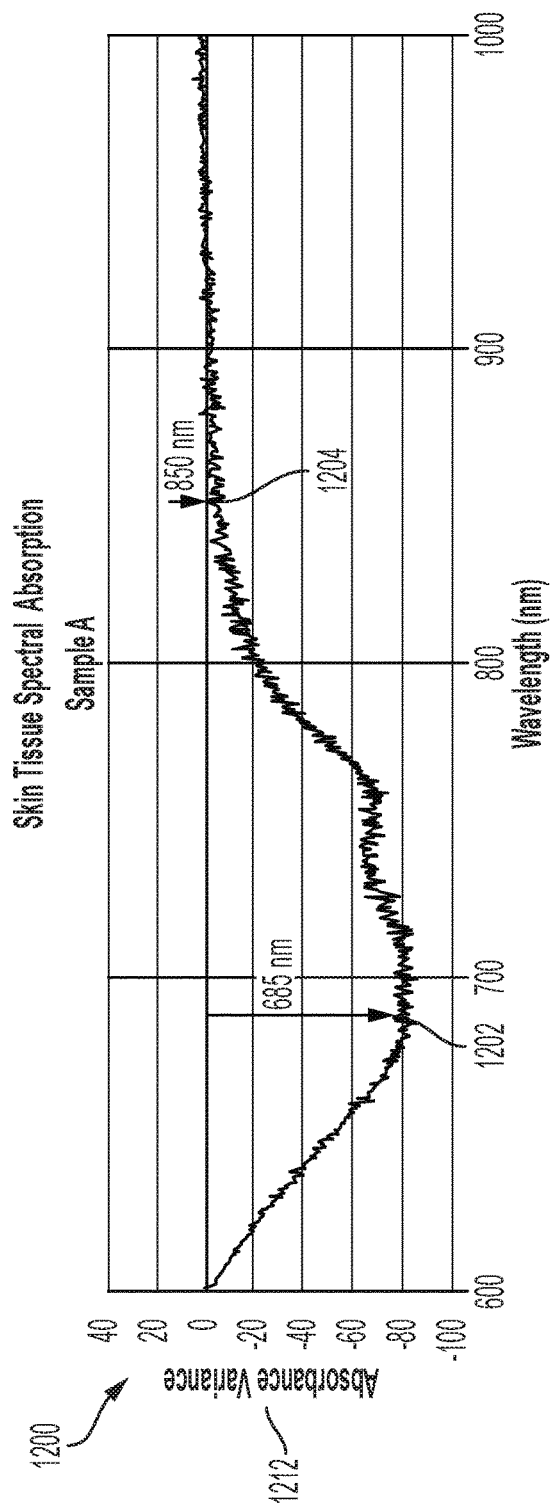
FIGS. 12A-B illustrate exemplar graphs of skin absorbance spectral variation at just prior to and just following blood reflow taken from spectrometer recording.
Figure 12B:
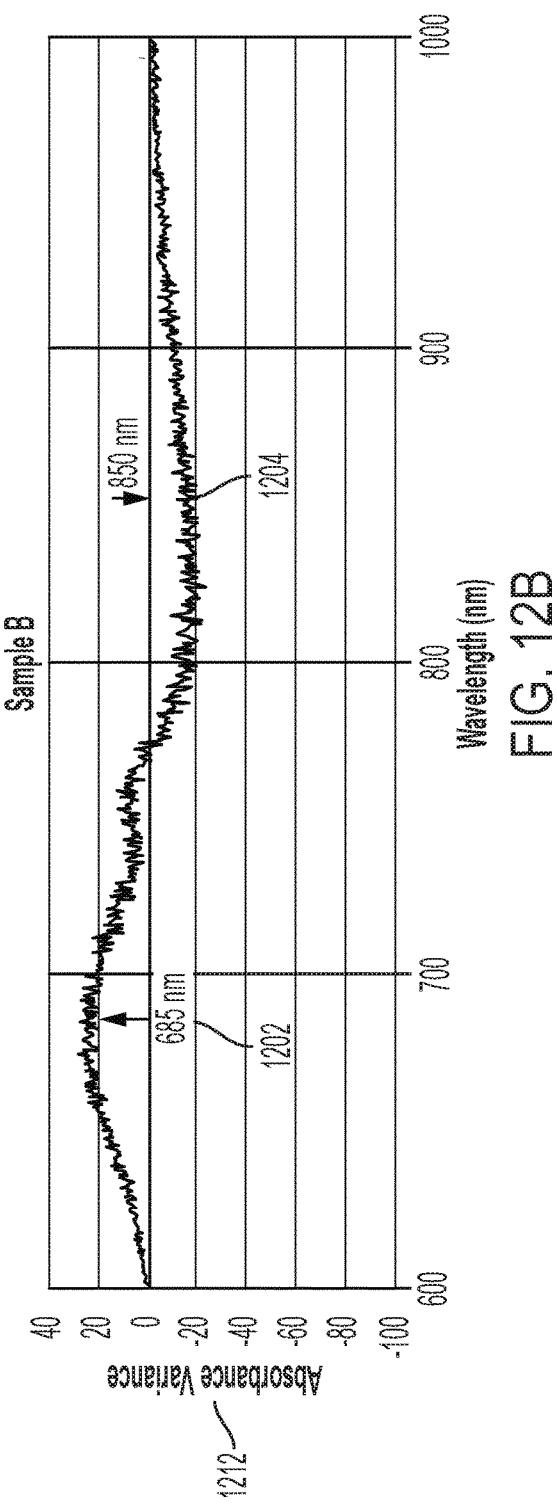

FIGS. 12A-B illustrates an exemplar skin spectral absorbance variation at just prior to and just following blood reflow, as an alternate portrayal of the test data depicted in FIGS. 11A-B. FIGS. 12A-B show the Absorbance Variation (Y-axis), or net change in spectral absorbance, over a range of wavelengths from 600 nm to 1000 nm (X-axis) for two data samples: Sample A and Sample B. These spectral recordings were used to help select the most active regions of the spectrum relative to varying cellular oxygen supply to the skin. In the extreme case of completely stopped blood flow, or ischemia, the cellular chemistry impact is theoretically greatest, lending confidence that this test is likely the best method to define the sensor wavelengths. The spectral graph of Sample A 1200 that was recorded just prior to releasing the cuff shows the maximum Absorbance Variance 1202 at about 685 nm. The infrared wavelength, on the other hand, is most impacted immediately following reperfusion in Sample B, where maximum Absorbance Variance 1212 shift occurs at about 850 nm 1204.

Figure 13A:
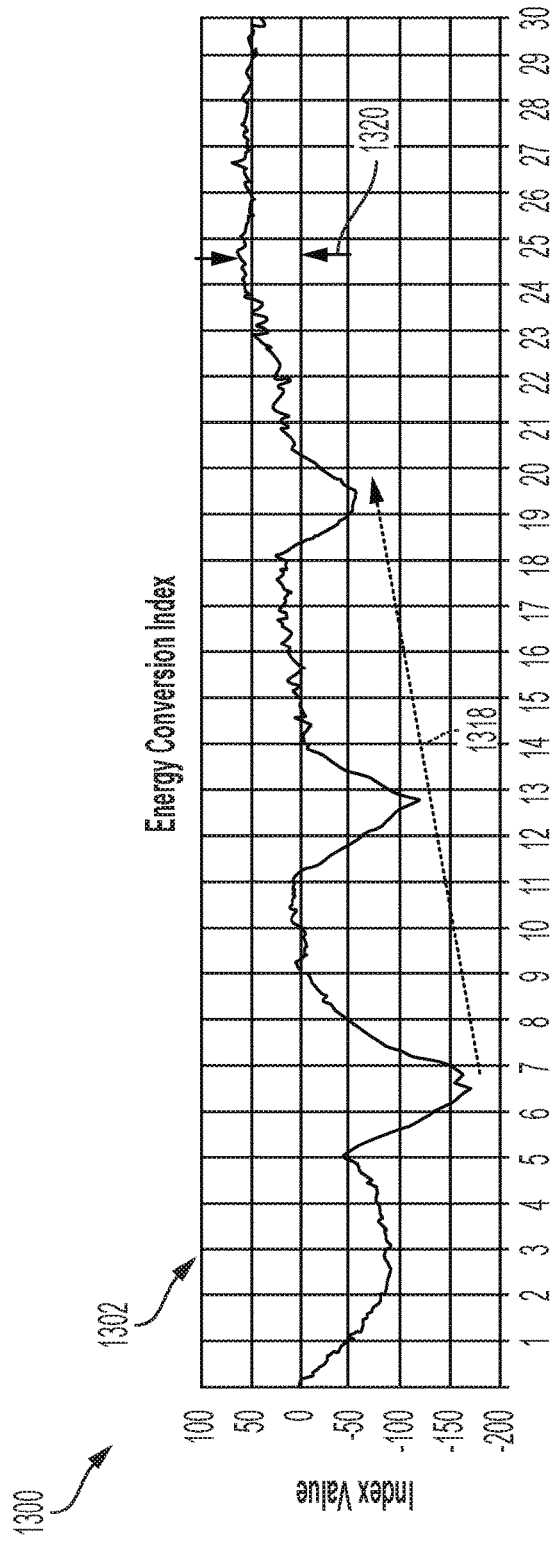
FIGS. 13A-D illustrate exemplar graphs of exercise recording of ECi, Raw Data, Heart Rate, and $SpO_2$ trends taken from the sensor monitoring device.
Figure 13B:
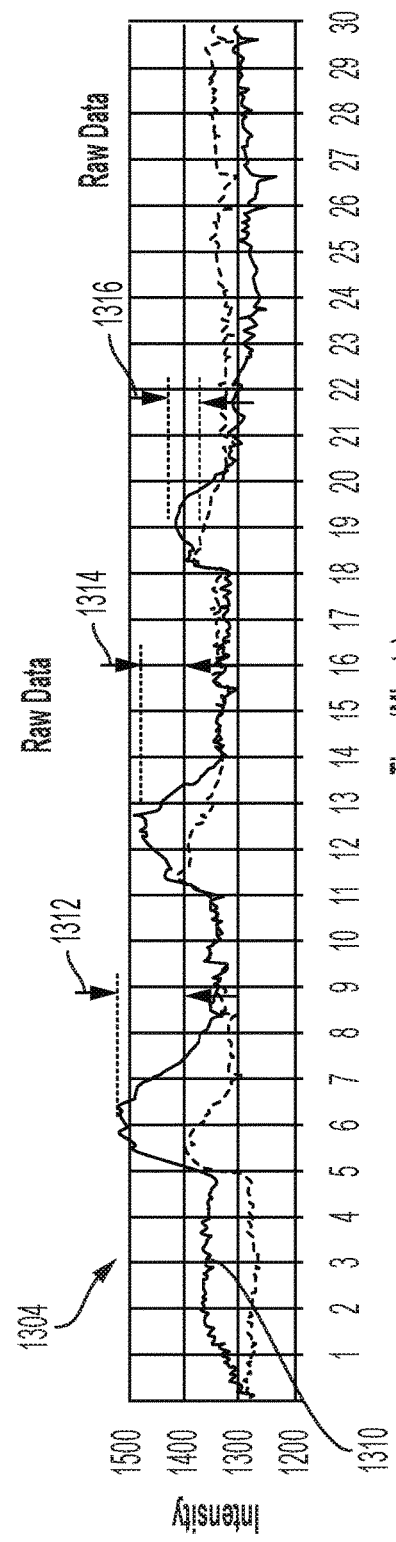
Figure 13C:
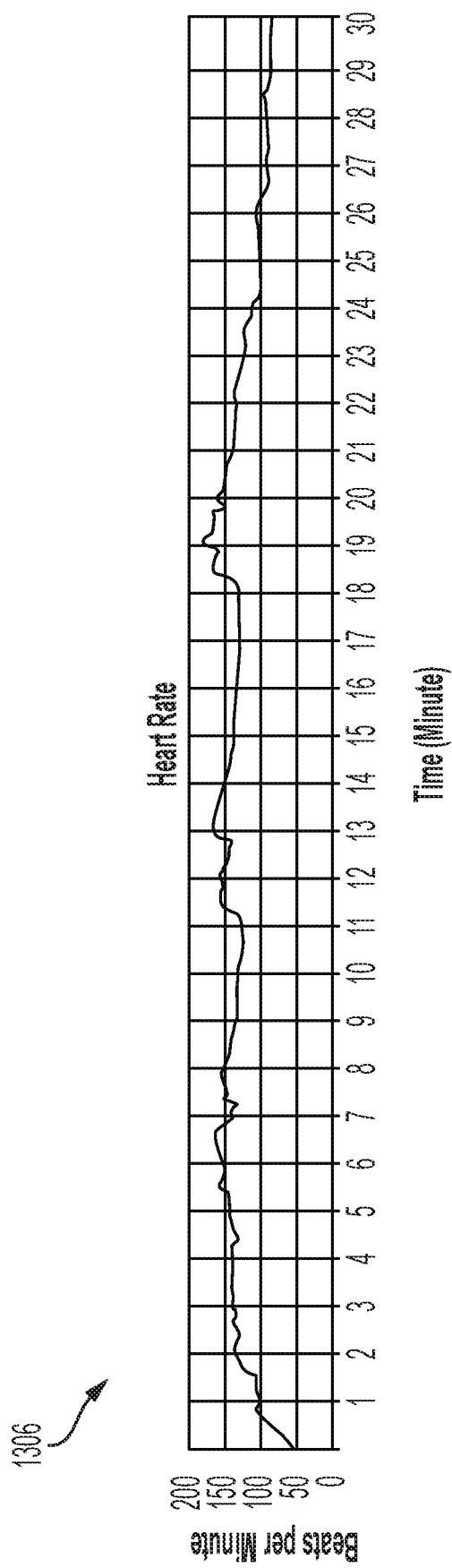
Figure 13D:
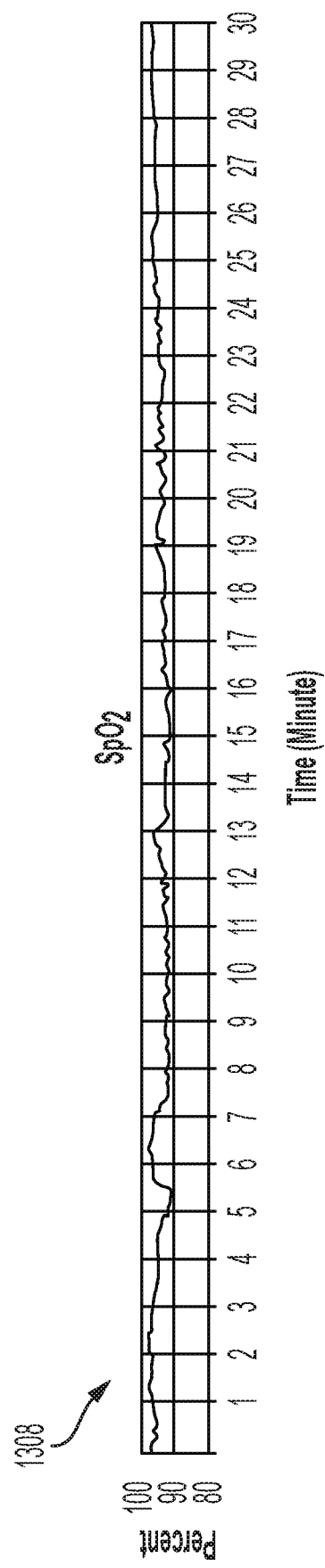

FIGS. 13A-D illustrate results of an exemplar exercise recording 1300 of Energy Conversion Index (ECi) 1302, Raw Data 1304, PPG Heart Rate 1306, and $SpO_2$ 1308 trends. FIG. 13A shows an Index Value (Y-axis) over time (X-axis); FIG. 13B illustrates an Intensity (Y-axis) over time (X-axis); FIG. 13C shows Beats per Minute (Y-axis) over time (X-axis); and FIG. 13D shows $SpO_2$ percentage (Y-axis) over time (X-axis). This data was obtained simultaneously from an adult athlete during a stationary bicycle exercise session. The Raw Data 1304 shown in FIG. 13B shows a decrease in absorption (higher signal intensity) of the sensor's 850 nm light 1310 relative to the degree of exertion. The normal hypoxic stress induced by exercise is known to drive reflex vasoconstriction of the blood supply to the skin to conserve cardiac output and total body oxygen consumption to preferentially sustain the vital organs: brain and heart. As less blood is conveyed to the skin, there is less absorption of the sensor's light; more prominently seen with the infrared wavelength 1310. With each of the three intervals of increased effort, there is also a progressive change in the absorption of the red, vs. the infrared light that appears to correlate with an adaptation response to hypoxic stress that appears to be uniquely and robustly detected by the present disclosure. Progressively less prominent differential responses 1312, 1314, and 1316 are seen in the Raw Data 1304 despite the exertion levels being similar, as shown by the heart rate responses in FIG. 13C, resulting in an overall ECi trend 1318 toward the pattern seen with excess cellular oxygen delivery, or skin hyperoxia 1320. Notably, there is virtually no variation in the $SpO_2$ data in FIG. 13D during and following the exercise session in this healthy athlete. Apparently, the combination of invoked physiologic stabilizing reflexes resulted in fully sustained blood oxygen supply to the athlete's brain, heart, and muscles during this exercise session.

Figure 14A:
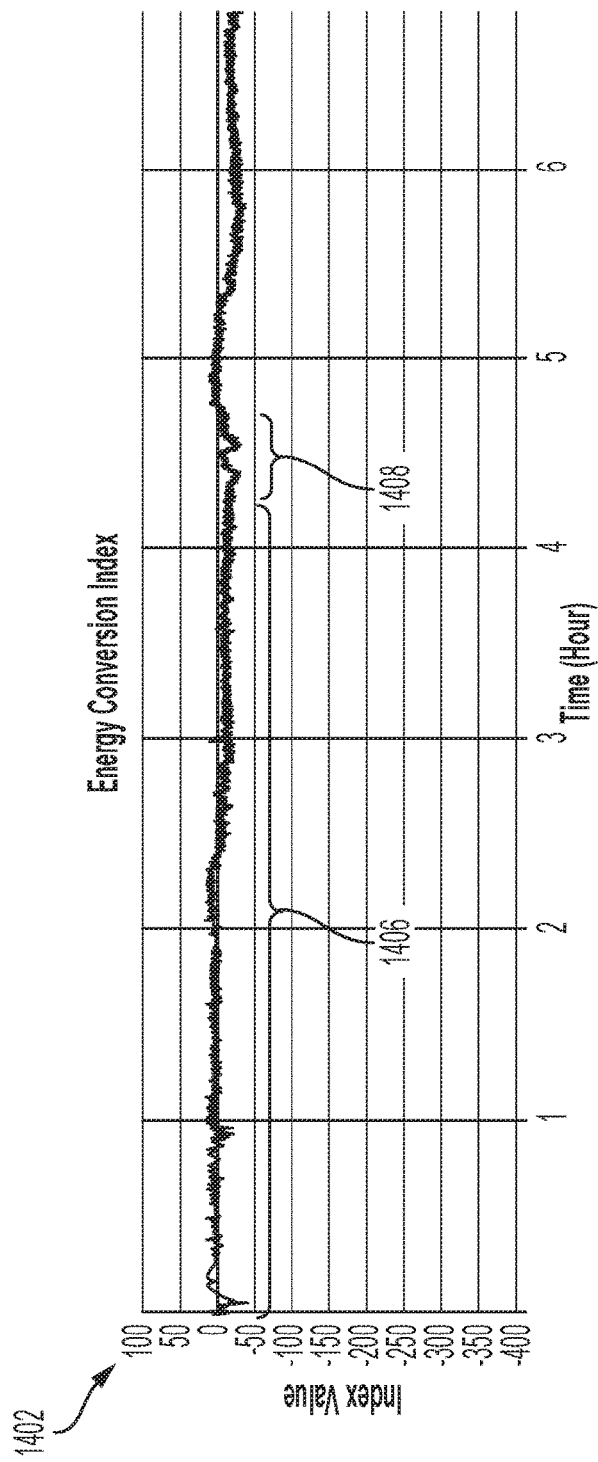
FIGS. 14A-B illustrate exemplar graphs of recording during normal sleep breathing taken from the sensor monitoring device.
Figure 14B:
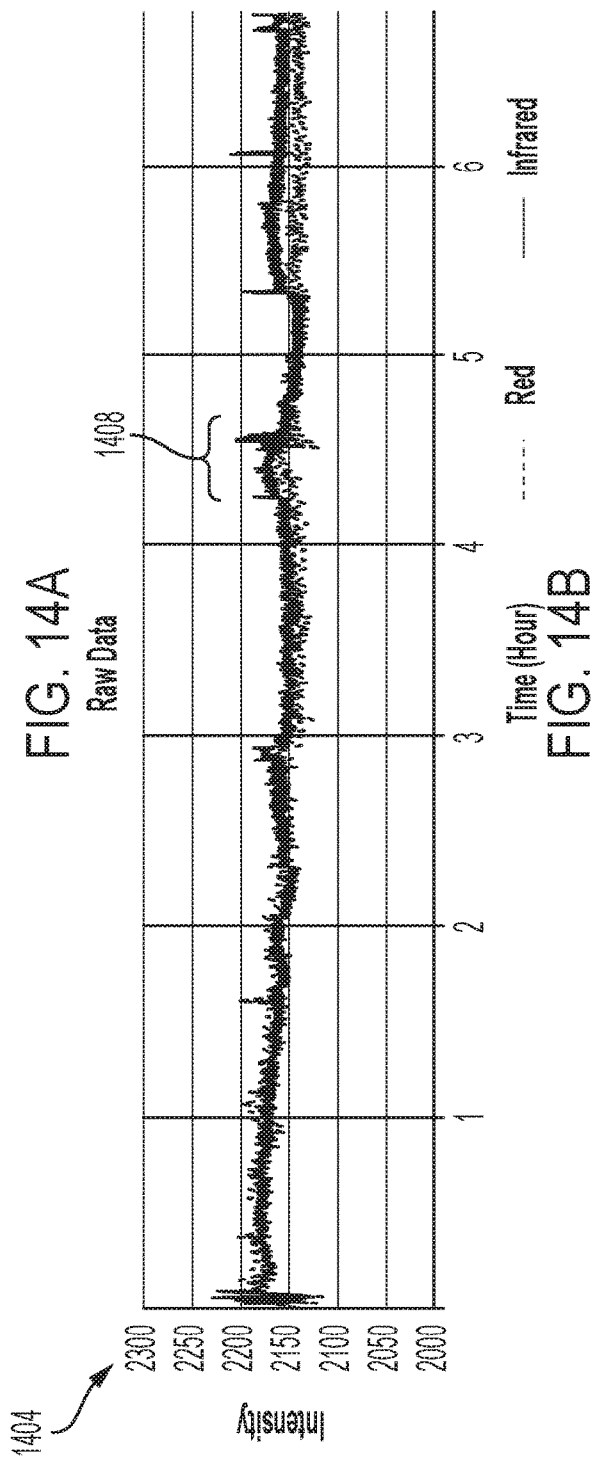

FIGS. 14A-B illustrate exemplar recordings during normal sleep breathing. FIG. 14A is a 6:50-hour segment of an Energy Conversion Index sleep recording 1402 that portrays the level of oxygen supply to the skin under the sensor, relative to the person's normal, acclimated status while awake. FIG. 14B is the Raw Data 1404 from which the Energy Conversion Index sleep recording 1402 was computed. This person is known to not snore and to sleep soundly all night. The first four hours of sleep 1406, were undisturbed by breathing difficulty. Only brief episodes of minimal activity are seen in the ECi and Raw Data trends 1408 and, since these variations are mostly tandem, they do not show a significant decrease in oxygen supply to the subject's skin.

Figure 15A:
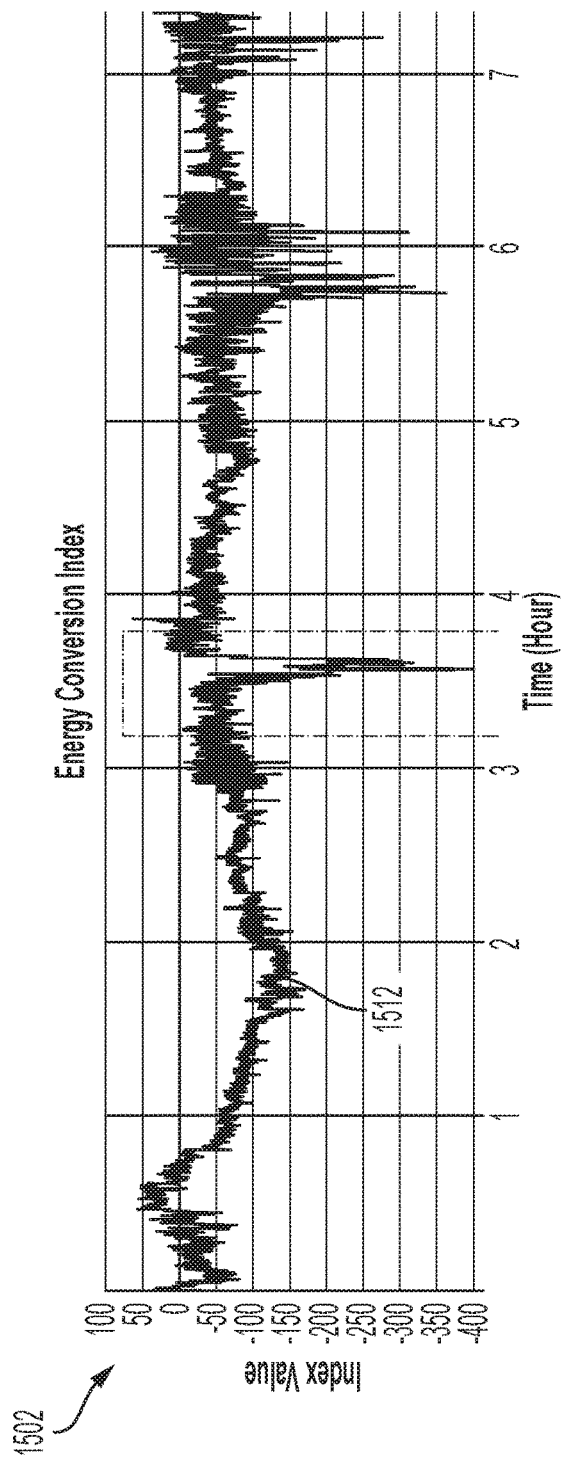
FIGS. 15A-B illustrate exemplar graphs of recording during sleep disordered breathing taken from the sensor monitoring device.
Figure 15B:
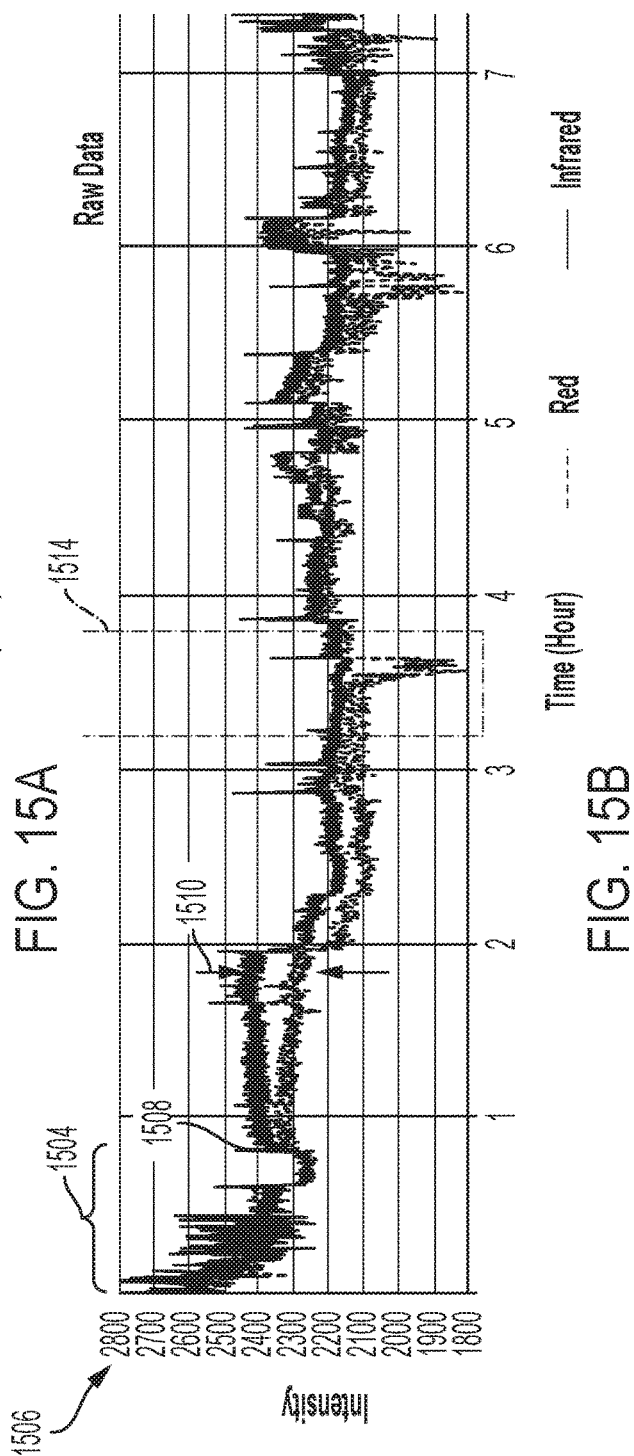

FIG. 15A-B illustrate exemplar recording during severe sleep disordered breathing. FIG. 15A is a 7-hour Energy Conversion Index recording 1502 showing several of the abnormal responses that may occur during sleep. The initial hour 1504 of Raw Data 1506 typically follows a tandem downward trend, as evidence of the shift of total body blood volume to become distributed throughout the recumbent length of the body. During the remainder of the night, the Raw Data baseline typically tandemly shifts up, or down 1508, depending on the side-to-side position of the subject's body. FIG. 15B shows in the Raw Data 1506 record corresponding to FIG. 15A that when the sensor is on the arm lower than the subject's heart, the Raw Data 1506 baseline is lower due to more venous blood being present in the skin of the arm being monitored. The converse occurs when the subject rolls over and sleeps with the sensor above the heart. Decreased skin tissue oxygen supply is detected by a differential 1510 of the red trend less than the infrared trend, which results in a negative-going Energy Conversion Index trend 1512.

It is apparent that difficulties with breathing during sleep are not consistent throughout the night. Of note is the outlined episode 1514 during which the subject's access to oxygen was severely affected by a problem with breathing. This data segment is expanded in FIGS. 15C-D.

FIGS. 15C-D illustrates outlined episode 1514 segment from FIGS. 15A-B during restricted and periodic breathing. The oscillating ECi pattern typically seen with periodic breathing 1516 is the most prominent feature of this segment. Periodic breathing during sleep is characterized by a moderately restricted airway that typically produces snoring sounds. The research literature describes sleep deprivation as a reason for decreased sensitivity to low oxygen intake during periodic breathing. This decreased sensitivity results in delayed responses to hypoxic stress, with repeating cycles of deeper 'catch-up' breathing, due to increased loop gain, typically, at 25- to 35-second intervals. The Raw Data infrared trend baseline 1518 in this record remains relatively constant, while the red trend 1520 makes periodic dips, indicating that the oxygen supply to the skin is periodically lower than normal. A 10-minute episode of widely varying and more extreme airway restriction 1522 is apparently interrupted by an obstruction event 1524 that arouses the person to a lighter stage of sleep and less severe airway restriction.

Figure 16A:
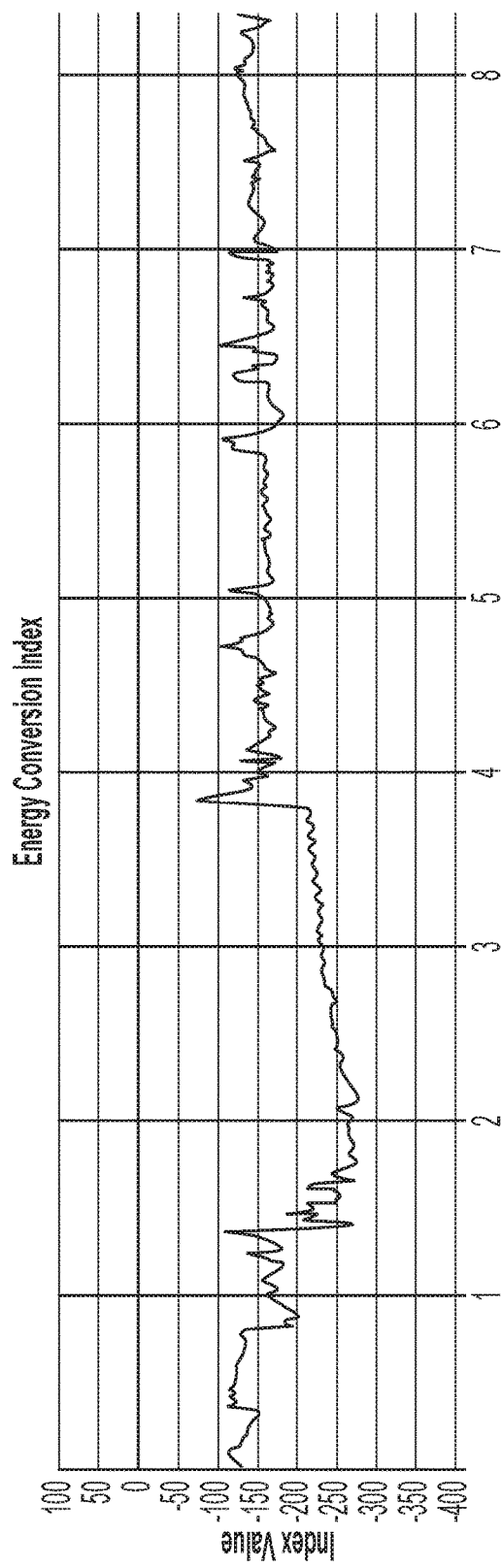
FIGS. 16A-B illustrate exemplar recordings during sleep disordered breathing; obstructive and central apnea taken from the sensor monitoring device.
Figure 16B:
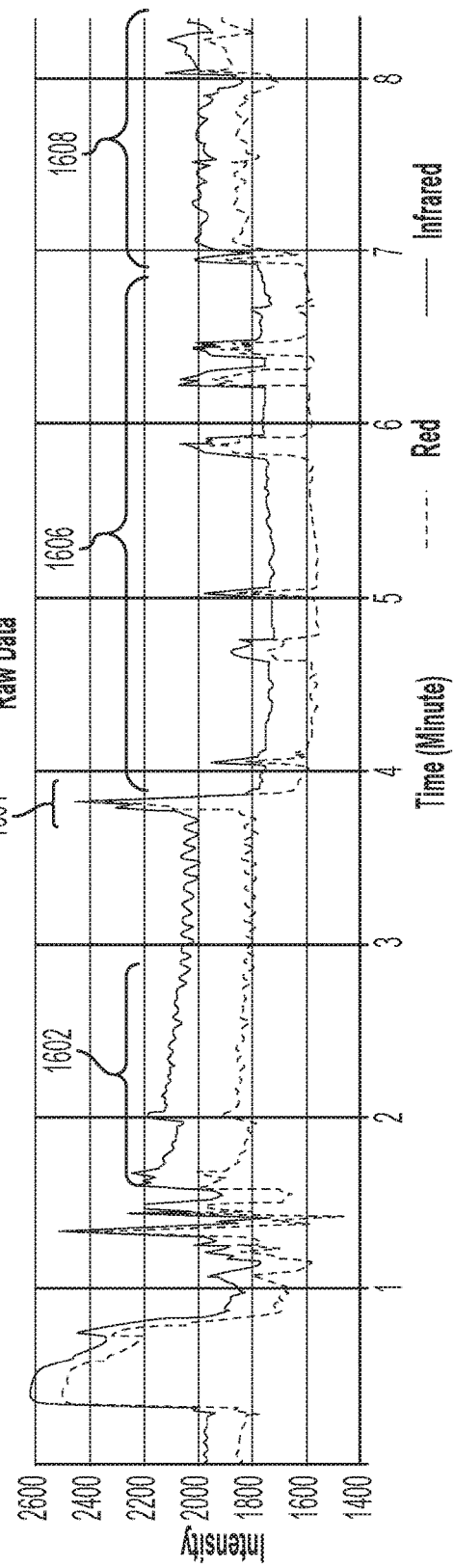

FIGS. 16A-B illustrate an exemplar recording during severe sleep disordered breathing with both obstructive and central apnea. The recording covers an 8-minute segment during an extended sequence of severe airway obstructive episodes during sleep. The first two minutes of the record show large tandem variations in the Raw Data typical of activity with severe airway distress, resulting in a sharply decreasing Energy Conversion Index trend. Beginning at minute-2, there is a period 1602 of reduced breathing drive, or central apnea, accompanied by significant skin hypoxia down to about −275 on the Energy Conversion Index scale. This period of apnea is followed by regular, apparently unobstructed breathing that results in a gradual Energy Conversion Index recovery trend toward normal oxygen supply to the skin, but that is interrupted by a major obstructive event 1604. Following this airway obstruction event, there is a 3-minute period 1606 of central apnea mixed with large breath efforts against a mostly-obstructed airway, resulting in moderate skin hypoxia. This recording segment ends with irregular breathing against a less-restricted airway 1608, but little improvement in oxygen intake.

Figure 17A:
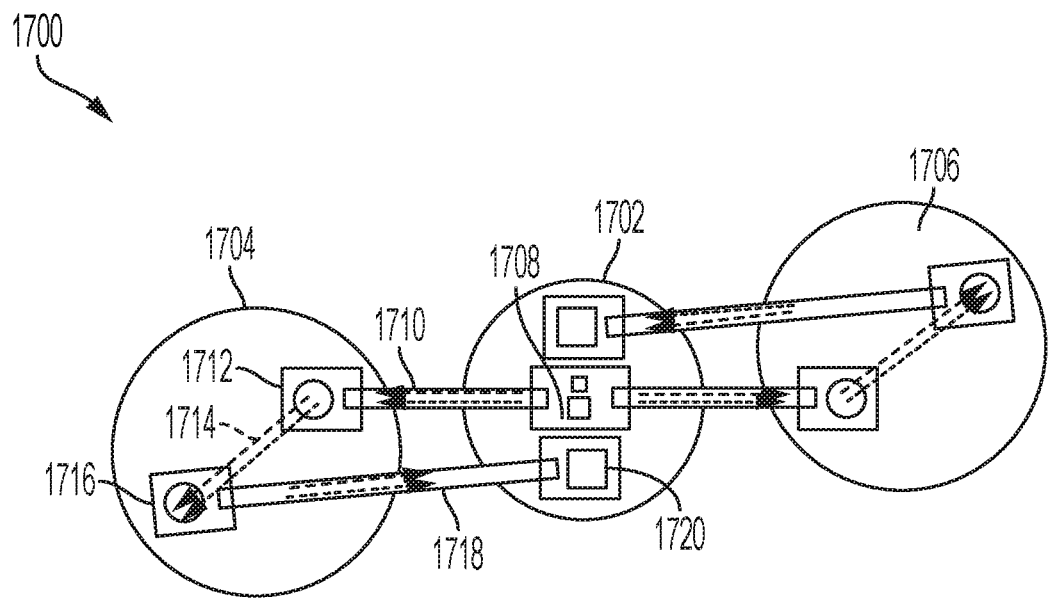
FIGS. 17A-B illustrate an exemplar dual-probe sensor.
Figure 17B:
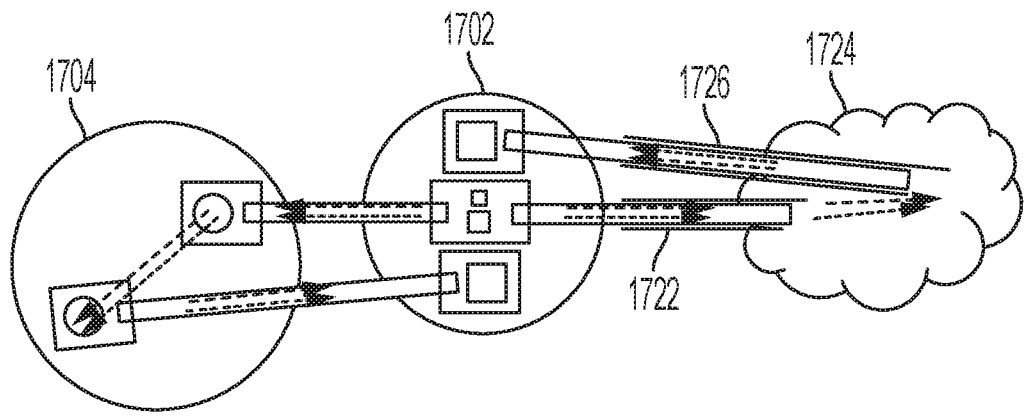

FIG. 17A illustrates an exemplar dual-probe sensor 1700 consisting of a central hub 1702, connected to a first skin contact probe assembly 1704 and a second skin contact probe assembly 1706. The first skin contact probe assembly 1704 and a second skin contact probe assembly 1706 are connected by optical fibers. Two LEDs, 685 nm, and 850 nm 1708 project light alternately via a first optical fiber 1710 to a mirror and aperture 1712 that projects the light into the tissue on which the first skin contact probe assembly 1704 is placed. The light diffuses through the tissue 1714 and a sample of the light that is not absorbed is conveyed by a second optical fiber 1718 to a photodetector 1720. Light is simultaneously also conveyed to and from the second skin contact probe assembly 1706 and detected in like manner by a second detector. Simultaneous illumination of both the first skin contact probe assembly 1704 and the second skin contact probe assembly 1706 with the same center wavelengths of LED light is needed to reduce ambiguity of the differential results. This configuration may be used noninvasively for two skin application sites, such as pre- and post-ductal sites on the right upper chest and left lower abdomen of a newborn premature infant, respectively. By this means, the pre-ductal probe data will indicate the highest oxygen supply status, and the post-ductal probe the lowest. This information may be used to guide initial and continuing oxygen fraction in the breathing gas and to indicate when the ductus closes; or if it does not close in a timely fashion and becomes problematic. This configuration may also be applied with the first skin contact probe assembly 1704 placed on the skin of the organ recipient, as a 'normal standard,' and the second skin contact probe assembly 1706 placed on the transplant organ at the time of reperfusion and surgical implantation of the organ to monitor the reperfusion and resupply of oxygen to the transplant organ. An alternative embodiment in FIG. 17B would have the same configuration of the first skin contact probe assembly 1704 for placement as a 'normal standard' on the patient's skin, and the optical fibers to 1722 and from 1724 the monitored tissue 1726 interfacing with the tissue via needles inserted in the tissue. This format may be more useful when access to the monitored tissue is limited, or when surgical access for placement of an organ surface contact probe needs to be avoided.

Once the ECM device engages the patient' skin, the aforementioned initialization and operation of the sensor is performed. Detecting the unabsorbed light from the emitted light after the light has passed through the skin is performed with a light detector. Once the unabsorbed light is detected, a differential photonic absorption effect is computed, determining a skin hypoxia level. The light detector, such as a silicon PIN photodiode, detects both 685 nm and 850 nm light in a known spectral response manner. The method can also include providing feedback-control of the operation of the ECM device. Feedback-control includes, but is not limited to increasing or decreasing the intensity of an emitted light. The method can also include producing an Energy Conversion Index output by subtracting a first detected intensity from an 850 nm light from a second detected intensity from a 685 nm light.

In another method, the ECM device is used in conjunction with an airway therapy apparatus. The airway therapy apparatus, such as a CPAP device or APAP device, has a blower, a patient interface, an air delivery conduit for delivering air from the blower to the patient interface, a sensor for determining the pressure in the patient interface, and a control mechanism that causes air to be delivered at a desired pressure to the patient interface and that detects transitions between inhalation and exhalation of a respiratory cycle of a patient in order to synchronize the blower output with the patient's efforts. The method includes transmitting data from the ECM device to the airway therapy apparatus. The data from the ECM device can be transmitted directly to the airway therapy device, indirectly to the airway therapy device, wirelessly to the airway therapy device, or wired to the airway therapy device. The data from the ECM device can be used to change the operation of the airway therapy device. In other methods, the data from the ECM device can be analyzed at a remote central location, and then instructions for operation of the airway therapy device can be sent to the airway therapy device to adjust performance of the airway therapy device during the same, or during a next use by the patient.

In another method, the ECM device is used in conjunction with PSG testing instrumentation. The PSG testing instrumentation includes the use of sensors and equipment to monitor brain waves, eye movements, heart rate, breathing pattern, blood oxygen level, body position, chest and abdominal movement, limb movement, snoring and other sounds. The method includes transmitting data from the ECM device to a central computing device receiving information related to the polysomnography test. The data from the ECM device can be transmitted directly, indirectly, wirelessly, or wired. The data from the ECM device can be used to facilitate diagnosis of SDB. The same methods of using the ECM device can also be applied to the use of home sleep apnea testing, either by itself, or in conjunction with other equipment.

The systems and methods according to aspects of the disclosed subject matter may utilize a variety of computer and computing systems, communications devices, networks, and/or digital/logic devices for operation in combination with the disclosed sensors. Each may, in turn, be configurable to utilize a suitable computing device that can be manufactured with, loaded with, and/or fetched from some storage device, and then execute, instructions that cause the computing device to perform a method according to aspects of the disclosed subject matter.

A computing device can include without limitation a mobile user device such as a mobile phone, a smartphone and a cellular phone, a personal digital assistant (PDA), such as an iPhone®, a tablet, a laptop and the like. In at least some configurations, a user can execute a browser application over a network, such as the Internet, to view and interact with digital content, such as screen displays. A display includes, for example, an interface that allows a visual presentation of data from a computing device. Access could be over or partially over other forms of computing and/or communications networks. A user may access a web browser, e.g., to provide access to applications and data and other content located on a website or a webpage of a website.

A suitable computing device may include a processor to perform logic and other computing operations, e.g., a stand-alone computer processing unit (CPU), or hard-wired logic as in a microcontroller, or a combination of both, and may execute instructions according to its operating system and the instructions to perform the steps of the method, or elements of the process. The user's computing device may be part of a network of computing devices and the methods of the disclosed subject matter may be performed by different computing devices associated with the network, perhaps in different physical locations, cooperating or otherwise interacting to perform a disclosed method. For example, a user's portable computing device may run an app alone or in conjunction with a remote computing device, such as a server on the Internet. For purposes of the present application, the term "computing device" includes any and all of the above discussed logic circuitry, communications devices and digital processing capabilities or combinations of these.

Certain embodiments of the disclosed subject matter may be described for illustrative purposes as steps of a method that may be executed on a computing device executing software, and illustrated, by way of example only, as a block diagram of a process flow. Such may also be considered as a software flow chart. Such block diagrams and like operational illustrations of a method performed or the operation of a computing device and any combination of blocks in a block diagram, can illustrate, as examples, software program code/instructions that can be provided to the computing device or at least abbreviated statements of the functionalities and operations performed by the computing device in executing the instructions. Some possible alternate implementation may involve the function, functionalities and operations noted in the blocks of a block diagram occurring out of the order noted in the block diagram, including occurring simultaneously or nearly so, or in another order or not occurring at all. Aspects of the disclosed subject matter may be implemented in parallel or seriatim in hardware, firmware, software, or any combination(s) of these, co-located or remotely located, at least in part, from each other, e.g., in arrays or networks of computing devices, over interconnected networks, including the Internet, and the like.

The instructions may be stored on a suitable "machine readable medium" within a computing device or in communication with or otherwise accessible to the computing device. As used in the present application a machine-readable medium is a tangible storage device and the instructions are stored in a non-transitory way. At the same time, during operation, the instructions may at sometimes be transitory, e.g., in transit from a remote storage device to a computing device over a communication link. However, when the machine readable medium is tangible and non-transitory, the instructions will be stored, for at least some period of time, in a memory storage device, such as a random access memory (RAM), read only memory (ROM), a magnetic or optical disc storage device, or the like, arrays and/or combinations of which may form a local cache memory, e.g., residing on a processor integrated circuit, a local main memory, e.g., housed within an enclosure for a processor of a computing device, a local electronic or disc hard drive, a remote storage location connected to a local server or a remote server access over a network, or the like. When so stored, the software will constitute a "machine readable medium," that is both tangible and stores the instructions in a non-transitory form. At a minimum, therefore, the machine readable medium storing instructions for execution on an associated computing device will be "tangible" and "non-transitory" at the time of execution of instructions by a processor of a computing device and when the instructions are being stored for subsequent access by a computing device.

Additionally, a communication system of the disclosure comprises: a sensor as disclosed; a server computer system; a measurement module on the server computer system for permitting the transmission of a measurement from a detection device over a network. Communications capabilities also include the capability to communicate and display relevant performance information to the user, and support both ANT+ and Bluetooth Smart wireless communications. A storing module on the server computer system for storing the measurement in a detection device server database can also be provided. In some system configurations, the detection device is connectable to the server computer system over at least one of a mobile phone network and an Internet network, and a browser on the measurement recipient electronic device is used to retrieve an interface on the server computer system. In still other configurations, the system further comprising: an interface on the server computer system, the interface being retrievable by an application on the mobile device. Additionally, the server computer system can be configured such that it is connectable over a cellular phone network to receive a response from the measurement recipient mobile device.

Examples of Use

The examples of use relate to the use of a disclosed ECM sensor alone or as part of a system with one or more secondary devices. The secondary device can be selected from a second sensor, a sleep disordered breathing (SDB) therapy device, a remote computing device, and a polysomnograph (PSG) system.

Additionally, operation of the ECM sensors or systems can be controlled by the user directly (i.e. by interfacing with the sensor) or via a software application on a mobile computing device such as a smart phone or tablet configured to wirelessly control the ECM sensor. In other configurations, the ECM sensors or systems can be operated via a remote computing device which communicates wirelessly with the ECM sensor (e.g. from a clinic or healthcare practitioner facility).

Sleep Disordered Breathing

In one example, a disclosed sensor may be used to help diagnose sleep disordered breathing (SDB). The clinical utility of the disclosed ECM sensors for diagnostic testing of adults for SDB has been validated in proof of concept (POC) PSG sleep studies at the UCSF Sleep Disorders Center, Mt. Zion Hospital, San Francisco. The disclosed ECM sensors have also been found to be suitable for remote SDB testing at home. The UCSF POC sleep studies documented that the ECM detection of cellular hypoxia in the skin during prolonged periods of snoring was a significant new finding that can potentially be used by healthcare professionals to better understand and define the physiologic mechanism(s) of the elevated statistical risk of SDB co-morbidities, such as hypertension, atrial fibrillation, heart attack, stroke, and early-onset dementia. The PSG pulse oximeter data during the POC studies did not detect a 'scorable' drop (e.g. 3% or more decrease) in $SpO_2$ during most of the snoring episodes, and only showed a decline in arterial blood oxygen during the more severe and prolonged episodes of OSA and CSA. PSG instrumentation currently only includes pulse oximetry as a means of monitoring oxygen intake.

As will be appreciated by those skilled in the art, PSG measurement of breathing movement uses stretch-sensitive straps around the chest and abdomen and an air flow sensor placed by the nose to provide a rough estimate of the effort needed for each breath and how that effort relates to the movement of air in-and-out of the lungs. A more effective mechanism for measuring breathing effort is the use of an intra-esophageal balloon manometer to track the intra-thoracic pressure. However, this approach is quite uncomfortable and is seldom used clinically. The additional capability of the disclosed ECM sensor to non-invasively detect the timing and relative effort of each breath improves and simplifies the detection of OSA vs. CSA vs. the current PSG system. The UCSF POC study demonstrated that the ECM raw data also clearly distinguishes between OSA and CSA by the infrared channel's detection of breathing rate and breathing effort. Venous blood is known to flow in-and-out of central chest veins, and correspondingly also peripheral veins, with each breath. This breathing-cyclic venous blood flow is the physiologic basis of pulsus paradoxus, where cardiac output and systolic blood pressure vary in synchrony with breathing cycle-induced changes in intrathoracic pressure. The infrared channel data of the ECM photonically detects the subtle variations in venous blood volume in the skin at the sensor site on the upper arm as a cyclic variation in signal intensity at the infrared wavelength. This provides a non-invasive 'venous pneumogram' of intra-thoracic pressure—likely comparable in quality and sensitivity to invasive intra-esophageal balloon manometry.

Recorded data from each night's ECM sensor use at home can be conveyed, e.g., by cell phone data transmission to a 'back-end' service center where qualified and licensed sleep medicine sub-specialist physicians will review the data and, if indicated by their assessment, return a prescription for an airway therapy device to the person's physician and respiratory therapist. The sleep medicine expert reading the home diagnostic testing data may, based on expert assessment, recommend the person undergo a formal PSG sleep study for further evaluation of complex cases, such as those with underlying neurologic disease, seizure/s that occur during the sleep record, and other disabilities that may adversely affect the quality of the diagnosis and possibly call for more complex therapy of SDB.

In another related application, the disclosed sensors may be used to record body position of adults suffering from SDB during sleep at home. Adults typically have more severe OSA and snoring when sleeping on their back. Virtually all sleep recordings with the ECM show an initial period of about one hour when venous blood redistributes from being mainly in the lower trunk and legs while upright to being more evenly distributed throughout the length of the recumbent body (i.e. rostral shift) during sleep. Also, when a sleeping person with an ECM applied to the upper arm rolls from side to side, there is a further shift in venous blood volume in the skin beneath the sensor, resulting in a large, abrupt, tandem shift of both red and infrared signals depending upon which side the person is laying on. Therefore, continuous detection of body position and posture during sleep is needed and, in the present disclosure, can be further documented by system-integration with a micro electro-mechanical system (MEMS) accelerometer.

In a related application, the disclosed sensors may be used to remotely guide titration of SDB therapy at home, such as with an APAP machine, to optimally titrate the patient's therapy while sleeping at home. The airway therapy equipment currently used for titration of airway therapy in a sleep lab uses more advanced sensors and controls than are typically found in the airway therapy equipment prescribed for home use. Sleep lab technicians performing the therapy titration also have real-time access to the full PSG array of instrumentation, along with infrared video surveillance of the person being tested. This higher quality and completeness of information helps the sleep testing technician manage the therapy during the titration session. The home airway therapy device prescription from the sleep medicine specialist is largely derived from the observations and recorded data from this procedure. However, due to the differences between the clinical and home-use therapy equipment, the sleep lab therapy titration, and the derived prescription of settings for the home-use machine, may not produce optimal results with the home-use machine. Remote titration with the disclosed sensor is more likely to succeed in initially, and subsequentially, optimizing home therapy.

In another related application, the disclosed sensors may be used to help control SDB therapeutic equipment in the patient's home. Compared with the full PSG system, including a trained sleep testing technician and a clinical quality APAP machine, existing home airway therapy equipment is significantly limited in its sensitivity and specificity of detection of SDB events. Typically, home APAP machines cannot clearly distinguish between OSA, snoring, and CSA events because the machines are limited to sensing the airway pressure and air flow via the hose from the machine to the patient's nose mask or facemask. OSA and snoring typically resolve better with increased airway pressure. Prolonged pauses in breathing (e.g., CSA), on the other hand, usually respond to a decrease in airway pressure. An airway therapy device that cannot accurately discern and implement opposing treatment options is unlikely to provide optimum therapy. Further, home airway therapy equipment does not include monitoring the arterial blood oxygen status of the patient, as is done with the PSG system pulse oximeter. Adding the increased physiologic insight provided by the ECM to the sensor capabilities of home airway therapy equipment potentially provides a much richer information base, or data set, from which to regulate therapy. Also, the disclosed therapy system can potentially detect and automatically respond to even subtle changes in the patient's therapy needs over time.

In another related application, the disclosed sensor systems may obtain nightly recordings from the disclosed sensors during sleep that can be conveyed electronically to a central data repository for research, and as a mechanism for continuous surveillance of individual patients. Automated algorithms are configurable to scan the data as it arrives and compare it with prior recordings of the same patient to detect if significant changes have occurred; thus, generating a daily list of 'case reviews' for directed evaluation by sleep medicine specialists. This continuously growing database of SDB information can also be useful for correlation with research in areas of co-morbidity, including neurology, pulmonology, and cardiology. The widely published, but still poorly understood, statistical linkage between snoring and risk of hypertension, has been identified by qualified sleep medicine physicians as a high priority for future research using the ECM sensor to identify and more clearly define the cause-effect linkage. Preliminary evidence shows the occurrence of cellular hypoxia in the skin at the onset of sleep-snoring periods and continuing throughout the duration of snoring. The UCSF POC studies documented that the ECM sensor provides key missing information that is not, and cannot be, produced by pulse oximetry in current technology PSG sleep studies. Addition of ECM recording to PSG testing is anticipated to enhance the sensitivity and specificity of the 'gold standard' diagnostic method.

In another related application, the disclosed sensors may be used to perform continuous or intermittent surveillance of SDB in persons being treated at home. As stated above, one of the most critical current deficiencies of clinical SDB therapy is the lack of objective surveillance following the diagnosis and initial titration of therapy equipment in a fully equipped sleep lab. It is inevitable that the human body ages with time and becomes progressively less physiologically stable—ultimately resulting in death. The application of the ECM as an integral part of on-going airway therapy control, in conjunction with cell phone text, or Internet conveyance of data to a back-end sleep medicine professional service organization, allows for continuous, objective, and relevant surveillance and professional guidance over time. Early detection of deterioration, or of a new health problem that affects SDB, is likely to be a clear, and potentially lifesaving, benefit of such an integrated care system.

Home Monitoring and Surveillance Following Hospital Discharge

In another example, the disclosed sensors may be used to provide continuous surveillance of adults with chronic health conditions and following discharge from the hospital. Continuous home monitoring of chronic heart failure and chronic lung disease in the elderly needs an integrated approach. Abnormal breathing and other common forms of physiologic stress cannot be monitored at home to the degree of sensitivity and responsiveness needed to optimally monitor these key variables. As the patient recovers in the hospital, and upon discharge home, an armband ECM sensor could provide useful surveillance for delayed-onset complications.

Cellular Oxygen Supply Surveillance During Anesthesia and Post-Anesthesia

In another example, the disclosed sensors may be used to provide cellular oxygen supply surveillance of patients undergoing surgical anesthesia and during their post-anesthesia recovery. The demonstrated diagnostic superiority of the disclosed sensor, vs. pulse oximetry, for detecting abnormal ventilation of the lungs, and for detecting both insufficient and excessive intake of oxygen, offers a significant benefit to patients, and improved clinical guidance during and following surgery. The additional sensitivity of the disclosed sensors to decreased skin perfusion and to decreased cellular oxygen delivery to the skin, offers a highly relevant new monitor for decreased blood volume and for decreased oxygen carrying capacity of the blood due to blood loss and blood dilution by IV fluids, both of which are common risks during surgery that are not detectable with pulse oximetry and that may not otherwise be recognized until a life-threatening crisis develops; potentially resulting in an adverse outcome.

Screening for SIDS

In another example, the disclosed sensors may be used to screen newborn infants for risk of dying from SIDS. Body position and posture during sleep have been noted as aggravating factors in SDB and are clearly defined as part of the risk of SIDS in infants. Infants lying on their back are statistically at about half the risk of SIDS when statistically compared with equal-risk infants sleeping on their stomach. Infants are known to normally have recurring periods of no breathing, or apnea, during sleep; also called periodic breathing. The disclosed sensors are configurable to detect when breathing timing and effort changes in periodic phases as an indication of periodic breathing during sleep. The sensor system is configurable to detect a progressive increase in breathing effort with successive periodic breathing phases as an indication that a potentially lethal condition of 'run-away' loop gain may be occurring, such as possibly occurs with SIDS-risk infants. The sensors are configurable to enable an alarm response to detected 'run-away' loop gain and to prolonged apnea events to: (1) alert caregiver/s for immediate intervention, and (2) to simultaneously produce a mechanical vibration haptic stimulus on an infant's arm, in an attempt to arouse the infant from sleep to abort the periodic breathing or potentially life-threatening prolonged period of central apnea.

Detection of Decreased Skin Perfusion

Another useful application of the disclosed sensor is detection of decreased perfusion of the skin, such as at the onset of septic shock. The disclosed sensor will detect decreased skin perfusion by decreased detected intensity of the 685 nm simultaneous with a stable or increased detected intensity of the 850 nm light, producing a continuously decreasing ECi trend, typically initially in context with stable $SpO_2$ by pulse oximetry. Clinical assessment for the onset of septic shock is currently performed with a capillary-refill test procedure at the time of routine vital signs checks during hospital care. However, the time interval between such checks and the need for a skilled clinician to perform the test commonly delays detection. Using the disclosed sensor for continuous in-patient monitoring of patients considered to be at risk of sepsis provides a continuous, highly sensitive, and responsive means of relevant surveillance to detect this common and potentially lethal complication of medical and surgical care. When applied during the period immediately following discharge from the hospital, the disclosed sensor also offers clinically remote 'early warning' surveillance; potentially improving quality of outcomes while enabling earlier hospital discharges and reducing healthcare costs.

Reperfusion of Ischemic Tissue

In a dual interface example, the disclosed sensors may be used to guide reperfusion of ischemic tissue. A first sensor interface is placed on a normal reference tissue, such as normally perfused skin, while a second interface is placed on the ischemic tissue, such as, as one example, the affected portion of myocardium of the heart during reperfusion treatment of an ischemic heart attack. Detection of an ECi trend overshoot on sudden re-supply of normally oxygen saturated blood to monitored tissue is consistently seen after an experimentally induced period of halted blood flow. The rapid increase in detected intensity at 685 nm typically to a level much greater than that from a reference, unaffected sensor site, indicates that the tissue is currently adapted to a lower rate of cellular oxygen supply. The sensors are also configurable to indicate, by detection of increased intensity at 685 nm, simultaneous with decreased detected intensity at 850 nm in response to increased oxygen content of reperfusion blood, that the reperfusion blood is supplying a potentially damaging level of oxygen to the monitored tissue, thereby enabling a therapeutic step-back in oxygen supply to a safer and more effective rate. The disclosed sensor may also provide feedback control data to automatically operate the venous/arterial blood blending system of the reperfusion pump.

Organ Transplantation

Another example of application of a dual-probe example of the disclosed sensors is to provide objective guidance regarding the safe and effective increase in supply of oxygen in blood reperfusion of a transplant organ, where a first sensor interface is placed on a reference 'normal' tissue, such as the patient's skin. In this application, the second sensor interface is placed in optical contact with the transplant organ being reperfused to indicate the cellular tolerance of the oxygen supplied by variably blended venous and arterial perfusion blood, until only arterial blood is used with no photonic evidence of cellular hyperoxia. The disclosed sensor may also provide feedback control data to automatically operate the venous/arterial blood blending system.

Premature Infant Monitoring

In another example of application of a dual interface example, the disclosed sensors can be applied to premature newborn infants to indicate, by detecting increased intensity at 685 nm along, along with detecting decreased intensity at 850 nm, in response to increased oxygen fraction in the breathing gas, that the monitored tissue, such as the pre-ductal skin of a premature newborn infant, is being supplied with more than the safe and effective level of oxygen; enabling a therapeutic step-back in breathing gas oxygen content to a safer and more effective rate. The disclosed sensor and associated new methods of use can be applied to help provide sufficient time for cellular adaptation to higher oxygen availability, such as with a newborn infant acclimating to breathing air; thereby, minimizing or preventing 'oxidative stress' injuries to the eyes, brain, and other vital organs. The disclosed sensor may also provide feedback control data to automatically operate a breathing gas blending system to adjust the oxygen level in a physiologically safe and effective manner.

Athletes

In another example, the disclosed sensors may be used to provide continuous surveillance of athletes during and following exercise. It is well known by exercise physiologists and noted in published research literature that blood oxygen saturation, as measured by blood gas and $SpO_2$, is not affected by physical exertion in healthy adult athletes. Faster heart rate and deeper, more rapid breathing are well-known reflex-driven means of increasing oxygen intake in response to increased oxygen consumption by working muscles. However, ECM recordings during physical exertion have shown that there is also a natural microvascular response in the skin that reduces oxygen consumption in the skin, presumably in order to better supply the oxygen needs of working muscles and vital organs during exertion. Decreased blood perfusion of the skin during physical exertion consistently results in cellular hypoxia in the skin that is detected by the ECM sensor; even without a drop in $SpO_2$. Experimental recordings during multiple exercise sessions have demonstrated newly observed patterns of physiologic response that go far beyond heart rate, heart rate variability, and pulse oximetry in assessing work load, vs. the person's physiologic reserve and response characteristics. During athletic exercise recovery time periods, the addition of ECi data provides currently missing physiologic insights. Sleep quality monitoring, including detection of cellular hypoxia-producing snoring episodes during sleep, is lacking in current technology fitness and $SpO_2$ monitoring. When the disclosed sensors are applied to athletes during sleep, the data produced can assess breathing during sleep and provide potentially relevant new insights, along with information from existing methods of monitoring, regarding the recovery process.

Worker Surveillance

In another example, the disclosed sensors may be used to provide continuous surveillance of workers in high-risk breathing environments, such as astronauts, divers, firefighters, underground mine workers, and workers in potentially toxic industrial environments where pulse oximeter sensors either cannot be worn or will not function properly or in a useful manner.

Pilot Surveillance

In another example, the disclosed sensors may be used to provide continuous surveillance of military pilots flying high-performance aircraft in training and combat. It is well known that these pilots are at risk of hypoxia from loss of cockpit air pressure at high altitude. They are also at risk of loss of blood flow to their head while performing high g-load-inducing maneuvers of the aircraft. Either or both of these threats may suddenly incapacitate the pilot without any indication of malfunction of the aircraft systems. Application of the disclosed sensor to the pilot's forehead will provide an immediate, objective indication of either cellular hypoxia in the forehead skin, or loss of blood flow in the skin, or both. If these detected physiologic responses in the pilot are communicated automatically to the aircraft controls, an automated pilot-rescue process may be triggered to maneuver the aircraft to a stable, safe flight status and inform command personnel of the emergency. If the pilot can recover control of the aircraft once the threats are automatically resolved, he/she may continue the mission.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An Energy Conversion Monitor sensor comprising:
   a housing;
   a power source;
   a first light emitter positioned within an interior of the housing configured to emit a first light at a first wavelength;
   a second light emitter positioned within the interior of the housing configured to emit a second light at a second wavelength different than the first wavelength;
   a light detector positioned within the interior of the housing and optically isolated from the first light emitter and the second light emitter wherein the light detector is configured to detect a resulting first tissue-interacted light signal from the first light emitter and a second tissue-interacted light signal from the second light emitter;
   an illumination power control circuit in communication with the first light emitter and the second light emitter wherein the illumination power control circuit is configured to provide a computer program-defined illumination power to energize the first light emitter and the second light emitter at a respective computer program-defined illumination intensity;
   a signal amplifier in communication with the light detector; and
   a microcontroller configured to compute a first output data value from the first tissue-interacted light and a second output data from the second tissue-interacted light,
   wherein the microcontroller is configurable to compensate during an initialization process for a variation in a skin pigmentation level by step-wise increasing a power delivered to the first light emitter up to a sustainable maximum rated power level for the first light emitter, and
   further wherein if a detected intensity at 85% full scale is not detectable when the sustainable maximum rated power level for the first light emitter is reached, the microcontroller is configurable to implement an oversampling and mathematical integration method.

2. The Energy Conversion Monitor sensor of claim 1 wherein the Energy Conversion Monitor sensor uses a plurality of wavelengths of light selected by in vivo spectrometry.

3. The Energy Conversion Monitor sensor of claim 2 wherein the plurality of wavelengths of light are selected to maximize a respective variation in detected cellular light absorbance relative to at least one of a known cellular biochemical phenomenon and a known physiologic phenomenon affecting a monitored tissue.

4. The Energy Conversion Monitor sensor of claim 1 wherein the first light emitter has a first light emitter center wavelength value of from 675 nm to 695 nm inclusive.

5. The Energy Conversion Monitor sensor of claim 1 wherein the microcontroller is configurable to increase a number of burst samples beyond a nominal number, sum all of the burst sample values, and divide the sum of all of the burst samples by the nominal number until a computed intensity value equal or greater than 85% full scale is achieved.

6. The Energy Conversion Monitor sensor of claim 1 wherein the second light emitter has a second light emitter center wavelength value of from 840 nm to 860 nm inclusive.

7. The Energy Conversion Monitor sensor of claim 1 wherein the light detector detects the first tissue-interacted light signal and the second tissue-interacted light signal at one or more timed intervals.

8. A method of using an Energy Conversion Monitor sensor comprising the steps of:
   applying an Energy Conversion Monitor sensor to a skin surface of a patient wherein the Energy Conversion Monitor sensor comprises a housing, a power source, a first light emitter positioned within an interior of the housing configured to emit a first light at a first wavelength, a second light emitter positioned within the interior of the housing configured to emit a second light at a second wavelength different than the first wavelength, a light detector positioned within the interior of the housing and optically isolated from the first light emitter and the second light emitter wherein the light detector is configured to detect a resulting first tissue-interacted light signal from the first light emitter and a second tissue-interacted light signal from the second light emitter, an illumination power control circuit in communication with the first light emitter and the second light emitter wherein the illumination power control circuit is configured to provide a computer program-defined illumination power to energize the first light emitter and the second light emitter at a respective computer program-defined illumination intensity, a signal amplifier in communication with the light detector, and a microcontroller configured to compute a first output data value from the first tissue-interacted light and a second output data from the second tissue-interacted light;
   powering the Energy Conversion Monitor sensor
   delivering a power level to the Energy Conversion Monitor sensor to equalize a first detected intensity of light at a first wavelength between 675 nm and 695 nm inclusive with a second detected intensity of light at a second wavelength between 840 nm and 860 nm inclusive;
   determining a first detected intensity of light from a first tissue interacted light signal;
   determining a second detected intensity of light from a second tissue interacted light signal;

comparing the first detected intensity of light to a first full scale to determine a first percentage detected intensity of light;

comparing the second detected intensity of light to a second full scale to determine a second percentage detected intensity of light; and repeating the delivering, determining, and comparing steps to obtain a detected intensity of light at 85% of full scale for each of the first detected intensity of light and the second detected intensity of light.

9. The Energy Conversion Monitor sensor method of claim 8 further comprising the step of:

storing the power level and a total number of burst samples added together and divided by a nominal number of burst samples to achieve a detected, integrated intensity of tissue interacted light from the first emitter of 85% full scale in a memory, and storing the power level to achieve a detected intensity of tissue interacted light from the second emitter of 85% full scale in a memory.

10. The Energy Conversion Monitor sensor method of claim 9 further comprising the step of:

using the stored power level of a first emitter and the number of burst samples of detected tissue interacted light from a first emitter, and the stored power level of a second emitter, as control parameters in data acquisition through a current recording session.

11. The Energy Conversion Monitor sensor method of claim 8 further comprising the step of:

initializing the Energy Conversion Monitor sensor;

subtracting a detected intensity from the second light emitter (between 840 nm and 860 nm inclusive), following tissue interaction with a second light, from the detected intensity from the first light emitter (between 675 nm and 695 nm inclusive), following tissue interaction with a first light, to produce an Energy Conversion Index (ECi) output as an at least 12-bit resolution; and generating an integer numeric value analog indication of a status of cellular oxygen supply-related chemistry.

12. The Energy Conversion Monitor sensor method of claim 8 further comprising the step of:

computing one of a cellular oxygen supply-related center and an Energy Conversion Index Zero (ECi Zero) of a user; and applying an offset value to a center the data output of an Energy Conversion Monitor sensor output data.

13. The Energy Conversion Monitor sensor method of claim 8 further comprising the step of:

performing a calculation averaging a period of low activity to define and record an offset numeric value relative to zero;

determining a current ECi Zero for a patient; and applying a recorded offset numeric value to center the recorded data on a current ECi Zero of the patient.

14. The Energy Conversion Monitor sensor method of claim 8 further comprising the step of:

indicating, in response to an ECi data less than zero produced by decreased detected intensity at 685 nm along with simultaneous stable detected intensity at 850 nm, a cellular oxygen supply less than physiologically optimum.

15. The Energy Conversion Monitor sensor method of claim 8 further comprising the step of:

indicating, in response to an ECi data greater than zero produced by stable or increased detected first intensity between 675 nm and 695 nm inclusive along with simultaneous stable or decreased second detected intensity between 840 nm and 860 nm inclusive, a cellular oxygen supply more than physiologically optimum.

16. The Energy Conversion Monitor sensor method of claim 8 further comprising the step of:

identifying an indication of changing blood volume beneath the Energy Conversion Monitor sensor resulting from at least one of an Energy Conversion Monitor sensor motion against the skin and a change of body position vs. gravity during sleep causing a tandem variation in a first detected light intensity between 675 nm and 695 nm inclusive and a second detected light intensity between 840 nm and 860 nm inclusive.

17. The Energy Conversion Monitor sensor method of claim 8 further comprising the step of:

generating a generated signal between 840 nm and 860 nm inclusive; and detecting the generated signal at a sufficiently frequent timed interval to define an amplitude and a waveform of a breathing-induced, light intensity variation as an indication of one of an increased effort to breathe through a restricted or obstructed airway, and a decreased or absent effort to breathe from a reduced or absent central nervous system breathing drive.

18. The Energy Conversion Monitor sensor method of claim 8 further comprising the step of:

applying the Energy Conversion Monitor sensor on a person identified as possibly suffering from sleep disordered breathing (SDB);

monitoring breathing and oxygen supply-related physiology during sleep of the person; and providing recorded data from the monitoring to aid in clinical diagnosis of SDB to help define, validate, and regulate effective therapy.

19. The Energy Conversion Monitor sensor method of claim 8 further comprising the step of:

applying the Energy Conversion Monitor sensor to a person having sleep disordered breathing (SDB) while sleeping at home while using an SDB therapy device; and determining an extent of management of the SDB.

20. The Energy Conversion Monitor sensor method of claim 8 further comprising the step of:

applying the Energy Conversion Monitor sensor to a person while sleeping at home while using a sleep disordered breathing (SDB) therapy device to provide ECi and breathing information to the SDB therapy device;

controlling the SBD therapy device in response to at least one of the ECi and breathing information from the Energy Conversion Monitor sensor; and providing surveillance during sleep for changes in the person's general health status.

21. The Energy Conversion Monitor sensor method of claim 8 further comprising the step of:

applying the Energy Conversion Monitor sensor on a person identified as at risk of developing sepsis; and detecting the possible presence of sepsis as from an ECi value progressively trending less than zero.

22. The Energy Conversion Monitor sensor method of claim 8 further comprising the step of:

applying the Energy Conversion Monitor sensor to an infant; and screening the infant for a risk of SIDS by recording a stability and effectiveness of breathing during sleep.

23. The Energy Conversion Monitor sensor method of claim 8 further comprising the step of:
applying the Energy Conversion Monitor sensor to an infant;
monitoring a stability and effectiveness of breathing during sleep; and
one or more of delivering a stimulation to arouse the infant from sleep during episodes of detected abnormal breathing during sleep, and delivering an alarm identifying the detected abnormal breathing to a caregiver.

24. The Energy Conversion Monitor sensor method of claim 8 further comprising the step of:
applying the Energy Conversion Monitor sensor to a newborn infant; and
providing feedback to a caregiver for use in regulating an oxygen level in a breathing gas relative to a cellular oxygen need as the infant transitions from fetal life to a higher level of oxygen available from breathing air, or higher levels of oxygen, to help reduce or prevent oxygen supply-related injuries.

25. The Energy Conversion Monitor sensor method of claim 8 further comprising the step of:
applying the Energy Conversion Monitor sensor during a resuscitation of a person suffering from at least one of hypoxia and suffocation; and
guiding a regulation of oxygen in a breathing gas relative to a cellular oxygen need of the person.

26. The Energy Conversion Monitor sensor method of claim 8 further comprising the step of:
applying the Energy Conversion Monitor sensor to a worker in a high-risk atmospheric environment; and
monitoring the worker for at least one of hypoxia and adverse effects of toxic gases in their breathing air.

27. The Energy Conversion Monitor sensor method of claim 8 further comprising the step of:
applying the Energy Conversion Monitor sensor to a forehead of a pilot; and
monitoring the pilot for one or more of hypoxia and a g-load-induced loss of blood flow to the head.

28. The Energy Conversion Monitor sensor method of claim 8 further comprising the step of:
applying the Energy Conversion Monitor sensor to an athlete during and following physical exercise;
assessing physiologic responses of the athlete; and
providing a recommendation for optimum performance.

29. The Energy Conversion Monitor sensor method of claim 8 further comprising the step of:
applying the Energy Conversion Monitor sensor having a dual probe to a chest and abdomen of an infant patient in intensive care;
monitoring a pre-ductal cellular oxygen supply and a post-ductal cellular oxygen supply; and
detecting at least one of an anatomic anomaly of a heart, an anatomic anomaly of a great vessels, and a failure of a ductus arteriosus to close normally.

30. The Energy Conversion Monitor sensor method of claim 8 further comprising the step of:
applying the Energy Conversion Monitor sensor having a dual probe during at least one of reperfusion of a myocardium during therapy for ischemic heart attack, reperfusion of an affected area of a brain during therapy for a stroke, a reperfusion of a transplant organ, and a guide oxygen resupply to the ischemic tissue relative to cellular oxygen need to help reduce or prevent reperfusion injury.

31. A system comprising:
an Energy Conversion Monitor sensor comprising a housing, a power source, a first light emitter positioned within an interior of the housing configured to emit a first light at a first wavelength, a second light emitter positioned within the interior of the housing configured to emit a second light at a second wavelength different than the first intensity, a light detector positioned within the interior of the housing and optically isolated from the first light emitter and the second light emitter wherein the light detector is configured to detect a resulting first tissue-interacted light signal from the first light emitter and a second tissue-interacted light signal from the second light emitter, an illumination power control circuit in communication with the first light emitter and the second light emitter wherein the illumination power control circuit is configured to provide a computer program-defined illumination power to energize the first light emitter and the second light emitter at a respective computer program-defined illumination intensity, a signal amplifier in communication with the light detector, and a microcontroller configured to compute a first output data value from the first tissue-interacted light and a second output data from the second tissue-interacted light, wherein the microcontroller is configurable to compensate during an initialization process for a variation in a skin pigmentation level by step-wise increasing a power delivered to the first light emitter up to a sustainable maximum rated power level for the first light emitter, and further wherein if a detected intensity at 85% full scale is not detectable when the sustainable maximum rated power level for the first light emitter is reached, the microcontroller is configurable to implement an oversampling and mathematical integration method; and
at least one secondary device selected from a second sensor, a sleep disordered breathing (SDB) therapy device, a remote computing device, and a polysomnograph (PSG) system.

* * * * *